(12) United States Patent
Priepke et al.

(10) Patent No.: US 6,479,524 B1
(45) Date of Patent: Nov. 12, 2002

(54) SUBSTITUTED ARYL AND HETEROARYL DERIVATIVES, THEIR PRODUCTION AND THEIR USE AS MEDICINES

(75) Inventors: Henning Priepke, Warthausen (DE); Iris Kauffmann-Hefner, Attenweiler (DE); Norbert Hauel, Schemmerhofen (DE); Uwe Ries, Biberach (DE); Herbert Nar, Mittelbiberach (DE); Jean Marie Stassen, Leuven (BE); Wolfgang Wienen, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/868,428

(22) PCT Filed: Dec. 13, 1999

(86) PCT No.: PCT/EP99/09921

§ 371 (c)(1),
(2), (4) Date: Oct. 18, 2001

(87) PCT Pub. No.: WO00/35859

PCT Pub. Date: Jun. 22, 2000

(30) Foreign Application Priority Data

Dec. 16, 1998 (DE) .......................................... 198 58 029
Oct. 7, 1999 (DE) .......................................... 199 48 101

(51) Int. Cl.$^7$ ..................... C07D 213/50; C07C 257/18; A61K 31/415
(52) U.S. Cl. ..................... 514/352; 514/423; 514/637; 514/564; 546/309; 548/530; 564/161; 564/244; 562/439; 562/440
(58) Field of Search ................... 562/439, 440; 514/564, 352, 423, 637; 546/309; 548/530; 564/161, 244

(56) References Cited

FOREIGN PATENT DOCUMENTS

| EP | 0 760 364 A | 3/1997 |
| EP | 0 805 149 A | 11/1997 |
| WO | WO95 18111 A | 7/1995 |

*Primary Examiner*—Zinna Northington Davis
(74) *Attorney, Agent, or Firm*—Robert P. Raymond; Alan R. Stempel; Mary-Ellen M. Devlin

(57) ABSTRACT

Compounds that prolong thrombin time. Exemplary are:

(a) rac-4-{3-[5-ethoxycarbonylmethyl-2-methyl-4-(2-methyl-pyrrolidinocarbonyl)-phenyl]-propargylamino}benzamidine,
(b) rac-4-{3-[2,5-dimethyl-4-(2-methyl-pyrrolidinocarbonyl)-phenyl]-propargylamino}benzamidine, and
(c) 4-[3-(2,5-dimethyl-4-isopropylcarbonyl-phenyl)propargyl-amino]benzamidine.

7 Claims, No Drawings

SUBSTITUTED ARYL AND HETEROARYL DERIVATIVES, THEIR PRODUCTION AND THEIR USE AS MEDICINES

This application is derived from International Application PCT/EP99/09921 pursuant to 35 U.S.C. 371.

The present invention relates to new substituted aryl and heteroaryl derivatives of general formula

$$Ar—A—(HCR_1)—X—Y, \quad (I)$$

the tautomers, the stereoisomers, the mixtures thereof and the salts thereof, particularly the physiologically acceptable salts with inorganic or organic acids or bases which have valuable properties.

The compounds of the above general formula I wherein Y does not contain a cyano group, have valuable pharmacological properties, particularly an antithrombotic activity, and the compounds of the above general formula I wherein Y contains a cyano group, are valuable intermediate products for preparing the compounds of general formula I wherein $R_5$ denotes an optionally substituted amino-$C_{1-3}$-alkyl, amidino, guanidino or guanidino-$C_{1-3}$-alkyl group.

The present invention thus relates to the new compounds of the above general formula I and the preparation thereof, the pharmaceutical compositions containing the pharmacologically active compounds and their use.

In the above general formula

A denotes an ethynylene group, a vinylene or ethylene group optionally substituted by a $C_{1-3}$-alkyl or carboxy-$C_{1-3}$-alkyl group or by a chlorine, bromine or iodine atom, $R_1$ denotes a hydrogen atom, a $C_{1-3}$-alkyl or carboxy-$C_{1-3}$-alkyl group, Ar denotes a phenyl group substituted by the groups $R_2$ to $R_4$, wherein $R_2$ denotes a $C_{1-6}$-alkyl- or $C_{3-7}$-cycloalkyl-$C_{1-3}$-alkyl group, which may be substituted in the $C_{1-6}$- and $C_{1-3}$-alkyl moieties by a carboxy, phenyl, amino, $C_{1-3}$-alkylamino, carboxy-$C_{1-3}$-alkylamino, di-($C_{1-3}$-alkyl)-amino, N-(carboxy-$C_{1-3}$-alkyl)-$C_{1-3}$-alkylamino, $C_{3-7}$-cycloalkylamino, phenylamino, N—($C_{1-3}$-alkyl)-phenylamino, N—($C_{1-4}$-alkanoyl)-phenylamino, heteroarylamino, N—($C_{1-3}$-alkyl)-heteroarylamino, N-(carboxy-$C_{1-3}$-alkyl)-phenylamino or N-(carboxy-$C_{1-3}$-alkyl)-heteroarylamino group, a carboxy-$C_{1-5}$-alkyl group which is substituted in the alkyl moiety by a $C_{1-3}$-alkylamino, N,N-di-($C_{1-3}$-alkyl)-amino, pyrrolidino, piperidino or hexamethyleneimino group, a carboxy-$C_{1-5}$-alkyl group wherein the hydrogen atoms of a methylene group are replaced by a n-$C_{2-5}$-alkylene bridge, a phenyl, phenyloxy or phenylsulphonyl group, which may be substituted in each case in the phenyl moiety by a fluorine, chlorine, bromine or iodine atom, by a $C_{1-3}$-alkyl, carboxy-$C_{1-3}$-alkyl or $C_{1-3}$-alkoxy group, a $C_{1-5}$-alkylamino, carboxy-$C_{1-3}$-alkylamino, di-($C_{1-5}$-alkyl)-amino, N-(carboxy-$C_{1-3}$-alkyl)-$C_{1-5}$-alkylamino, $C_{3-7}$-cycloalkylamino, N-(carboxy-$C_{1-3}$-alkyl)-$C_{3-7}$-cycloalkylamino, phenylamino, N—($C_{1-3}$-alkyl)-phenylamino, N-(carboxy-$C_{1-3}$-alkyl)-phenylamino, heteroarylamino, N—($C_{1-3}$-alkyl)-heteroarylamino or N-(carboxy-$C_{1-3}$-alkyl)-heteroarylamino group, a $C_{1-5}$-alkylcarbonylamino, $C_{3-7}$-cycloalkylcarbonylamino, arylcarbonylamino, heteroarylcarbonylamino, $C_{1-5}$-alkylsulphonylamino, arylsulphonylamino, heteroarylsulphonylamino, N—($C_{1-3}$-alkyl)-$C_{1-5}$-alkylcarbonylamino, N—($C_{1-3}$-alkyl)-$C_{3-7}$-cycloalkylcarbonylamino, N—($C_{1-3}$-alkyl)-arylcarbonylamino, N—($C_{1-3}$-alkyl)-heteroarylcarbonylamino, N—($C_{1-3}$-alkyl)-$C_{1-5}$-alkylsulphonylamino, N—($C_{1-3}$-alkyl)-arylsulphonylamino or N—($C_{1-3}$-alkyl)-heteroarylsulphonylamino group, whilst the above-mentioned N—($C_{1-3}$-alkyl) moieties may additionally be substituted by a carboxy, carboxy-$C_{1-3}$-alkylaminocarbonyl or N—($C_{1-3}$-alkyl)-carboxy-$C_{1-3}$-alkylaminocarbonyl group or, with the exception of the α-carbon atom in relation to the nitrogen atom, by a hydroxy, carboxy-$C_{1-3}$-alkoxy, amino, carboxy-$C_{1-3}$-alkylamino or N—($C_{1-3}$-alkyl)-carboxy-$C_{1-3}$-alkylamino group, a 5- to 7-membered cycloalkyleneimino group, an amino, $C_{1-5}$-alkylamino, $C_{3-7}$-cycloalkylamino, arylamino, aryl-$C_{1-3}$-alkylamino, heteroarylamino or heteroaryl-$C_{1-3}$-alkyl-amino group, which are substituted in each case at the amino nitrogen atom by a $C_{1-3}$-alkylcarbonyl, carboxy-$C_{1-3}$-alkylcarbonyl, carboxy-$C_{1-3}$-alkylaminocarbonyl, 2-oxo-pyrrolidinylcarbonyl or piperazinocarbonyl group, whilst additionally (i) the above-mentioned amino group, which is monosubstituted by a $C_{1-3}$-alkylcarbonyl, carboxy-$C_{1-3}$-alkylcarbonyl or carboxy-$C_{1-3}$-alkylaminocarbonyl group, is substituted by a 5- to 7-membered cycloalkyleneimino group or by a N,N-di-($C_{1-5}$-alkyl)-amino group, and (ii) the alkyl moiety of the above-mentioned $C_{1-3}$-alkylcarbonyl group is substituted by a carboxy, amino, hydroxy, carboxy-$C_{1-3}$-alkoxy, carboxy-$C_{1-3}$-alkylaminocarbonyl, carboxy-$C_{1-3}$-alkylamino, N—($C_{1-3}$-alkyl)-carboxy-$C_{1-3}$-alkylamino or amino-$C_{1-3}$-alkylcarbonylamino group or by a carboxy or hydroxy group and by an amino or trifluoroacetylamino group, a carbimino group which is substituted at the nitrogen atom by a carboxy-$C_{1-3}$-alkoxy, amino, $C_{1-3}$-alkylamino, carboxy-$C_{1-3}$-alkylamino, di-($C_{1-3}$-alkyl)-amino or N-(carboxy-$C_{1-3}$-alkyl)-$C_{1-3}$-alkylamino group and at the carbon atom by a $C_{1-5}$-alkyl group, by a phenyl group optionally substituted by a $C_{1-3}$-alkyl or $C_{1-3}$-alkoxy group or by a heteroaryl group optionally substituted by a $C_{1-3}$-alkyl group, a heteroaryl or heteroaryl-$C_{1-3}$-alkyl group, which may in each case additionally be substituted in the heteroaryl moiety by a phenyl or heteroaryl group or by a phenyl or heteroaryl group and by a carboxy-$C_{1-3}$-alkyl or $C_{1-3}$-alkoxycarbonyl-$C_{1-3}$-alkyl group, a 5-oxo-4,5-dihydro-pyrazolyl or 6-oxo-4,5-dihydro-pyridazinyl group optionally substituted by 1 to 3 $C_{1-3}$-alkyl groups wherein an alkyl substituent may at the same time be substituted by a carboxy or $C_{1-3}$-alkoxycarbonyl group, or a carbonyl group which is substituted
  by a hydrogen atom, by a hydroxy, $C_{1-5}$-alkoxy or $C_{3-7}$-cycloalkoxy group,
  by a $C_{1-5}$-alkyl or $C_{3-7}$-cycloalkyl group optionally substituted by a carboxy group,
  by a $C_{1-3}$-alkyl group substituted by a piperazino group,
  by a phenyl group which may be substituted by a fluorine, chlorine, bromine or iodine atom, by a $C_{1-3}$-alkyl, carboxy-$C_{1-3}$-alkyl, $C_{1-3}$-alkoxy or carboxy group,
  by an amino, $C_{1-5}$-alkylamino, carboxy-$C_{1-3}$-alkylamino, $C_{3-7}$-cycloalkylamino, phenylamino or heteroarylamino group, each of which may additionally be substituted at the amino nitrogen atom by a $C_{1-5}$-alkyl, $C_{3-7}$-Cycloalkyl, phenyl-$C_{1-3}$-alkyl, carboxy-$C_{1-3}$-alkyl, 2-[di-($C_{1-3}$-alkyl)-amino]-ethyl, 3-[di-($C_{1-3}$-alkyl)-amino]-propyl, di-($C_{1-3}$-alkyl)-amino, 2-(N-carboxy-$C_{1-3}$-alkyl-$C_{1-3}$-alkylamino)-ethyl, 3-(N-carboxy-$C_{1-3}$-alkyl-$C_{1-3}$-alkylamino)-propyl or N-carboxy-$C_{1-3}$-alkyl-$C_{1-3}$-alkylamino, phenyl, pyridyl, pyrrolidinyl or piperidinyl group,
  by a pyrrolyl, thienyl, imidazolyl, pyrazolyl, thiazolyl, pyridinyl, pyrimidinyl, pyrazinyl or pyridazinyl group optionally substituted by one or two $C_{1-3}$-alkyl groups onto which a phenyl ring may be fused via two adjacent carbon atoms,
  by a $C_{3-6}$-cycloalkyleneimino, $C_{5-8}$-bicycloalkyleneimino, morpholino, piperazino, dihydropyrazolo, tetrahydropyrazolo, tetrahydroisoxazolo, tetrahydropyrazinyl or tetrahydropyridazinyl group optionally substituted by a $C_{1-3}$-alkyl or carboxy-$C_{1-3}$-alkyl group or
  by a $C_{3-6}$-cycloalkyleneimino group optionally substituted by a $C_{1-3}$-alkyl, carboxy-$C_{1-3}$-alkyl, hydroxy, hydroxy-$C_{1-3}$-alkyl, amino, carboxy, carboxy-$C_{1-3}$-alkoxy-$C_{1-3}$-alkyl, carboxy-$C_{1-3}$-alkylamino-$C_{1-3}$-alkyl or carboxy-$C_{1-3}$-alkylaminocarbonyl-$C_{1-3}$-alkyl group,
  by a $C_{5-8}$-bicycloalkyleneimino, morpholino, piperazino, dihydropyrazolo, tetrahydropyrazolo, tetrahydroisoxazolo, tetrahydropyrazinyl or tetrahydropyridazinyl group optionally substituted by a $C_{1-3}$-alkyl or carboxy-$C_{1-3}$-alkyl group, $R_3$ denotes
  a hydrogen, fluorine, chlorine, bromine or iodine atom, a formyl or trifluoromethyl group,
  a $C_{1-3}$-alkoxy, amino, $C_{1-3}$-alkylamino, di-($C_{1-3}$-alkyl)-amino, $C_{1-4}$-alkanoylamino or N—($C_{1-4}$-alkanoyl)-$C_{1-3}$-alkylamino group,
  a $C_{1-3}$-alkyl group optionally substituted by a hydroxy, $C_{1-3}$-alkoxy, carboxy, carboxy-$C_{1-3}$-alkoxy, carboxy-$C_{1-3}$-alkylamino, N—($C_{1-3}$-alkyl)-carboxy-$C_{1-3}$-alkylamino or carboxy-$C_{1-3}$-alkylaminocarbonyl group,
  a $C_{2-3}$-alkenyl group substituted by a carboxy or carboxy-$C_{1-3}$-alkylaminocarbonyl group or
  a carbimino group optionally substituted at the carbon atom by a $C_{1-3}$-alkyl group, which is substituted at the imino nitrogen atom by a carboxy-$C_{1-3}$-alkoxy or aminocarbonylamino group, or $R_2$ and $R_3$ together denote a —CO—O—$CH_2$— or —CO—O—$CH_2CH_2$— group and $R_4$ denotes a hydrogen, fluorine, chlorine, bromine or iodine atom, a $C_{1-3}$-alkyl, $C_{3-7}$-cycloalkyl, trifluoromethyl or $C_{1-3}$-alkoxy group, or Ar may also denote a heteroaryl group which may be substituted by the above-mentioned groups $R_2$ to $R_4$, which are as hereinbefore defined, X denotes an oxygen or sulphur atom, a methylene group, a carbonyl, sulphinyl, sulphonyl, imino, N—($C_{1-3}$-alkyl)-imino or N-(carboxy-$C_{1-3}$-alkyl)-imino group optionally substituted by one or two $C_{1-3}$-alkyl groups, whilst the alkyl moiety of the N—($C_{1-3}$-alkyl)-imino group may additionally be substituted in the 2- or 3-position by an amino, $C_{1-3}$-alkylamino, di-($C_{1-3}$-alkyl)-amino, $C_{1-4}$-alkanoylamino or N—($C_{1-4}$-alkanoyl)-$C_{1-3}$-alkylamino group, and Y denotes a cyclohexyl group substituted by an amino group or a phenyl or heteroaryl group substituted by the group $R_5$, whilst the above-mentioned phenyl group may be substituted in each case by a fluorine, chlorine, bromine or iodine atom or by a $C_{1-3}$-alkyl or $C_{1-3}$-alkoxy group and the above-mentioned heteroaryl group may be substituted by a $C_{1-3}$-alkyl group and $R_5$ denotes a hydrogen atom, a cyano group or an amino, amino-$C_{1-3}$-alkyl, amidino, guanidino or guanidino-$C_{1-3}$-alkyl group optionally substituted by a group which may be cleaved in vivo.

By the above-mentioned heteroaryl groups is meant a 5-membered heteroaromatic group optionally substituted by one or two $C_{1-3}$-alkyl groups which contains an imino group optionally substituted by a $C_{1-3}$-alkyl group, an oxygen or sulphur atom or an imino group optionally substituted by a $C_{1-3}$-alkyl group, an oxygen or sulphur atom and one or two nitrogen atoms and the partially hydrogenated derivatives thereof, particularly the dihydro derivatives thereof, or a 6-membered heteroaromatic group which contains one, two or three nitrogen atoms, whilst additionally a phenyl ring may be fused to the above-mentioned 5- and 6-membered heteroaromatic rings via two adjacent carbon atoms.

Moreover, the carboxy groups mentioned in the above definitions of the groups may be replaced by a tetrazolyl group or by a group which can be converted in vivo into a carboxy group, e.g. by a hydroxymethyl or formyl group, by a carboxy group esterified with an alcohol wherein the alcoholic moiety is preferably a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol, wherein a methylene group in the 3- or 4-position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bond to the oxygen atom starts from a carbon atom which carries a double or triple bond, a $C_{3-8}$-cycloalkyl-$C_{1-3}$-alkanol, a bicycloalkanol with a total of 8 to 10 carbon atoms which is additionally substituted by one or two $C_{1-3}$-alkyl groups in the bicycloalkyl moiety, a 1,3-dihydro-oxo-1-isobenzofuranol or an alcohol of formula

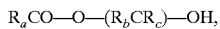

wherein
  $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, and the imino or amino groups mentioned in the definition of the groups may be substituted by a group which can be cleaved in vivo, e.g. by a hydroxy group, by an acyl group such as the benzoyl or pyridinoyl group or a $C_{1-16}$-alkanoyl group such as the formyl, acetyl, propionyl, butanoyl, pentanoyl or hexanoyl group, by an allyloxycarbonyl group, by a $C_{1-16}$-alkoxycarbonyl group such as the methyloxycarbonyl, ethyloxycarbonyl, propyloxycarbonyl, isopropyloxycarbonyl, butyloxycarbonyl, tert-butyloxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, by a phenyl-$C_{1-16}$-alkoxycarbonyl group such as the benzyloxycarbonyl, phenylethyloxycarbonyl or phenylpropyloxycarbonyl group, by a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_aCO-O-(R_bCR_c)-O-CO$-group, wherein $R_a$ to $R_b$ are as hereinbefore defined.

Moreover, the saturated alkyl and alkoxy moieties which contain more than 2 carbon atoms, as well as the alkanoyl and unsaturated alkyl moieties which contain more than 3 carbon atoms in the above-mentioned definitions also include the branched isomers thereof such as, for example, the isopropyl, tert-butyl, isobutyl group, etc.

Preferred compounds of general formula I of the present invention are those wherein A denotes an ethynylene group, a vinylene or ethylene group optionally substituted by a $C_{1-3}$-alkyl or carboxy-$C_{1-3}$-alkyl group or by a chlorine, bromine or iodine atom, $R_1$ denotes a hydrogen atom, a $C_{1-3}$-alkyl or carboxy-$C_{1-3}$-alkyl group, Ar denotes a phenyl group substituted by the groups $R_2$ to $R_4$, whilst $R_2$ denotes a $C_{1-3}$-alkyl group which may be substituted by a carboxy, phenyl, amino, $C_{1-3}$-alkylamino, carboxy-$C_{1-3}$-alkylamino, di-($C_{1-3}$-alkyl)-amino, N-(carboxy-$C_{1-3}$-alkyl)-$C_{1-3}$-alkylamino, phenylamino, N—($C_{1-3}$-alkyl)-phenylamino, N—($C_{1-4}$-alkanoyl)-phenylamino, heteroarylamino, N—($C_{1-3}$-alkyl)-heteroarylamino, N-(carboxy-$C_{1-3}$-alkyl)-phenylamino or N-(carboxy-$C_{1-3}$-alkyl)-heteroarylamino group, a phenyl or phenylsulphonyl group, which may be substituted in each case in the phenyl moiety by a fluorine, chlorine, bromine or iodine atom, by a $C_{1-3}$-alkyl, carboxy-$C_{1-3}$-alkyl or $C_{1-3}$-alkoxy group, a $C_{1-3}$-alkylamino, carboxy-$C_{1-3}$-alkylamino, di-($C_{1-3}$-alkyl)-amino, N-(carboxy-$C_{1-3}$-alkyl)-$C_{1-3}$-alkylamino, phenylamino, N—($C_{1-3}$-alkyl)-phenylamino, N-(carboxy-$C_{1-3}$-alkyl)-phenylamino, heteroarylamino, N—($C_{1-3}$-alkyl)-heteroarylamino or N-(carboxy-$C_{1-3}$-alkyl)-heteroarylamino group, a $C_{1-5}$-alkylcarbonylamino, arylcarbonylamino, heteroarylcarbonylamino, $C_{1-5}$-alkylsulphonylamino, arylsulphonylamino, heteroarylsulphonylamino, N—($C_{1-3}$-alkyl)-$C_{1-5}$-alkylcarbonylamino, N—($C_{1-3}$-alkyl)-arylcarbonylamino, N—($C_{1-3}$-alkyl)-heteroarylcarbonylamino, N—($C_{1-3}$-alkyl)-$C_{1-5}$-alkylsulphonylamino, N—($C_{1-3}$-alkyl)-arylsulphonylamino, N—($C_{1-3}$-alkyl)-heteroarylsulphonylamino, N-(carboxy-$C_{1-3}$-alkyl)-$C_{1-5}$-alkylcarbonylamino, N-(carboxy-$C_{1-3}$-alkyl)-arylcarbonylamino, N-(carboxy-$C_{1-3}$-alkyl)-heteroarylcarbonylamino, N-(carboxy-$C_{3}$-alkyl)-$C_{1-5}$-alkylsulphonylamino, N-(carboxy-$C_{1-3}$-alkyl)-arylsulphonylamino or N-(carboxy-$C_{1-3}$-alkyl)-heteroarylsulphonylamino group, a carbimino group which is substituted at the nitrogen atom by a carboxy-$C_{1-3}$-alkoxy, amino, $C_{1-3}$-alkylamino, carboxy-$C_{1-3}$-alkylamino, di-($C_{1-3}$-alkyl)-amino or N-(carboxy-$C_{1-3}$-alkyl)-$C_{1-3}$-alkylamino group and at the carbon atom by a $C_{1-5}$-alkyl group, by a phenyl group optionally substituted by a $C_{1-3}$-alkyl or $C_{1-3}$-alkoxy group or by a heteroaryl group optionally substituted by a $C_{1-3}$-alkyl group, a heteroaryl or heteroaryl-$C_{1-3}$-alkyl group, which may in each case additionally be substituted in the heteroaryl moiety by a phenyl or heteroaryl group or by a phenyl or heteroaryl group and by a carboxy-$C_{1-3}$-alkyl or $C_{1-3}$-alkoxycarbonyl-$C_{1-3}$-alkyl group, or a carbonyl group which is substituted
by a hydrogen atom, by a hydroxy, $C_{1-5}$-alkoxy or $C_{3-7}$-cycloalkoxy group,
by a $C_{1-5}$-alkyl or $C_{3-7}$-cycloalkyl group optionally substituted by a carboxy group,
by a phenyl group which may be substituted by a fluorine, chlorine, bromine or iodine atom, by a $C_{1-3}$-alkyl, carboxy-$C_{1-3}$-alkyl, $C_{1-3}$-alkoxy or carboxy group,
by an amino, $C_{1-5}$-alkylamino, $C_{3-7}$-cycloalkylamino, phenylamino or heteroarylamino group, each of which may additionally be substituted at the amino nitrogen atom by a $C_{1-5}$-alkyl, $C_{5-7}$-cycloalkyl, phenyl-$C_{1-3}$-alkyl, carboxy-$C_{1-3}$-alkyl, 2-[di-($C_{1-3}$-alkyl)-amino]-ethyl, 3-[di-($C_{1-3}$-alkyl)-amino]-propyl, di-($C_{1-3}$-alkyl)-amino, 2-(N-carboxy-$C_{1-3}$-alkyl-$C_{1-3}$-alkylamino)-ethyl, 3-(N-carboxy-$C_{1-3}$-alkyl-$C_{1-3}$-alkylamino)-propyl or N-carboxy-$C_{1-3}$-alkyl-$C_{1-3}$-alkylamino, pyrrolidinyl or piperidinyl group,
by a pyrrolyl, thienyl, imidazolyl, pyrazolyl, thiazolyl, pyridinyl, pyrimidinyl, pyrazinyl or pyridazinyl group optionally substituted by a $C_{1-3}$-alkyl group, onto which a phenyl ring may be fused via two adjacent carbon atoms,
by a $C_{3-6}$-cycloalkyleneimino, $C_{5-8}$-bicycloalkyleneimino, morpholino, piperazino, dihydropyrazolo, tetrahydropyrazolo, tetrahydroisoxazolo, tetrahydropyrazinyl or tetrahydropyridazinyl group optionally substituted by a $C_{1-3}$-alkyl or carboxy-$C_{1-3}$-alkyl group or
by a pyrrolidino group, whilst the abovementioned pyrrolidino group is substituted by a hydroxy, hydroxy-$C_{1-3}$-alkyl, amino, carboxy, carboxy-$C_{1-3}$-alkyl, carboxy-$C_{1-3}$-alkoxy-$C_{1-3}$-alkyl, carboxy-$C_{1-3}$-alkylamino-$C_{1-3}$-alkyl or carboxy-$C_{1-3}$-alkylaminocarbonyl-$C_{1-3}$-alkyl group, $R_3$ denotes
a hydrogen atom or a formyl group,
an amino, $C_{1-3}$-alkylamino, di-($C_{1-3}$-alkyl)-amino, $C_{1-4}$-alkanoylamino or N—($C_{1-4}$-alkanoyl)-$C_{1-3}$-alkylamino group, a $C_{1-3}$-alkyl group optionally substituted by a hydroxy, $C_{1-3}$-alkoxy, carboxy, carboxy-$C_{1-3}$-alkoxy, carboxy-$C_{1-3}$-alkylamino, N—($C_{1-3}$-alkyl)-carboxy-$C_{1-3}$-alkylamino or carboxy-$C_{1-3}$-alkylaminocarbonyl group, a $C_{2-3}$-alkenyl group substituted by a carboxy or carboxy-$C_{1-3}$-alkylaminocarbonyl group or a carbimino group optionally substituted at the carbon atom by a $C_{1-3}$-alkyl group, which is substituted at the imino nitrogen atom by a carboxy-$C_{1-3}$-alkoxy or aminocarbonylamino group, or $R_2$ and $R_3$ together denote a —CO—O—CH$_2$ or —CO—O—CH$_2$CH$_2$— group and $R_4$ denotes a hydrogen, fluorine, chlorine, bromine or iodine atom or a $C_{1-3}$-alkyl, $C_{3-7}$-cycloalkyl or $C_{1-3}$-alkoxy group, or Ar also denotes a heteroaryl group which may be substituted by the abovementioned groups $R_2$ to $R_4$, X denotes an oxygen or sulphur atom, a methylene group optionally substituted by one or two $C_{1-3}$-alkyl groups, a carbonyl, sulphinyl, sulphonyl, imino, N—($C_{1-3}$-alkyl)-imino or N-(carboxy-$C_{1-3}$-alkyl)-imino group, whilst the alkyl moiety of the N—($C_{1-3}$-alkyl)-imino group in 2- or 3-position may additionally be substituted by an amino, $C_{1-3}$-alkylamino, di-($C_{1-3}$-alkyl)-amino, $C_{1-4}$-alkanoylamino or N—($C_{1-4}$-alkanoyl)-$C_{1-3}$-alkylamino group, and Y denotes a cyclohexyl group substituted by an amino group or a phenyl or heteroaryl group substituted by the group $R_5$, whilst the above-mentioned phenyl group may be substituted in each case by a fluorine, chlorine, bromine or iodine atom or by a $C_{1-3}$-alkyl or $C_{1-3}$-alkoxy group and the above-mentioned heteroaryl group may be substituted by a $C_{1-3}$-alkyl group and $R_5$ denotes a hydrogen atom, a cyano group or an amino, amino-$C_{1-3}$-alkyl, amidino, guanidino or guanidino-$C_{1-3}$-alkyl group optionally substituted by a group which can be cleaved in vivo, the prodrugs thereof, the tautomers, the stereoisomers, the mixtures thereof and the salts thereof, but particularly those wherein A denotes a vinylene group optionally substituted by a chlorine, bromine or iodine atom, or an ethylene or ethynylene group, $R_1$ denotes a hydrogen atom or a $C_{1-3}$-alkyl group, Ar denotes a pyridyl or thienyl group substituted by a benzoyl group, a bromofuranyl group substituted by a pyrrolidinocarbonyl group or a phenyl group substituted by the groups $R_2$ to $R_4$, whilst $R_2$ denotes a phenyl or phenoxy group, a $C_{1-3}$-alkyl group which may be substituted by a phenyl, phenylamino, N—($C_{1-3}$-alkyl)-phenylamino or N—($C_{1-3}$-alkanoyl)-phenylamino group, a carboxy or $C_{1-3}$-alkoxycarbonyl group, a benzoyl or phenylsulphonyl group wherein in each case the phenyl moiety may additionally be substituted by a fluorine, chlorine or bromine atom, by a methyl, methoxy, carboxy or $C_{1-3}$-alkoxycarbonyl group, whilst in the above-mentioned benzoyl groups the oxygen atom may additionally be replaced by a carboxy-$C_{1-3}$-alkoxyimino or $C_{1-3}$-alkoxycarbonyl-$C_{1-3}$-alkoxyimino group, a $C_{1-5}$-alkylamino group which may be substituted in the alkyl moiety by a phenyl, carboxy, $C_{1-3}$-alkoxycarbonyl, carboxy-$C_{1-3}$-alkylaminocarbonyl, $C_{1-3}$-alkoxycarbonyl-$C_{1-3}$-alkylaminocarbonyl, N—($C_{1-3}$-alkyl)-carboxy-$C_{1-3}$-alkylaminocarbonyl or N—($C_{1-3}$-alkyl)-$C_{1-3}$-alkoxycarbonyl-$C_{1-3}$-alkylaminocarbonyl group, or a $C_{3-7}$-cycloalkylamino group, whilst the above-mentioned groups may each additionally be substituted at the amino nitrogen atom by a $C_{3-7}$-cycloalkanoyl, benzoyl or phenylsulphonyl group, by a carboxy-$C_{1-3}$-alkylcarbonyl or $C_{1-3}$-alkoxycarbonyl-$C_{1-3}$-alkylcarbonyl group wherein the alkyl moiety of the alkylcarbonyl group is substituted in each case by an amino or trifluoroacetylamino group, by a $C_{2-4}$-alkanoyl group, which may be substituted in the alkanoyl moiety by an amino, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$-alkylaminocarbonyl, $C_{1-3}$-alkoxycarbonyl-$C_{1-3}$-alkylaminocarbonyl, N—($C_{1-3}$-alkyl)-carboxy-$C_{1-3}$-alkylaminocarbonyl or N—($C_{1-3}$-alkyl)-$C_{1-3}$-alkoxycarbonyl-$C_{1-3}$-alkylaminocarbonyl group, by a carboxy-$C_{1-2}$-alkylaminocarbonyl, $C_{1-3}$-alkoxycarbonyl-$C_{1-2}$-alkylaminocarbonyl, carboxy-$C_{1-3}$-alkylaminocarbonyl-$C_{1-2}$-alkylaminocarbonyl or $C_{1-3}$-alkoxycarbonyl-$C_{1-3}$-alkylaminocarbonyl-$C_{1-2}$-alkylaminocarbonyl group, a formyl, pyridylcarbonyl, thienylcarbonyl, imidazolylcarbonyl, 1-methyl-imidazolylcarbonyl, thiazolylcarbonyl or indolylcarbonyl group, a benzimidazol-1-yl, benzimidazol-1-yl-methyl or 5-oxo4,5-dihydro-pyrazol-3-yl group optionally substituted by 1 or 2 methyl groups, a pyrazol-1-yl group substituted by a phenyl group, by a phenyl group and a $C_{1-4}$-alkyl group or by one or two $C_{1-4}$-alkyl groups wherein an alkyl substituent may at the same time be substituted by a carboxy or $C_{1-3}$-alkoxycarbonyl group, or a carbonyl group which is substituted
by a $C_{1-5}$-alkyl group optionally substituted by a carboxy or $C_{1-3}$-alkoxycarbonyl group,
by a $C_{3-7}$-cycloalkyl group,
by an amino or $C_{1-5}$-alkylamino group, which are in each case substituted at the amino nitrogen atom by a $C_{1-3}$-alkyl group which may be substituted by a $C_{3-7}$-cycloalkyl, phenyl, pyrrolidinyl or pyridinyl group or in the 2 or 3 position by a di-($C_{1-3}$-alkyl)-amino group, or by a di-($C_{1-3}$-alkyl)-amino group,
by a carboxy-$C_{1-3}$-alkylamino or $C_{1-3}$-alkoxycarbonyl-$C_{1-3}$-alkylamino group which is in each case substituted at the amino nitrogen atom by a pyrazolyl group optionally substituted by a $C_{1-3}$-alkyl group,
by a 3- to 7-membered cycloalkyleneimino group which may be substituted by one or two $C_{1-3}$-alkyl groups, whilst the above-mentioned pyrrolidino groups optionally substituted by a methyl group may additionally be substituted by a hydroxymethyl, carboxy, $C_{1-3}$-alkoxycarbonyl, carboxy-$C_{1-3}$-alkyl, $C_{1-3}$-alkoxycarbonyl-$C_{1-3}$-alkyl, carboxy-$C_{1-3}$- alkyloxy-$C_{1-3}$-alkyl,
$C_{1-3}$-alkoxycarbonyl-$C_{1-3}$-alkyloxy-$C_{1-3}$-alkyl,
carboxy-$C_{1-3}$-alkylamino-$C_{1-3}$-alkyl, N—($C_{1-3}$-alkyl)-carboxy-$C_{1-3}$-alkylamino-$C_{1-3}$-alkyl,
$C_{1-3}$-alkoxycarbonyl-$C_{1-3}$-alkylamino-$C_{1-3}$-alkyl, N—($C_{1-3}$-alkyl)-carboxy-$C_{1-3}$-alkylamino-$C_{1-3}$-alkyl or N—($C_{1-3}$-alkyl)-$C_{1-3}$-alkoxycarbonyl-$C_{1-3}$-alkylamino-$C_{1-3}$-alkyl group, by a morpholino, piperazino, 4-methyl-piperazino, piperazino-$C_{1-3}$-alkyl, dihydropyrazolo, tetrahydropyrazolo, tetrahydroisoxazolo or 7-azabicycloheptyl group or by an N—($C_{1-3}$-alkyl)-phenyl or N—($C_{1-3}$-alkyl)-pyridylamino group optionally substituted in the alkyl moiety by a carboxy or $C_{1-3}$-alkoxycarbonyl group, $R_3$ denotes
a hydrogen, fluorine, chlorine or bromine atom,
a hydroxy, $C_{1-3}$-alkoxy, trifluoromethyl, amino or $C_{2-3}$-alkanoylamino group,
a $C_{1-3}$-alkyl group which may be substituted by a hydroxy, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$-alkylaminocarbonyl, $C_{1-3}$-alkoxycarbonyl-$C_{1-3}$-alkylaminocarbonyl, N—($C_{1-3}$-alkyl)-carboxy-$C_{1-3}$-alkylaminocarbonyl or N—($C_{1-3}$-alkyl)-$C_{1-3}$-alkoxycarbonyl-$C_{1-3}$-alkylaminocarbonyl group,
a $C_{1-3}$-alkyl group which is substituted by a carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or $C_{1-3}$-alkoxycarbonyl-$C_{1-3}$-alkylaminocarbonyl group,
a $C_{2-3}$-alkenyl group substituted by a carboxy or $C_{1-3}$-alkoxycarbonyl group or a carbimino group optionally substituted at the carbon atom by a $C_{1-3}$-alkyl group, which is substituted at the imino nitrogen atom by a carboxy-$C_{1-3}$-alkoxy, $C_{1-3}$-alkoxycarbonyl-$C_{1-3}$-alkoxy or aminocarbonylamino group,
or $R_2$ and $R_3$ together denote a —CO—O—$CH_2$-group and $R_4$ denotes a hydrogen, fluorine, chlorine or bromine atom, a $C_{1-3}$-alkyl or trifluoromethyl group, X denotes an oxygen or sulphur atom or an —NH-group optionally substituted by a $C_{1-3}$-alkyl group and Y denotes a cyclohexyl group substituted by an amino group, a phenylene or pyridinylene group substituted by an amidino group, which may be substituted by a benzoyl or $C_{1-8}$-alkoxycarbonyl group, whilst the above-mentioned phenylene group may be substituted by a methyl or methoxy group and the above-mentioned pyridinylene group may be substituted by a methyl group, the tautomers, the stereoisomers, the mixtures thereof and the salts thereof.

Particularly preferred compounds of the present invention are the compounds of general formula

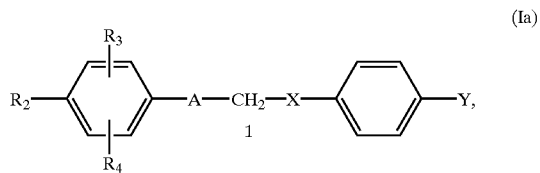

(Ia)

wherein
A denotes an ethylene or ethynylene group,
X denotes an oxygen atom or an imino group optionally substituted by a methyl group,
$R_2$ denotes
a $C_{1-4}$-alkylcarbonylamino or $C_{3-5}$-cycloalkylcarbonylamino group, which is substituted in each case at the amino nitrogen atom by a carboxy-$C_{1-2}$-alkyl, $C_{1-3}$-alkoxycarbonyl-$C_{1-2}$-alkyl, carboxy-$C_{1-2}$-alkylaminocarbonyl-$C_{1-2}$-alkyl or $C_3$-alkoxycarbonyl-$C_{1-2}$-alkylaminocarbonyl-$C_{1-2}$-alkyl group,
a $C_{1-4}$-alkylamino or $C_{3-5}$-cycloalkylamino group, which is substituted in each case at the amino nitrogen atom by a carboxy-$C_{1-3}$-alkylcarbonyl, $C_{1-3}$-alkoxycarbonyl-$C_3$-alkylcarbonyl, carboxy-$C_{1-2}$-alkylaminocarbonyl-$C_{1-2}$-alkylcarbonyl, $C_{1-3}$-alkoxy-carbonyl-$C_{1-2}$-alkylaminocarbonyl-$C_{1-2}$-alkylcarbonyl, carboxy-$C_{1-2}$-alkylaminocarbonyl, $C_{1-3}$-alkoxycarbonyl-$C_{1-2}$-alkylaminocarbonyl, carboxy-$C_{1-2}$-alkylaminocarbonyl-$C_{1-2}$-alkylaminocarbonyl or $C_{1-3}$-alkoxycarbonyl-$C_{1-2}$-alkylaminocarbonyl-$C_{1-2}$-alkylaminocarbonyl group optionally substituted in the alkyl moiety by an amino group, or by a carboxymethyloxymethylcarbonyl, $C_{1-3}$-alkoxycarbonyl-methyloxymethylcarbonyl, carboxymethylaminomethylcarbonyl, $C_{1-3}$-alkoxycarbonyl-methylaminomethylcarbonyl, N-methyl-carboxymethylaminomethylcarbonyl, N-methyl-$C_{1-3}$-alkoxycarbonyl-carboxymethylaminomethylcarbonyl, aminomethylcarbonyl, 2-amino-ethylcarbonyl, carboxy-$C_{1-2}$-alkylaminocarbonylmethyloxymethylcarbonyl, $C_{1-3}$-alkoxycarbonyl-$C_{1-2}$-alkylaminocarbonylmethyloxymethylcarbonyl, carboxy-$C_{1-2}$-alkylaminocarbonylmethylaminomethylcarbonyl, $C_{1-3}$-alkoxycarbonyl-$C_{1-2}$-alkylaminocarbonylmethylaminomethylcarbonyl, N-methyl-carboxy-$C_{1-2}$-alkylaminocarbonylmethylaminomethylcarbonyl or N-methyl-$C_{1-3}$-alkoxycarbonyl-$C_{1-2}$-alkylaminocarbonylmethylaminomethylcarbonyl group, or
a carbonyl group which is substituted
by a cyclopentyl group,
by a $C_{3-5}$-alkyl group which may additionally be substituted by a carboxy or $C_{1-3}$-alkoxycarbonyl group,
by a $C_{1-4}$-alkylamino, phenylamino or pyridylamino group substituted at the amino nitrogen atom by a $C_{1-4}$-alkyl, carboxy-$C_{1-3}$-alkyl or $C_{1-3}$-alkoxycarbonyl-$C_{1-3}$-alkyl group,
by a pyrrolidino group substituted by a methyl, hydroxymethyl, amino, carboxy, $C_{1-3}$-alkoxycarbonyl, carboxy-$C_{1-2}$-alkyl, $C_{1-3}$- alkoxycarbonyl-$C_{1-2}$-alkyl, carboxymethyloxymethyl, $C_{1-3}$-alkoxycarbonylmethyloxymethyl, carboxymethylaminomethyl, $C_{1-3}$-alkoxycarbonyl-methylaminomethyl, carboxymethylaminocarbonylmethyloxymethyl or $C_{1-3}$-alkoxycarbonylmethylaminocarbonylmethyloxymethyl group, $R_3$ denotes
  a hydrogen, fluorine, chlorine or bromine atom or a trifluoromethyl group,
  a $C_{1-2}$-alkyl group optionally substituted by a hydroxy, carboxy, $C_{1-3}$-alkoxycarbonyl, carboxymethyloxy, $C_{1-3}$-alkoxycarbonyl-methyloxy, carboxymethylamino, N-methyl-carboxymethylamino, $C_{1-3}$-alkoxycarbonylmethylamino, N-methyl-$C_{1-3}$-alkoxycarbonylmethylamino, carboxymethylaminocarbonyl or $C_{1-3}$-alkoxycarbonylmethylaminocarbonyl group,
  a vinyl group substituted by a carboxy or $C_{1-3}$-alkoxycarbonyl group, $R_4$ denotes a hydrogen, fluorine, chlorine or bromine atom, a methyl, ethyl or trifluoromethyl group and Y denotes an amidino group optionally substituted by a $C_{1-8}$-alkoxycarbonyl or benzoyl group, the tautomers, the stereoisomers, the mixtures thereof and the salts thereof.

Most particularly preferred compounds of the present invention are the compounds of general formula Ia wherein A denotes an ethylene or ethynylene group, X denotes an imino group, $R_2$ denotes
  a $C_{1-4}$-alkylaminocarbonyl group, which is substituted in each case at the amino nitrogen atom by a carboxy-$C_{1-2}$-alkyl or $C_{1-3}$-alkoxycarbonyl-$C_{1-2}$-alkyl group,
  a $C_{1-4}$-alkylamino group which is substituted at the amino nitrogen atom by a carboxy-$C_{1-3}$-alkylcarbonyl, $C_{1-3}$-alkoxycarbonyl-$C_{1-3}$-alkylcarbonyl, carboxy-$C_{1-2}$-alkylaminocarbonyl or $C_{1-3}$-alkoxycarbonyl-$C_{1-2}$-alkylaminocarbonyl group, or
  a carbonyl group which is substituted
    by a $C_{3-5}$-alkyl group which may additionally be substituted by a carboxy or $C_{1-3}$-alkoxycarbonyl group,
    by a $C_{1-4}$-alkylamino or pyridylamino group substituted at the amino nitrogen atom by a carboxy-$C_{1-3}$-alkyl or $C_{1-3}$-alkoxycarbonyl-$C_{1-3}$-alkyl group,
    by a pyrrolidino group optionally substituted by a methyl group, $R_3$ denotes a $C_{1-2}$-alkyl group optionally substituted by a carboxy or $C_{1-3}$-alkoxycarbonyl group, $R_4$ denotes a hydrogen atom or a methyl group and Y denotes an amidino group optionally substituted by a $C_{1-8}$-alkoxycarbonyl or benzoyl group, the tautomers, the stereoisomers, the mixtures thereof and the salts thereof.

The following are mentioned as examples of particularly preferred compounds:

(a) rac-4-{3-[5-ethoxycarbonylmethyl-2-methyl-4-(2-methyl-pyrrolidinocarbonyl)-phenyl]-propargylamino}benzamidine, (b) rac-4-{3-[2,5-dimethyl-4-(2-methyl-pyrrolidinocarbonyl)-phenyl]-propargylamino}benzamidine, (c) 4-[3-(2,5-dimethyl-4-isopropylcarbonyl-phenyl)propargyl-amino]benzamidine, (d) 4-{3-[2,5-dimethyl-4-(N-methyl-N-pyridin-2-yl-aminocarbonyl)-phenyl]propargylamino}benzamidine, (e) 4-{3-[2,5-dimethyl-4-(N-methyl-N-pyridin-2-yl-aminocarbonyl)-phenyl]prop-1-ylamino}benzamidine, (f) 4-[3-(3-methyl-4-pyrrolidinocarbonyl-phenyl)-propargyl-amino]-benzamidine, (g) 4-{3-[2,5-dimethyl-4-(N-(2-methoxycarbonyl-ethyl)-N-ethyl-carbonylamino)-phenyl]-propargylamino}benzamidine, (h) 4-{3-[2,5-dimethyl-4-(N-isopropyl-N-hydroxycarbonylmethyl-aminocarbonyl-amino)-phenyl]-propargylamino}-benzamidine and (i) 4-{3-[2,5-dimethyl-4-(N-isopropyl-N-hydroxycarbonylmethyl-carbonyl-amino)-phenyl]-propargylamino}-benzamidine and the salts thereof.

According to the invention, the compounds of general formula I are prepared by known methods, e.g. by the following methods:

a. reacting a compound of general formula

$$Ar—Z_1, \quad (II)$$

wherein
  Ar is as hereinbefore defined and
  $Z_1$ denotes a leaving group such as a halogen atom or a sulphonyloxy group, e.g. a chlorine, bromine or iodine atom or a trifluoromethylsulphonyloxy group, with a compound of general formula

$$H—A'—HCR_1—X—Y', \quad (III)$$

wherein
  $R_1$ and X are as hereinbefore defined,
  Y' has the meanings given for Y hereinbefore with the proviso that any amino or imino group present is protected by a conventional protecting group, and
  A' denotes an ethynyl group, optionally followed by catalytic hydrogenation and/or cleaving of any protecting group used.

The reaction is preferably carried out in a solvent such as acetonitrile, diethylether, tetrahydrofuran or dimethylformamide in the presence of a palladium catalyst such as bis(triphenylphosphine)-palladium(II)chloride or tetrakis-(triphenylphosphine)-palladium(0) in the presence of a tertiary or inorganic base such as triethylamine, N-isopropyl-diethylamine, potassium-tert-butoxide, sodium carbonate or caesium carbonate and in the presence of a reaction accelerator such as a copper halide, e.g. copper(I) iodide and at temperatures between 20 and 120° C., preferably at temperatures between 40 and 100° C. (cf. also K. Sonogashira, Comprehensive Organic Synthesis, Vol. 3, page 52ff., Pergamon Press, Oxford 1991).

The protecting groups which may be used and their removal are described hereinafter (cf. also T. Greene, Protective Groups in Organic Synthesis, Wiley Interscience, New York 1981).

b. In order to prepare a compound of general formula I wherein the Ar—A group contains a carboxy group and $R_5$ is as hereinbefore defined or the Ar—A group is as hereinbefore defined and $R_5$ denotes an amino, amino-$C_{1-3}$-alkyl, amidino or guanidino group or the Ar—A group contains a carboxy group and $R_5$ denotes an amino, amino-$C_{1-3}$-alkyl, amidino or guanidino group:

converting a compound of general formula

$$Ar'—A—HCR_1—X—Y'', \qquad (IV)$$

wherein

A, $R_1$, and X are as hereinbefore defined,

Ar' and Y'' have the meanings given for Ar and Y hereinbefore, with the proviso that Ar' contains a group which can be converted into a carboxy group by hydrolysis, treatment with an acid or base, thermolysis or hydrogenolysis and Y'' has the meanings given for Y hereinbefore or Ar' has the meanings given for Ar hereinbefore and Y'' contains a group which can be converted into an amino, amino-$C_{1-3}$-alkyl, amidino or guanidino group by hydrolysis, treatment with an acid or base, thermolysis or hydrogenolysis, or Ar' contains a group which can be converted into a carboxy group by hydrolysis, treatment with an acid or base, thermolysis or hydrogenolysis and Y'' contains a group which can be converted into an amino, amino-$C_{1-3}$-alkyl, amidino or guanidino group by hydrolysis, treatment with an acid or base, thermolysis or hydrogenolysis, is converted by hydrolysis, treatment with an acid or base, thernolysis or hydrogenolysis into a compound of general formula I wherein the Ar—A group contains a carboxy group and $R_5$ is as hereinbefore defined or the Ar—A group is as hereinbefore defined and $R_5$ denotes an amino, amino-$C_{1-3}$-alkyl, amidino or guanidino group or the Ar—A group contains a carboxy group and $R_5$ denotes an amino, amino-$C_{1-3}$-alkyl, amidino or guanidino group.

An example of a group which can be converted into a carboxy group might be a carboxyl group protected by a protecting group, for example, such as the functional derivatives thereof, e.g. the unsubstituted or substituted amides, esters, thioesters, trimethylsilylesters, orthoesters or iminoesters thereof which are conveniently converted into a carboxyl group by hydrolysis, the esters thereof with tertiary alcohols, e.g. the tert-butylester, which are conveniently converted into a carboxyl group by treating with an acid or thermolysis, and the esters thereof with aralkanols, e.g. the benzyl ester thereof, which are conveniently converted into a carboxyl group by hydrogenolysis.

The hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between –10 and 120° C., e.g. at temperatures between ambient temperature and the boiling temperature of the reaction mixture.

If a compound of general formula IV contains the tert-butyl or tert-butyloxycarbonyl group, for example, this may also be cleaved by treating with an acid such as trifluoroacetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethylether, tetrahydrofuran or dioxane, preferably at temperatures between –10 and 120° C., e.g. at temperatures between 0 and 60° C., or also thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

If a compound of general formula IV contains the benzyloxy or benzyloxycarbonyl group, for example, these may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of 1 to 5 bar.

c. In order to prepare a compound of general formula I wherein $R_5$ denotes an amidino group:

reacting a compound of general formula

$$Ar—A—HCR_1—X—Y'', \qquad (V)$$

optionally formed in the reaction mixture wherein

A, Ar, $R_1$ and X are as hereinbefore defined and

Y'' denotes one of the groups mentioned for Y hereinbefore with the proviso that $R_5$ denotes a $Z_1$—(HN=)C-group wherein $Z_1$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an ammonium salt such as diammonium carbonate or ammonium acetate.

The reaction is conveniently carried out in a solvent such as methanol, ethanol, n-propanol, tetrahydrofuran or dioxane at temperatures between 0 and 150° C., preferably at temperatures between 0 and 80° C.

A compound of general formula V is obtained for example by reacting a corresponding cyano compound with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium tetrafluoroborate in a solvent such as methylene chloride, tetrahydrofuran or dioxane at temperatures between 0 and 50° C., but preferably at 20° C., or a corresponding nitrile with hydrogen sulphide, conveniently in a solvent such as pyridine or dimethylformamide and in the presence of a base such as triethylamine and subsequently alkylating the thioamide formed with a corresponding alkyl or aralkyl halide.

In the reaction described above, a hydrogen halide may at the same time be added to an electron-rich or electron-poor triple bond.

d) In order to prepare a compound of general formula I wherein $R_5$ denotes an amidino group which is substituted by a hydroxy group:

reacting a compound of general formula

$$Ar—A—HCR_1—X—Y'', \qquad (V)$$

optionally formed in the reaction mixture wherein

A, Ar, $R_1$ and X are as hereinbefore defined and

Y'' denotes one of the groups mentioned for Y hereinbefore with the proviso that $R_5$ denotes a $Z_1$—(HN=)C group wherein $Z_1$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with hydroxylamine or the salts thereof.

The reaction is conveniently carried out in a solvent such as methanol, ethanol, n-propanol, water, methanol/water, tetrahydrofuran, tetrahydrofuran/water, dioxane or dioxane/water in the presence of a base such as triethylamine at temperatures between 0 and 150° C., preferably at temperatures between 0 and 80° C.

e. In order to prepare a compound of general formula I wherein X denotes an oxygen or sulphur atom, a carbonyl, imino or N—($C_{1-3}$-alkyl)-imino group:

reacting a compound of general formula I $$\text{Ar—A—HCR}_1\text{—Z}_2, \quad \text{(VI)}$$

wherein

A, Ar and $R_1$ are as hereinbefore defined and $Z_2$ denotes a leaving group such as a halogen atom or a sulphonyloxy group, e.g. a bromine or iodine atom, a methanesulphonyloxy or p-toluenesulphonyloxy group, with a compound of general formula $$\text{U—Y,} \quad \text{(VII)}$$

wherein

Y is as hereinbefore defined and

U denotes a hydroxy, mercapto, hydroxycarbonyl, imino or N—($C_{1-3}$-alkyl)-imino group.

The reaction is preferably carried out in a solvent such as methanol, ethanol, methylene chloride, tetrahydrofuran, toluene, dioxane, dimethylsulphoxide or dimethylformamide optionally in the presence of an inorganic or a tertiary organic base, preferably at temperatures between 20° C. and the boiling temperature of the solvent used.

f. In order to prepare a compound of general formula I wherein Ar and/or Y contain a group which can be cleaved in vivo:

reacting a compound of general formula $$\text{Ar''—A—HCR}_1\text{—X—Y''',} \quad \text{(VIII)}$$

wherein

A, $R_1$, and X are as hereinbefore defined,

Ar'' and Y''' have the meanings given for Ar and Y hereinbefore, with the proviso that Ar'' contains a carboxy group and Y''' has the meanings given for Y hereinbefore or Ar'' has the meanings given for Ar hereinbefore and Y''' contains an amino, amino-$C_{1-3}$-alkyl, amidino or guanidino group or Ar'' contains a carboxy group and Y''' contains a group which can be converted [into] an amino, amino-$C_{1-3}$-alkyl, amidino or guanidino group, with a compound of general formula $$Z_3\text{—R}_7, \quad \text{(IX)}$$

wherein $R_7$ denotes a $C_{1-8}$-alkoxycarbonyl group, an $R_a$—CO—O—($R_bCR_c$)-group or the acyl group of one of the groups which can be cleaved in vivo as mentioned hereinbefore, whilst $R_a$ to $R_c$ are as hereinbefore defined, and $Z_3$ denotes a nucleofugic leaving group such as a halogen atom, e.g. a chlorine, bromine or iodine atom, or a p-nitrophenyl group or, if Ar'' contains a carboxy group, Z may also denote a hydroxy group.

The reaction is preferably carried out in a solvent such as methanol, ethanol, methylene chloride, tetrahydrofuran, toluene, dioxane, dimethylsulphoxide or dimethylformamide optionally in the presence of an acid-activating or dehydrating agent and optionally in the presence of an inorganic or a tertiary organic base, preferably at temperatures between 20° C. and the boiling temperature of the solvent used.

With a compound of general formula IX wherein $Z_3$ denotes a nucleofugic leaving group, the reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium tert-butoxide or N-ethyl-diisopropylamine at temperatures between 0 and 60° C.

With a compound of general formula IX wherein $Z_3$ denotes a hydroxy group, the reaction is optionally carried out in a solvent or mixture of solvents such as methylene chloride, dimethylformamide, benzene, toluene, chlorobenzene, tetrahydrofuran, benzene/tetrahydrofuran or dioxane in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium-tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methylmorpholine or triethylamine, conveniently at temperatures between 0 and 150° C., preferably at temperatures between 0 and 100° C.

If in a compound of general formula IX $Z_3$ denotes a hydroxy group, the reaction may also be carried out with one of the reactive derivatives thereof, such as the esters, imidazolides or halides thereof, preferably in a solvent such as methylene chloride or ether and preferably in the presence of a tertiary organic base such as triethylamine, N-ethyl-diisopropylamine or N-methylmorpholine at temperatures between 0 and 150° C., preferably at temperatures between 50 and 100° C.

If according to the invention a compound of general formula I is obtained wherein $R_5$ denotes an amidino group, this may be converted by alkylation with a haloacetic derivative, by subsequent hydrolysis and decarboxylation into a corresponding amidino compound substituted by one or two methyl groups and/or if a compound of general formula I is obtained wherein $R_5$ denotes a hydroxyamidino group, this can be converted by catalytic hydrogenation into a corresponding amidino compound and/or if a compound of general formula I is obtained which contains a double or triple bond, this can be converted by catalytic hydrogenation into a corresponding saturated compound and/or if a compound of general formula I is obtained wherein X denotes a sulphur atom, this can be converted by oxidation into a corresponding sulphinyl or sulphonyl compound and/or if a compound of general formula I is obtained wherein $R_2$ denotes a tetra-hydropyrazolocarbonyl group, this can be converted by oxidation into a corresponding 4,5-dihydropyrazolocarbonyl compound and/or if a compound of general formula I is obtained which contains a carbonyl group, this can be converted by a corresponding oxime into a corresponding oxime compound and/or if a compound of general formula I is obtained which contains a carboxy group, this can be converted by an amine into a corresponding amide.

The subsequent alkylation is conveniently carried out in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methylmorpholine, which may serve as the solvent at the same time, or optionally in the presence of silver carbonate or silver oxide at temperatures between −30 and 100° C., but preferably at temperatures between −10 and 80° C.

The subsequent hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane.

The subsequent decarboxylation is carried out in the presence of an acid as hereinbefore described at temperatures between −10 and 120° C., e.g. at temperatures between ambient temperature and the boiling temperature of the reaction mixture.

The subsequent catalytic hydrogenation is preferably carried out in the presence of a hydrogenation catalyst such as palladium/charcoal and in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of 1 to 5 bar.

The subsequent oxidation is preferably carried out in a solvent or mixture of solvents, e.g. in water, water/pyridine, acetone, methylene chloride, acetic acid, acetic acid/acetic anhydride, dilute sulphuric acid or trifluoroacetic acid, conveniently at temperatures between −80 and 100° C. depending on the oxidising agent used.

In order to prepare a corresponding sulphinyl compound of general formula I the oxidation is conveniently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid optionally in the presence of a weak base such as sodium acetate, with N-bromosuccinimide in ethanol, with tert-butylhypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphuryl chloride in methylene chloride at −70° C., and the resulting thioether-chlorine complex is conveniently hydrolysed with aqueous ethanol.

In order to prepare a sulphonyl compound of general formula I oxidation is carried out starting from a corresponding sulphinyl compound, conveniently with one or more equivalents of the oxidising agent used or starting from a corresponding sulphenyl compound conveniently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

In order to prepare a 4,5-dihydropyrazolocarbonyl compound of general formula I the oxidation may also be carried out using oxygen from the air in one of the above-mentioned solvents at ambient temperature.

The subsequent oxime formation is conveniently carried out in a solvent such as methanol/toluene in the presence of a dehydrating agent such as molecular sieves, preferably at the boiling temperature of the solvent used.

The subsequent amide formation is preferably carried out in a solvent or mixture of solvents such as methylene chloride, dimethylformamide, benzene, toluene, chlorobenzene, tetrahydrofuran, benzene/tetrahydrofuran or dioxane in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium-tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methylmorpholine or triethylamine, conveniently at temperatures between 0 and 150° C., preferably at temperatures between 0 and 100° C.

In the reactions described hereinbefore, any reactive groups present such as hydroxy, carboxy, amino, alkylamino or imino groups may be protected during the reaction by conventional protecting groups which are cleaved again after the reaction (cf. also T. Greene, Protective Groups in Organic Synthesis, Wiley Interscience, New York 1981).

For example, a protecting group for a hydroxy group may be a trimethylsilyl, acetyl, benzoyl, tert-butyl, trityl, benzyl or tetrahydropyranyl group, protecting groups for a carboxy group may be a trimethylsilyl, methyl, ethyl, tertbutyl, benzyl or tetrahydropyranyl group and protecting groups for an amino, alkylamino or imino group may be an acetyl, trifluoroacetyl, benzoyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar.

A tert-butyl or tert-butyloxycarbonyl group is preferably cleaved by treating with an acid such as trifluoroacetic acid or hydrochloric acid, optionally using a solvent such as water, methylene chloride, diethylether, tetrahydrofuran or dioxane.

An allyloxycarbonyl group is cleaved by treating with a catalytic amount of tetrakis-(triphenylphosphine)-palladium (O), preferably in a solvent such as tetrahydrofuran and preferably in the presence of an excess of a base such as morpholine or 1,3-dimedone at temperatures between 0 and 100° C., preferably at ambient temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to IX used as starting materials, some of which are known from the literature, are obtained by methods known from the literature and their preparation is also described in the Examples.

Thus, for example, a compound of general formula II is obtained by reacting a corresponding substituted halobenzene with a corresponding compound, a compound of general formula III is obtained by reacting a corresponding aniline with a propargyl halide and subsequently converting the substituted aniline thus obtained into a compound of general formula III by known methods, e.g. by Pinner reaction, and the compounds of general formulae IV, V, VI and VIII are conveniently obtained by conventional methods as described in the present invention.

Moreover, the compounds of general formula I obtained may be resolved into their enantiomers and/or diastereomers, and the compounds of general formula I obtained which contain a double bond may be resolved into their cis/trans isomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonicacid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the new compounds of general formula I and the salts thereof have valuable properties.

Thus, the compounds of general formula I wherein Y does not contain a cyano group have valuable pharmacological properties, particularly an antithrombotic activity which is preferably based on an effect on thrombin or factor Xa, for example on a prolonging effect on aPTT time and on an inhibitory effect on related serine proteases such as e.g. trypsin, urokinase factor VIIa, factor IX, factor XI and factor XII, and the compounds of general formula I wherein Y contains a cyano group are valuable intermediate products for preparing the compounds of general formula I wherein $R_5$ denotes an optionally substituted aminomethyl, amidino or guanidinomethyl group.

For example, the compounds

A=rac-4-{3-[5-ethoxycarbonylmethyl-2-methyl-4-(2-methyl-pyrrolidinocarbonyl)-phenyl]-propargylamino}benzamidine, B=rac-4-{3-[2,5-dimethyl-4-(2-methyl-pyrrolidinocarbonyl)-phenyl]-propargylamino}benzamidine, C=4-[3-(2,5-dimethyl-4-isopropylcarbonyl-phenyl) propargyl-amino]benzamidine, D=4-{3-[2,5-dimethyl-4-(N-methyl-N-pyridin-2-yl-aminocarbonyl)-phenyl]propargylamino}benzamidine, E=4-{3-[2,5-dimethyl-4-(N-methyl-N-pyridin-2-yl-aminocarbonyl)-phenyl]prop-1-ylamino}benzamidine, F=4-[3-(3-methyl-4-pyrrolidinocarbonyl-phenyl)-propargyl-amino]-benzamidine, G=4-{3-[2,5-dimethyl-4-(N-(2-methoxycarbonyl-ethyl)-N-ethyl-carbonylamino)-phenyl]-propargylamino}benzamidine, H=4-{3-[2,5-dimethyl-4-(N-isopropyl-N-hydroxycarbonylmethyl-aminocarbonyl-amino)-phenyl]-propargylamino}-benzamidine and I=4-{3-[2,5-dimethyl-4-(N-isopropyl-N-hydroxycarbonylmethyl-carbonyl-amino)-phenyl]-propargylamino}-benzamidine were investigated for their effect on prolonging the aPTT time as follows:

Materials:
 plasma, from human citrated blood.
 PTT reagent, Boehringer Mannheim (524298), Calcium solution (0.025 mol/l), Behring Werke, Marburg (ORH 056/57),
 Diethylbarbiturate acetate buffer, Behring Werke, Marburg (ORWH 60/61),
 Biomatic B10 coagulometer, Desaga, Wiesloch.

Method:

The aPTT time was determined using a Biomatic B10 coagulometer made by Messrs. Sarstedt.

The test substance was placed in the test tubes prescribed by the manufacturer with 0.1 ml of human citrated plasma and 0.1 ml of PTT reagent. The mixture was incubated for three minutes at 37° C. The clotting reaction was started by the addition of 0.1 ml of calcium solution. The time is measured using the apparatus from the addition of the calcium solution up to the clotting of the mixture. Mixtures to which 0.1 ml of DBA buffer were added were used as the controls.

According to the definition, a dosage-activity curve was used to determine the effective concentration of the substance at which the aPTT time is double compared with the control.

The Table which follows contains the results found:

| substance | aPTT time ($ED_{200}$ in $\mu M$) |
|---|---|
| A | 0.23 |
| B | 0.45 |
| C | 0.97 |
| D | 0.23 |
| E | 0.69 |
| F | 0.54 |
| G | 0.29 |
| H | 0.20 |
| I | 0.45 |

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/ polyethyleneglycol, propyleneglycol, cetyl stearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE 1 rac-N-tert.butoxycarbonyl-4-{3-[5-ethoxycarbonylmethyl-2-methyl-4-(2-methyl-pyrrolidinocarbonyl)-phenyl]propargyl-amino}benzamidine a. 4-bromo-2,5-dimethylbenzoic acid At $-78°$ C., 100 ml (0.16 mol) of a 1.6 molar n-butyl lithium solution in hexane is added dropwise to a solution of 43.63 g (0.162 mol) of 2,5-dibromo-p-xylene, and stirred for one hour. Then dry carbon dioxide is passed into the solution for 4 hours. It is slowly heated to ambient temperature and stirred for 16 hours. After the slow addition of 210 ml of 2N hydrochloric acid, the phases are separated, the aqueous phase is extracted 2× with 200 ml ether, the combined organic phases are washed with conc. NaCl solution and dried with $Na_2SO_4$. After the solvent has been eliminated in vacuo the crude product is mixed with 200 ml of 2N NaOH and the brown solution obtained is extracted 3× with 100 ml of diethyl ether. The aqueous phase is acidified with conc. HCl and the precipitate which then forms is suction filtered, washed with ice water and dried.

Yield: 34.99 g (94% of theory), $R_f$ value: 0.55 (silica gel; ethyl acetate/petroleum ether= 2:1)

b. 4-bromo-2-ethoxycarbonylmethyl-5-methyl-benzoic acid

A solution of 1.7 ml (14 mmol) of diethyl carbonate and 2.3 g (10 mmol) of 4-bromo-2,5-dimethylbenzoic acid in 15 ml tetrahydrofuran is added dropwise, over 2.5 hours, to a solution cooled to $-78°$ C., prepared from 4.2 ml (30 mmol) of diisopropylamine and 19 ml of a 1.6 molar n-butyl lithium solution in hexane, in 35 ml tetrahydrofuran. Then it is heated to 0° C., poured into 200 ml of 3% $NH_4Cl$ solution, adjusted to pH 6 with acetic acid and extracted with ethyl acetate. The ethyl acetate phase is washed with 14% NaCl solution and dried with $Na_2SO_4$. The solvent is distilled off and the residue remaining is triturated several times in a little diisopropylether/petroleum ether and then dried.

Yield: 1.95 g (65% of theory), $R_f$ value: 0.35 (silica gel; ethyl acetate/petroleum ether= 3:7+1 drop of glacial acetic acid)

c. rac-N-(4-bromo-2-ethoxycarbonylmethyl-5-methyl-benzoyl)-2-methyl-pyrrolidine 2.2 g (6.85 mmol) of O-(benzotriazol-1-yl)-N,N,N',N'-tetramethyluronium tetrafluoroborate, 2.41 ml (13.9 mmol) of N,N-diisopropylethylamine and 0.27 g (2.0 mmol) of 1-hydroxy-1H-benzotriazole are added successively to a solution of 1.9 g (6.31 mmol) of 4-bromo-2-ethoxycarbonylmethyl-5-methyl-benzoic acid in 660 ml of tetrahydrofuran/$H_2O$ (9:1). After 10 minutes' stirring, 0.59 g (6.94 mmol) of rac-2-methyl-pyrrolidine is added, the mixture is stirred for another 19 hours and then diluted with 200 ml of ethyl acetate. The solution obtained is washed with 14% NaCl solution and extracted 2× with ethyl acetate. The combined organic phases are washed with 14% NaCl solution and dried with $Na_2SO_4$. After removal of the solvent, by distillation, and flash chromatography (silica gel; methylene chloride/ethanol=98:2) the desired compound is obtained.

Yield: 2.00 g (86% of theory), $R_f$ value: 0.3 (silica gel; ethyl acetate/petroleum ether= 3:7+1 drop of glacial acetic acid)

$C_{17}H_{22}BrNO_3$ (368.27)

Mass spectrum:

$M^+$=367/369 (bromine isotopes)

$(M+H)^+$=368/370 (bromine isotopes)

$(M-H)^-$=366/368 (bromine isotopes)

d. 4-propargylamino-benzonitrile

A solution of 23.6 g (0.20 mol) of 4-amino-benzonitrile, 16.6 ml (0.22 mol) of propargyl bromide and 38.3 ml (0.22 mol) of diisopropylethylamine is heated to 90° C. in 500 ml of toluene for 27 hours. It is then diluted with ethyl acetate, washed 3× with $H_2O$ and dried over $MgSO_4$. After removal of the solvent by distillation the crude product is purified by flash chromatography (silica gel; ethyl acetate/petroleum ether=20:80 to 75:25).

Yield: 22.9 g (73% of theory), $R_f$ value: 0.38 (silica gel; ethyl acetate/petroleum ether= 3:7)

e. 4-propargylamino-benzamidine

A solution of 5.0 g (32 mmol) of 4-propargylamino-benzonitrile is stirred in 150 ml of ethanol saturated with hydrogen chloride gas first for 3 hours at 0° C., then for 21 hours at ambient temperature. The solvent is eliminated in vacuo at a maximum bath temperature of 30° C. and replaced by 250 ml of absolute ethanol. Then 10.7 g (0.11 mol) of ammonium carbonate are added and the mixture is stirred for 36 hours. The solvent is distilled off, the residue is taken up in 200 ml of methylene chloride/ethanol (94:6), filtered to remove insoluble matter, concentrated and purified by flash chromatography (silica gel; methylene chloride/ethanol=90:10 to 75:25).

Yield: 6.52 g (97% of theory), $R_f$ value: 0.22 (silica gel; methylene chloride/ethanol= 80:20)

f. N-(4-tert-butoxycarbonylamidino-phenyl)-propargylamine

A solution of 1.9 g (9.06 mmol) of 4-propargylamino-benzamidine and 2.35 g (10.8 mmol) of di-tert-butyl pyrocarbonate in 50 ml tetrahydrofuran is slowly combined with 45 ml of 0.2N NaOH at 5° C. and stirred for 2.5 hours at ambient temperature. The solvent is distilled off, the solid residue is washed with $H_2O$ and dried.

Yield: 2.2 g (88% of theory), $R_f$ value: 0.41 (Reversed phase silica gel RP-8; methanol/5% NaCl solution=60:40)

g. rac-N-tert-butoxycarbonyl-4-{3-[5-ethoxycarbonylmethyl-2-methyl-4-(2-methyl-pyrrolidinocarbonyl)-phenyl]propargylamino}benzamidine A solution of 1.00 g (2.72 mmol) of N-(4-bromo-2-ethoxycarbonylmethyl-5-methyl-benzoyl)-2-methyl-pyrrolidine, 1.11 g (4.07 mmol) of N-tert-butoxycarbonyl-4-propargylamino-benzamidine and 10.4 ml (13.5 mmol) of triethylamine in 3.0 ml acetonitrile is stirred for 15 minutes under nitrogen, then combined successively with 0.32 g (0.277 mmol) of tetrakis-(triphenylphosphine)-palladium(0) and 0.11 g (0.578 mmol) of copper(I)iodide and stirred for 1 hour at 90° C. Then the solvent is distilled off and the crude product is purified by flash chromatography (silica gel; methylene chloride/ethanol=99:1 to 95:5).

Yield: 0.18 g (12% of theory), $R_f$ value: 0.3 (silica gel; methylene chloride:ethanol= 19:1)

$C_{32}H_{40}N_4O_5$ (560.69)

Mass spectrum:

$(M+H)^+$=561

$(M-H)^-$=559

EXAMPLE 2 rac-4-{3-[5-ethoxycarbonylmethyl-2-methyl-4-(2-methyl-pyrro-lidinocarbonyl)-phenyl]-propargylamino}benzamidine A solution of 0.36 g (0.642 mmol) of rac-N-tert-butoxycarbonyl-4-{3-[5-ethoxycarbonylmethyl-2-methyl-4-(2-methyl-pyrrolidino-carbonyl)-phenyl]-propargylamino}benzamidine in 20 ml methylene chloride and 3 ml of trifluoroacetic acid is stirred for 4 hours. Then the solvent is distilled off and the crude product is purified by flash chromatography (silica gel; methylene chloride/ethanol=95:5 to 80:20).

Yield: 0.20 g (54% of theory), $R_f$ value: 0.3 (Reversed phase silica gel RP-8; methanol/5% NaCl solution=60:40)

$C_{27}H_{32}N_4O_3 \times CF_3COOH$ (460.58/574.61)

Mass spectrum: $(M+H)^+$=461

EXAMPLE 3 rac-4-{3-[5-hydroxycarbonylmethyl-2-methyl-4-(2-methyl-pyrro-lidinocarbonyl)-phenyl]-propargylamino}benzamidine A mixture of 146 mg (0.254 mmol) of rac-4-{3-[5-ethoxycarbonylmethyl-2-methyl-4-(2-methyl-pyrrolidinocarbonyl)-phenyl]-propargylamino}benzamidine, 3.5 ml of tetrahydrofuran, 2.5 ml of $H_2O$ and 1.3 ml of 1N LiOH solution is stirred for 5 hours. Then 78 mg (1.45 mmol) of ammonium chloride are added, the mixture is stirred for another 16 hours and the solvent is distilled off. The residue is triturated with $H_2O$, suction filtered and washed with a little $H_2O$.

Yield: 35 mg (29% of theory), $R_f$ value: 0.35 (Reversed phase silica gel RP-8; methanol/5% NaCl solution=60:40)

$C_{25}H_{28}N_4O_3 \times HCl$ (432.53/468.99) Mass spectrum:

$(M+H)^+$=433

$(M-H)^-$=431

EXAMPLE 4

4-{3-methyl-4-[(thiazol-2-yl)carbonyl]-phenyl]-propargylamino}benzamidine a. 2-(4-bromo-2-methyl-benzoyl)-thiazole 2.0 g (13 mmol) of 2-trimethylsilylthiazole and 6.1 g (26 mmol) of 4-bromo-2-methyl-benzoic acid chloride are combined while cooling with an ice bath and then are heated to 80° C. for 3 hours. The crude product is taken up in 30 ml of ethyl acetate, washed with $H_2O$, saturated $NaHCO_3$ solution and $H_2O$, dried and purified by flash chromatography (silica gel; methylene chloride).

Yield: 1.4 g (40% of theory), $R_f$ value: 0.65 (silica gel; ethyl acetate/petroleum ether= 20:80)

b. 4-{3-[3-methyl-4-[(thiazole-2-yl)carbonyl]-phenyl]-propargylamino}benzonitrile Prepared analogously to Example 1g from 2-(4-bromo-2-methyl-benzoyl)-thiazole, 4-propargylamino-benzonitrile, tetrakis(triphenylphosphine)palladium(0), copper(I)iodide and triethylamine in acetonitrile.

Yield: 72% of theory, $R_f$ value: 0.43 (silica gel; ethyl acetate/petroleum ether= 20:80)

c. 4-{3-[3-methyl-4-[(thiazole-2-yl)carbonyl]-phenyl]-propargylamino}benzamidine 0.7 g (2 mmol) of 4-{3-[3-methyl-4-[(thiazole-2-yl)carbonyl]-phenyl]-propargylamino}benzonitrile is stirred in 50 ml of ethanol saturated with hydrogen chloride gas first for 2 hours at 0° C., then for 6 hours at ambient temperature. The solvent is eliminated in vacuo at a maximum bath temperature of 30° C. and replaced with 50 ml of absolute ethanol. 1.4 g of ammonium carbonate are added and the mixture is stirred for 16 hours. Then the solvent is distilled off and the residue obtained is purified by flash chromatography (silica gel; methylene chloride/ethanol=98:2 to 80:20).

Yield: 0.7 g (88% of theory), $R_f$ value: 0.31 (silica gel; ethyl acetate/ethanol/ammonia= 90:10:1)

$C_{21}H_{18}N_4OS \times HCl$ (374.47/410.93)

Mass spectrum: $(M+H)^+=375$

EXAMPLE 5

4-[3-(4-biphenyl)-propargylamino]benzamidine a. 4-[3-(4-biphenyl)-propargylamino]benzonitrile Prepared analogously to Example 1g from 4-bromobiphenyl, 4-propargylaminobenzonitrile, tetrakis(triphenylphosphine)palladium(0), copper(I)iodide and triethylamine in acetonitrile.

Yield: 29% of theory, $R_f$ value: 0.48 (silica gel; ethyl acetate/petroleum ether= 25:75)

b. 4-[3-(4-biphenyl)-propargylamino]benzamidine

Hydrogen sulphide is piped into a solution of 0.50 g (1.6 mmol) of 4-[3-(4-biphenyl)-propargylamino]benzonitrile and 0.78 ml of (5.6 mmol) of triethylamine in 25 ml of absolute pyridine until no more starting product can be detected by thin layer chromatography. Then the solvent is distilled off, the residue obtained is taken up in methylene chloride and washed with 2N HCl and $H_2O$. The organic phase is dried and the solvent is distilled off. The residue is taken up in 25 ml of acetone and combined with 2.0 ml (32 mmol) of methyl iodide. After 20 hours the volatile constituents are distilled off, the crude product is taken up in 35 ml of ethanol and 15 ml of methylene chloride and combined with 2.8 g (36 mmol) of ammonium acetate. The reaction mixture is stirred for 8 hours at 40° C. and 60 hours at ambient temperature, concentrated in vacuo and purified by flash chromatography (silica gel; methylene chloride/ethanol=98:2 to 80:20).

Yield: 0.57 g (78% of theory), $R_f$ value: 0.21 (silica gel; methylene chloride/ethanol= 80:20)

$C_{22}H_{19}N_3 \times HI$ (325.41/453.32)

Mass spectrum: $(M+H)^+=326$

EXAMPLE 6

4-{3-[3-(2-methyl-benzimidazol-1-yl-methyl)-phenyl]-propargylamino}benzamidine a. 1-(3-bromobenzyl)-2-methylbenzimidazole First 1.23 g (11 mmol) of potassium-tert-butoxide and after 45 minutes 2.62 g (10.5 mmol) of 3-bromo-benzylbromide are added to a solution of 1.32 g (10 mmol) of 2-methyl-benzimidazole in 10 ml of absolute dimethylsulphoxide and the reaction mixture is stirred for 4 hours. The mixture is then diluted with ethyl acetate, washed 3× with 14% NaCl solution, dried, concentrated and purified by flash chromatography (silica gel; petroleum ether/ethyl acetate=9:1 to ethyl acetate).

Yield: 2.4 g (80% of theory), $C_{15}H_{13}BrN_2$ (301.19)

Mass spectrum: $M^+=300/302$ (bromine isotopes)

b. 4-{3-[3-(2-methylbenzimidazole-1-yl-methyl-phenyl]-propargylamino}benzamidine Prepared analogously to Example 1g from 1-(3-bromobenzyl)-2-methyl-benzimidazole, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group with trifluoroacetic acid analogously to Example 2.

Yield: 55% of theory, $R_f$ value: 0.13 (silica gel; methylene chloride/ethanol= 80:20)

$C_{25}H_{23}N_5 \times CF_3COOH$ (393.49/507.51)

Mass spectrum:

$(M+H)^+=394$ $(M+2H)^{++}=197.6$

EXAMPLE 7

4-{3-[3-methyl-4-(2-methyl-benzimidazole-1-yl)-phenyl]-propargylamino}benzamidine a. N-(2-Nitrophenyl)-4-bromo-2-methyl-aniline A mixture of 2.9 ml (27.5 mmol) of 2-fluoro-nitrobenzene, 10.55 g (55 mmol) of 4-bromo-2-methyl-aniline and 1.60 g (27.5 mmol) of spray-dried potassium fluoride is heated to 180° C. After cooling the reaction mixture is taken up in methylene chloride, washed with $H_2O$, with 10% hydrochloric acid and again with $H_2O$, dried with $Na_2SO_4$, concentrated and purified by flash chromatography (silica gel; petroleum ether/ethyl acetate=75:25).

Yield: 5.95 g (70% of theory), $R_f$ value: 0.69 (silica gel; petroleum ether/ethyl acetate= 75:25)

b. N-(2-aminophenyl)-4-bromo-2-methyl-aniline

A suspension of 5.34 g (17.4 mmol) of N-(2-nitrophenyl)-4-bromo-2-methyl-aniline and 1.7 g of platinum on charcoal is stirred in 100 ml of dichloromethane and 100 ml of methanol at a hydrogen pressure of 3 bar for 1 hour. Then the catalyst is filtered off and the filtrate is evaporated down.

Yield: 4.8 g (100% of theory), $R_f$ value: 0.27 (silica gel; petroleum ether/ethyl acetate=75:25)

c. 1-(4-bromo-2-methyl-phenyl)-2-methyl-benzimidazole

A mixture of 5.22 g (18.8 mmol) of N-(2-aminophenyl)-4-bromo-2-methyl-aniline and 7.1 ml (75.2 mmol) of acetic acid anhydride is heated to boiling for 30 hours, combined with 15 ml of glacial acetic acid and heated to boiling for another 30 hours. Then the reaction mixture is concentrated and purified by flash chromatography (silica gel; methylene chloride).

$R_f$ value: 0.20 (silica gel; petroleum ether/ethyl acetate=75:25)

d. 4-{3-[3-methyl-4-(2-methyl-benzimidazole-1-yl)-phenyl]-propargylamino}benzamidine Prepared analogously to Example 1g from 1-(4-bromo-2-methyl-phenyl)-2-methyl-benzimidazole, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 41% of theory, $R_f$ value: 0.13 (silica gel; methylene chloride/ethanol=80:20)

$C_{25}H_{23}N_5 \times CF_3COOH$ (393.49/507.51)

Mass spectrum:

$(M+H)^+=394$ $(M+2H)^{++}=197.6$

EXAMPLE 8

4-{3-[4-(3-(2-ethoxycarbonyl-ethyl)-5-phenyl-pyrazol-1-yl)-3-methyl-phenyl]-propargylamino}benzamidine a. 1-(4-iodo-2-methyl-phenyl)-3-(2-hydroxycarbonyl-ethyl)-5-phenyl-pyrazole A mixture of 2.5 g (8.78 mmol) of 4-iodo-2-methyl-phenylhydrazine (prepared analogously to J. Am. Chem. Soc. 78, 5854–5857 (1956)), 1.93 g (8.78 mmol) of 4,6-dioxo-6-phenyl-hexanoic acid (prepared analogously to Synthesis 1991, 18–20) and 1.22 ml (8.78 mmol) of triethylamine in 70 ml of methanol is stirred for 3 hours at ambient temperature. Then the volatile constituents are distilled off, the crude product obtained is taken up in 100 ml of ether, washed with 1N HCl and the aqueous phase is extracted with 50 ml of ether and 50 ml of methylene chloride. The combined organic phases are dried and concentrated and the crude product is purified by flash chromatography (silica gel; methylene chloride/ethanol=98:2).

Yield: 2.26 g (60% of theory), $R_f$ value: 0.45 (silica gel; methylene chloride/ethanol=95:5)

$C_{19}H_{17}IN_2O_2$ (432.26)

Mass spectrum:

$(M+H)^+=433$ $(M+Na)^+=455$ $(M-H)^-=431$ b. 3-(2-ethoxycarbonylethyl)-1-(4-iodo-2-methyl-phenyl)-5-phenyl-pyrazole A mixture of 2.26 g (5.23 mmol) of 1-(4-iodo-2-methyl-phenyl)-3-(2-hydroxycarbonyl-ethyl)-5-phenyl-pyrazole and 0.93 g (5.75 mmol) of N,N'-carbonyldiimidazole in 50 ml of ethanol is stirred for 1 hour, then combined with 5.0 ml of absolute ethanol, heated to boiling for 1 hour, concentrated and purified by flash chromatography (silica gel; methylene chloride to methylene chloride/ethanol=98:2).

Yield: 1.4 g (58% of theory), $R_f$ value: 0.35 (silica gel; methylene chloride/ethanol=99:1)

$C_{21}H_{21}IN_2O_2$ (460.32)

Mass spectrum:

$(M+H)^+=461$ $(2M+Na)^+=943$ d. 4-{3-[4-(3-(2-ethoxycarbonyl-ethyl)-5-phenyl-pyrazol-1-yl)-3-methyl-phenyl]-propargylamino}benzamidine Prepared analogously to Example 1g from 3-(2-ethoxycarbonyl-ethyl)-1-(4-iodo-2-methyl-phenyl)-5-phenyl-pyrazole, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 71% of theory, $R_f$ value: 0.13 (Reversed phase silica gel RP-8; methanol/5% NaCl solution=6:4)

$C_{31}H_{31}N_5O_2 \times CF_3COOH$ (505.63/619.65)

Mass spectrum: $(M+H)^+=506$

EXAMPLE 9

4-[3-(3-methyl-4-morpholinocarbonyl-phenyl)propargylthio]benzamidine a. N-[4-(3-hydroxy-propyn-1-yl)-2-methyl-benzoyl]-morpholine Prepared analogously to Example 1g from N-(4-bromo-2-methyl-benzoyl)-morpholine, propargyl alcohol, tetrakis(triphenylphosphine)palladium(0), copper(I)iodide and triethylamine in acetonitrile.

Yield: 46% of theory, $R_f$ value: 0.40 (silica gel; ethyl acetate/petroleum ether=6:4)

b. N-[4-(3-methylsulphonyl-propyn-1-yl)-2-methyl-benzoyl]-morpholine

A mixture of 0.90 g (3.5 mmol) of N-[4-(3-hydroxy-propyn-1-yl)-2-methyl-benzoyl]-morpholine, 0.45 g (3.9 mmol) of methanesulphonic acid chloride and 1.0 ml (7 mmol) of triethylamine in 20 ml of tetrahydrofuran is stirred for 1 hour at ambient temperature. Then ice water is added, the mixture is extracted with ethyl acetate, the organic phase is washed with water and concentrated.

Yield: 2.0 g of brown oil (83% of theory), $R_f$ value: 0.72 (silica gel; methylene chloride/ethanol/ammonia=90:10:1)

c. 4-[3-(3-methyl-4-morpholinocarbonyl-phenyl) propargylthio]benzonitrile

A solution of 1.0 g (3mmol) of N-[4-(3-methylsulphonyl-propyn-1-yl)-2-methyl-benzoyl]-morpholine, 4-cyano-thiophenol and 5 ml of N,N-diisopropylethylamine in 10 ml of dimethylformamide is heated to 100° C. for 30 minutes. Then the mixture is diluted with 50 ml of ethyl acetate, washed 2× with 14% NaCl solution, dried, concentrated and purified by flash chromatography (silica gel; elution gradient: methylene chloride to methylene chloride/ethanol= 98:2).

Yield: 0.8 g (73% of theory), $R_f$ value: 0.62 (silica gel; methylene chloride/ethanol= 95:5)

d. 4-[3-(3-methyl-4-morpholinocarbonyl-phenyl] propargyl-thio}benzamidine

Prepared analogously to Example 4c from 4-[3-(3-methyl-4-morpholinocarbonyl-phenyl)propargylthio] benzonitrile, ethanol saturated with hydrogen chloride gas and ammonium carbonate.

Yield: 87% of theory, $R_f$ value: 0.38 (silica gel; ethyl acetate/ethanol/ammonia= 50:45:5)

$C_{22}H_{23}N_3O_2S\times HCl$ (393.53/429.99)

Mass spectrum: $(M+H)^+=394$

EXAMPLE 10

E4-{3-[3-(2-ethoxycarbonyl-vinyl)-4-pyrrolidinocarbonyl-phenyl] propargylamino}benzamidine a. 5-bromo-1,3-dihydro-isobenzofuran-1-one

A solution of 0.43 g (2.0 mmol) of 4-bromo-2-methyl-benzoic acid, 0.34 g (1.9 mmol) of N-bromosuccinimide and 20 mg of azaisobutyronitrile in 7 ml of methyl propionate is heated to boiling for 1 hour under a nitrogen atmosphere and irradiated with a mercury vapour lamp. The reaction mixture is concentrated, taken up in methylene chloride, washed with $H_2O$, dried with $Na_2SO_4$ and purified by flash chromatography (silica gel; ethyl acetate/petroleum ether=5:95 to 15:85).

Yield: 0.23 g (54% of theory), $R_f$ value: 0.52 (silica gel; ethyl acetate/petroleum ether= 20:80)

$C_8H_5BrO_2$ (213.03)

Mass spectrum: $M^+=212/214$ (bromine isotopes)

b. N-(4-bromo-2-hydroxymethyl-benzoyl)-pyrrolidine

A mixture of 2.55 g (11.9 nmol) of 5-bromo-1,3-dihydro-isobenzofuran-1-one and 1.3 ml (15.5 mmol) of pyrrolidine in 15 ml of ethanol is heated to boiling for 8 hours: then another 1.3 ml of pyrrolidine is added and heating is continued for a further 22 hours. Then the solvent is eliminated, the filtrate is taken up in ethyl acetate, washed with $H_2O$, dried with $Na_2SO_4$ and purified by flash chromatography (silica gel; methylene chloride/ethanol=99:1 to 99:2).

Yield: 3.01 g (89% of theory), $R_f$ value: 0.45 (silica gel; methylene chloride/ethanol= 95:5)

c. N-(4-bromo-2-formyl-benzoyl)-pyrrolidine

A total of 25 g of manganese dioxide are added batchwise—spread over several hours—to a solution of 4.0 g (14 mmol) of N-(4-bromo-2-hydroxymethyl-benzoyl)-pyrrolidine in 80 ml of methylene chloride and the mixture is stirred for a total of 30 hours. Then it is filtered through kieselguhr and the solvent is distilled off. The crude product is reacted without any further purification.

Yield 3.3 g (84% of theory), $R_f$ value: 0.31 (silica gel; methylene chloride/ethanol= 95:5)

d. E-N-[4-bromo-2-(2-ethoxycarbonyl-vinyl)-benzoyl]-pyrrolidine

A solution of 1.27 g (4.5 mmol) of N-(4-bromo-2-formyl-benzoyl)-pyrrolidine and 1.65 g (4.5 mmol) of carboethoxymethylene triphenylphosphorane in 45 ml of toluene is heated to 80° C. for 4 hours. After removal of the solvent the residue is purified by flash chromatography (silica gel; methylene chloride/ethanol 99:1 to 99:2).

Yield: 1.07 g (67% of theory), $R_f$ value: 0.33 (silica gel; petroleum ether/ethyl acetate 1:1).

e. E-4-{3-[3-(2-ethoxycarbonyl-vinyl)-4-pyrrolidinocarbonyl-phenyl] propargylamino}benzamidine Prepared analogously to Example 1g from E-N-[4-bromo-2-(2-ethoxycarbonyl-vinyl)-benzoyl]-pyrrolidine, N-tert-butoxycarbonyl-4-propargylamino-benzamidine, tetrakis (triphenylphosphine)palladium(0), copper(I)iodide and triethylamine in acetonitrile and subsequent cleaving of the tert-butoxycarbonyl group by trifluoroacetic acid analogously to Example 2.

Yield: 56% of theory, $R_f$ value: 0.17 (silica gel; methylene chloride/ethanol= 4:1)

$C_{26}H_{28}N_4O_3\times CF_3COOH$ (444.54/558.56)

Mass spectrum: $(M+H)^+=445$

EXAMPLE 11

N-tert-butoxycarbonyl-4-[3-(2,5-dimethyl-4-isopropylcarbonyl-phenyl)propargylamino] benzamidine a. 4-bromo-2,5-dimethyl-1-isopropylcarbonyl-benzene 31.2 ml of (50 mmol) of a 1.6 molar n-butyl lithium solution in hexane are added dropwise to a solution of 13.5 g (50 mmol) of 2,5-dibromo-p-xylene in 100 ml of tetrahydrofuran cooled to −78° C., the mixture is stirred for 30 minutes and then combined with 4.5 ml of (50 mmol) of isobutyronitrile. The reaction mixture is allowed to come back slowly to ambient temperature, stirred for 1 hour, then combined with 50 ml of 2N HCl and 70 ml of diethyl ether and stirred for another 16 hours. The aqueous phase is separated off and extracted 2× with diethyl ether. The combined organic phases are dried with $Na_2SO_4$, evaporated down and the residue is purified by flash chromatography (silica gel; petroleum ether to petroleum ether/ethyl acetate=9:1).

Yield: 6.08 g (48% of theory), $R_f$ value: 0.58 (silica gel; petroleum ether/ethyl acetate=9:1).

$C_{12}H_{15}BrO$ (255.16)

Mass spectrum: $M^+$=254/256 (bromine isotopes)

b. N-tert-butoxycarbonyl-4-[3-(2,5-dimethyl-4-isopropyl-carbonyl-phenyl)propargylamino]benzamidine Prepared analogously to Example 1g from 4-bromo-2,5-dimethyl-1-isopropylcarbonyl-benzene, N-tert-butoxycarbonyl-4-propargylamino-benzamidine, tetrakis(triphenylphosphine)palladium(0), copper(I)iodide and triethylamine in acetonitrile.

Yield: 57% of theory, $R_f$ value: 0.3 (silica gel; methylene chloride/ethanol=98:2)

$C_{27}H_{33}N_3O_3$ (447.58)

Mass spectrum: $(M+H)^+$=448

EXAMPLE 12

4-[3-(2,5-dimethyl-4-isopropylcarbonyl-phenyl)propargylamino]benzamidine

Prepared analogously to Example 2 from N-tert-butoxycarbonyl-4-[3-(2,5-dimethyl-4-isopropylcarbonyl-phenyl)propargyl-amino]benzamidine and trifluoroacetic acid.

Yield: 34% of theory, $R_f$ value: 0.30 (silica gel; methylene chloride/ethanol=4:1)

$C_{22}H_{25}N_3O \times CF_3COOH$ (347.46/461.88)

Mass spectrum: $(M+H)^+$=348

EXAMPLE 13

4-{3-[4-[(1-methyl-imidazol-2-yl)carbonyl]-phenyl]-propargylamino}benzamidine a. 2-(4-iodobenzoyl)-1-methyl-imidazole 0.82 g (10 mmol) of 1-methyl-imidazole and 2.7 g (10 mmol) of 4-iodobenzoic acid chloride are combined in 10 ml of acetonitrile while cooling with an ice bath, 1.4 ml (10 mmol) of triethylamine are added and the mixture is then stirred for 16 hours at ambient temperature. The crude product is taken up in 30 ml of ethyl acetate, washed with $H_2O$, dried, concentrated in vacuo and purified by flash chromatography (silica gel; methylene chloride).

Yield: 1.9 g (51% of theory), $R_f$ value: 0.62 (silica gel; ethyl acetate/petroleum ether=60:40)

b. 4-{3-[4-[(1-methyl-imidazol-2-yl)carbonyl]-phenyl]-propargylamino}benzonitrile Prepared analogously to Example 1 g from 2-(4-iodobenzoyl)-1-methyl-imidazole, 4-propargylamino-benzonitrile, tetrakis(triphenylphosphine)palladium(0), copper(I)iodide and triethylamine in acetonitrile.

Yield: 39% of theory, $R_f$ value: 0.28 (silica gel; ethyl acetate/petroleum ether=60:40)

c. 4-{3-[4-[(1-methyl-imidazol-2-yl)carbonyl]-phenyl]-propargylamino}benzamidine Prepared analogously to Example 4c from 4-{3-[4-[(1-methyl-imidazol-2-yl)carbonyl]-phenyl]-propargylamino}benzonitrile, ethanol saturated with hydrogen chloride gas and ammonium carbonate.

Yield: 77% of theory, $R_f$ value: 0.37 (silica gel; ethyl acetate/ethanol/ammonia=50:45:5)

$C_{21}H_{19}N_5O \times HCl$ (357.42/393.89)

Mass spectrum:

$(M+H)^+$=358

$(M+2H)^{++}$=179.6

$(M+HCl)^{+-}$394/396 (chlorine isotopes)

EXAMPLE 14

4-{3-[3-methyl-4-[(1-methyl-imidazol-2-yl)carbonyl]-phenyl]-propargylamino}benzamidine Prepared analogously to Example 4c from 4-{3-[3-methyl-4-[(1-methyl-imidazol-2-yl)carbonyl]-phenyl]-propargylamino}benzonitrile (prepared analogously to Example 13b), ethanol saturated with hydrogen chloride gas and ammonium carbonate.

Yield: 62% of theory, $R_f$ value: 0.39 (silica gel; ethyl acetate/ethanol/ammonia=50:45:5)

$C_{22}H_{21}N_5O \times HCl$ (371.45/407.91)

Mass spectrum: $(M+H)^+$=372

EXAMPLE 15

4-{3-[4-[(imidazol-2-yl)carbonyl]-phenyl]-propargylamino}benzamidine

Prepared analogously to Example 4c from 4-{3-[4-[(imidazol-2-yl)carbonyl]-phenyl]-propargylamino}benzonitrile, ethanol saturated with hydrogen chloride gas and ammonium carbonate.

Yield: 60% of theory, $R_f$ value: 0.35 (silica gel; ethyl acetate/ethanol/ammonia=50:45:5)

$C_{22}H_{21}N_5O \times HCl$ (343.41/379.87)

Mass spectrum:

$(M+H)^+$=344

$(M+2H)^{++}$=172.7

EXAMPLE 16

4-{3-[4-[(thiophen-2-yl)carbonyl]-phenyl]-propargylamino}benzamidine

Prepared analogously to Example 4c from 4-{3-[4-[(thiophen-2-yl)carbonyl]-phenyl]-propargylamino}benzonitrile, ethanol saturated with hydrogen chloride gas and ammonium carbonate.

Yield: 85% of theory, $R_f$ value: 0.45 (silica gel; ethyl acetate/ethanol/ammonia=50:45:5)

$C_{21}H_{17}N_3OS \times HCl$ (359.45/395.91)

Mass spectrum: $(M+H)^+ = 360$

EXAMPLE 17

4-{3-[4-(2-methylphenylcarbonyl)-phenyl]-propargylamino}benzamidine

Prepared analogously to Example 4c from 4-{3-[4-(2-methylphenylcarbonyl)-phenyl]-propargylamino}benzonitrile, ethanol saturated with hydrogen chloride gas and ammonium carbonate.

Yield: 80% of theory, $R_f$ value: 0.45 (silica gel; methylene chloride/ethanol=4:1)

$C_{24}H_{21}N_3O \times HCl$ (367.45/403.91)

Mass spectrum: $(M+H)^+ = 368$

EXAMPLE 18

4-{3-[4-(4-methylphenylcarbonyl)-phenyl]-propargylamino}benzamidine

Prepared analogously to Example 4c from 4-{3-[4-(4-methylphenylcarbonyl)-phenyl]-propargylamino}benzonitrile, ethanol saturated with hydrogen chloride gas and ammonium carbonate.

Yield: 65% of theory, $R_f$ value: 0.15 (silica gel; methylene chloride/ethanol=4:1)

$C_{24}H_{21}N_3O \times HCl$ (367.45/403.91)

Mass spectrum:
$(M+H)^+ = 368$
$(2M+H)^{++} = 735$

EXAMPLE 19

4-{3-[4-(2-chlorophenylcarbonyl)-phenyl]-propargylamino}benzamidine

Prepared analogously to Example 2 from N-tert-butoxycarbonyl-4-{3-[4-(2-chlorophenylcarbonyl)-phenyl]-propargylamino}benzamidine and trifluoroacetic acid.

Yield: 52% of theory, $R_f$ value: 0.29 (silica gel; methylene chloride/ethanol=4:1 and 1 drop of acetic acid)

$C_{23}H_{18}ClN_3O \times CF_3COOH$ (387.87/501.90)

Mass spectrum: $(M+H)^+ = 388/390$ (chlorine isotopes)

EXAMPLE 20

4-{3-[4-(3-chlorophenylcarbonyl)-phenyl]-propargylamino}benzamidine

Prepared analogously to Example 4c from 4-{3-[4-(3-chlorophenylcarbonyl)-phenyl]-propargylamino}benzonitrile, ethanol saturated with hydrogen chloride gas and ammonium carbonate.

Yield: 61% of theory, $R_f$ value: 0.25 (silica gel; methylene chloride/ethanol=4:1)

$C_{23}H_{18}ClN_3O \times HCl$ (387.87/424.33)

Mass spectrum: $(M+H)^+ = 388/390$ (chlorine isotopes)

EXAMPLE 21

4-{3-[4-(4-chlorophenylcarbonyl)-phenyl]-propargylamino}benzamidine

Prepared analogously to Example 2 from N-tert-butoxycarbonyl-4-{3-[4-(2-chlorophenylcarbonyl)-phenyl]-propargylamino}benzamidine and trifluoroacetic acid.

Yield: 42% of theory, $R_f$ value: 0.28 (silica gel; methylene chloride/ethanol=4:1 and 1 drop of acetic acid)

$C_{23}H_{18}ClN_3O \times CF_3COOH$ (387.87/501.90)

Mass spectrum: $(M+H)^+ = 388/390$ (chlorine isotopes)

EXAMPLE 22

4-{3-[4-(pyrid-2-yl-carbonyl)-phenyl]-propargylamino}benzamidine

Prepared analogously to Example 4c from 4-{3-[4-(pyrid-2-yl-carbonyl)-phenyl]-propargylamino}benzonitrile, ethanol saturated with hydrogen chloride gas and ammonium carbonate.

Yield: 47% of theory, $R_f$ value: 0.48 (silica gel; ethyl acetate/ethanol/ammonia=50:45:5)

$C_{22}H_{18}N_4O \times HCl$ (354.42/390.88)

Mass spectrum: $(M+H)^+ = 355$

EXAMPLE 23

4-{3-[4-(pyrid-3-yl-carbonyl)-phenyl]-propargylamino}benzamidine

Prepared analogously to Example 2 from N-tert-butoxycarbonyl-4-{3-[4-(pyrid-3-yl-carbonyl)-phenyl]-propargylamino}benzamidine and trifluoroacetic acid.

Yield: 89% of theory, $R_f$ value: 0.37 (silica gel; ethyl acetate/ethanol/ammonia=50:45:5)

$C_{22}H_{18}N_4O \times CF_3COOH$ (354.42/468.44)

Mass spectrum: $(M+H)^+ = 355$

EXAMPLE 24

4-{3-[4-(pyrid-4-yl-carbonyl)-phenyl]-propargylamino}benzamidine

Prepared analogously to Example 2 from N-tert-butoxycarbonyl-4-{3-[4-(pyrid-4-yl-carbonyl)-phenyl]-propargylamino}benzamidine and trifluoroacetic acid.

Yield: 84% of theory, $R_f$ value: 0.37 (silica gel; ethyl acetate/ethanol/ammonia=50:45:5)

$C_{22}H_{18}N_4O \times CF_3COOH$ (354.42/468.44)

Mass spectrum: $(M+H)^+ = 355$

EXAMPLE 25

4-[3-(2-methyl-4-phenylcarbonyl-phenyl)-propargylamino}benzamidine

Prepared analogously to Example 4c from 4-[3-(2-methyl-4-phenylcarbonyl-phenyl]-propargylamino}benzonitrile, ethanol saturated with hydrogen chloride gas and ammonium carbonate.

Yield: 47% of theory, $R_f$ value: 0.24 (silica gel; methylene chloride/ethanol= 4:1)

$C_{24}H_{21}N_3O \times HCl$ (367.45/403.91)

Mass spectrum: $(M+H)^+=368$

EXAMPLE 26

4-[3-(3-methyl-4-phenylcarbonyl-phenyl)-propargylamino]benzamidine

Prepared analogously to Example 4c from 4-[3-(3-methyl-4-phenylcarbonyl-phenyl)-propargylamino]benzonitrile, ethanol saturated with hydrogen chloride gas and ammonium carbonate.

Yield: 50% of theory, $R_f$ value: 0.16 (silica gel; methylene chloride/ethanol= 4:1)

$C_{24}H_{21}N_3O \times HCl$ (367.45/403.91)

Mass spectrum: $(M+H)^+=368$

EXAMPLE 27

4-[3-(4-phenylcarbonyl-phenyl)-propargylamino]benzamidine

Prepared analogously to Example 4c from 4-[3-(4-phenylcarbonyl-phenyl)-propargylamino]benzonitrile, ethanol saturated with hydrogen chloride gas and ammonium carbonate.

Yield: 78% of theory, $R_f$ value: 0.13 (silica gel; methylene chloride/ethanol= 4:1)

$C_{23}H_{19}N_3O \times HCl$ (353.42/389.88)

Mass spectrum: $(M+H)^+=354$

EXAMPLE 28

4-[3-(2-amino-4-phenylcarbonyl-phenyl)-propargylamino]benzamidine a. 4-iodo-3-nitro-benzophenone 5.3 g (17 mmol) of 4-iodo-3-nitrobenzoic acid and 8.0 g (60 mmol) of aluminium trichloride are added successively to 70 ml of benzene while cooling with an ice bath. Then the mixture is stirred for 2 hours at ambient temperature, then poured into ice water, extracted with methylene chloride, dried with sodium sulphate and concentrated in vacuo.

Yield: 5.4 g (90% of theory), $R_f$ value: 0.83 (silica gel; ethyl acetate/petroleum ether= 3:7)

b. 3-amino-4-iodo-benzophenone

A mixture of 5.0 g (14 mmol) of 4-iodo-3-nitro-benzophenone, 7.5 g (42 mmol) of sodium dithionite, 40 ml of pyridine and 15 ml of water is heated to 40° C. for 2 hours. Then the mixture is concentrated in vacuo, combined with ice water and extracted with ethyl acetate. The organic phase is dried with sodium sulphate and the solvent is distilled off in vacuo.

Yield: 3.4 g (76% of theory), $R_f$ value: 0.60 (silica gel; ethyl acetate/petroleum ether= 3:7)

c. 4-[3-(2-amino-4-phenylcarbonyl-phenyl)-propargylamino]benzamidine

Prepared analogously to Example 1 g from 3-amino-4-iodo-benzophenone, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 54% of theory, $R_f$ value: 0.60 (silica gel; ethyl acetate/ethanol/ammonia= 50:45:5)

$C_{23}H_{20}N_4O \times CF_3COOH$ (368.46/482.48)

Mass spectrum: $(M+H)^+=369$

EXAMPLE 29

4-[3-(2-acetamido-4-phenylcarbonyl-phenyl)-propargylamino]benzamidine

Prepared analogously to Example 1 g from 3-acetamido-4-iodo-benzophenone, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 61% of theory, $R_f$ value: 0.30 (silica gel; ethyl acetate/ethanol/ammonia= 50:45:5)

$C_{25}H_{22}N_4O_2 \times CF_3COOH$ (410.49/524.51)

Mass spectrum: $(M+H)^+=411$

EXAMPLE 30

4-{3-[4-(2-methoxycarbonyl-phenylcarbonyl)-phenyl]-propargylamino}benzamidine

Prepared analogously to Example 4c from 4-{3-[4-(2-methoxycarbonyl-phenylcarbonyl)-phenyl]-propargylamino}benzonitrile, methanol saturated with hydrogen chloride gas and ammonium carbonate.

Yield: 18% of theory, $R_f$ value: 0.1 (silica gel; methylene chloride/ethanol=4:1)

$C_{25}H_{21}N_3O_3 \times HCl$ (411.46/447.92)

Mass spectrum: $(M+H)^+=412$

EXAMPLE 31

4-{3-[4-(2-hydroxycarbonyl-phenylcarbonyl)-phenyl]-propargylamino}benzamidine

Prepared analogously to Example 3 from 4-{3-[4-(2-methoxycarbonyl-phenylcarbonyl)-phenyl]-propargylamino}benzamidine and lithium hydroxide and subsequent treatment with ammonium chloride.

Yield: 41% of theory, $C_{24}H_{19}N_3O_3 \times HCl$ (397.43/433.89)

Mass spectrum:

$(M+H)^+=398$ $(M+Na)^+=420$ $(M+2Na)^{++}=221.6$

EXAMPLE 32

4-[1-methyl-3-(4-phenylcarbonyl-phenyl)-propargylamino]benzamidine

Prepared analogously to Example 4c from 4-[1-methyl-3-(4-phenylcarbonyl-phenyl)-propargylamino]benzonitrile, ethanol saturated with hydrogen chloride gas and ammonium carbonate.

Yield: 80% of theory, $R_f$ value: 0.52 (silica gel; ethyl acetate/ethanol/ammonia=50:45:5)

$C_{24}H_{21}N_3O \times HCl$ (367.47/403.93)

Mass spectrum: $(M+H)^+=368$

EXAMPLE 33

3-methoxy-4-[3-(4-phenylcarbonyl-3-methyl-phenyl)-propargylamino]benzamidine

Prepared analogously to Example 4c from 3-methoxy-4-[3-(4-phenylcarbonyl-3-methyl-phenyl)-propargylamino] benzonitrile, ethanol saturated with hydrogen chloride gas and ammonium carbonate.

Yield: 29% of theory, $R_f$ value: 0.24 (silica gel; methylene chloride/ethanol=4:1)

$C_{25}H_{23}N_3O_2 \times HCl$ (397.48/433.94)

Mass spectrum: $(M+H)^+=398$

EXAMPLE 34

4-[3-(5-phenylcarbonyl-pyrid-2-yl)-propargylamino]benzamidine

Prepared analogously to Example 1g from 2-chloro-5-phenylcarbonyl-pyridine, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 47% of theory, $R_f$ value: 0.55 (silica gel; ethyl acetate/ethanol/ammonia=50:45:5)

$C_{22}H_{18}N_4O \times CF_3COOH$ (354.42/468.44)

Mass spectrum: $(M+H)^+=355$

EXAMPLE 35

4-[3-(5-phenylcarbonyl-thiophen-2-yl)-propargylamino]benzamidine

A solution of 1.2 g (2.6 mmol) of N-tert-butoxycarbonyl-4-[3-(5-phenylcarbonyl-thiophen-2-yl)-propargylamino]benzamidine and 4 ml of trimethylsilyl iodide in 50 ml of methylene chloride is stirred for 3 hours, then diluted with 50 ml of methylene chloride and 25 ml of ethanol and washed with water. The organic phase is dried, concentrated and purified by flash chromatography (silica gel; methylene chloride/ethanol=49:1 to 9:1).

Yield: 20% of theory, $R_f$ value: 0.28 (silica gel; ethyl acetate/ethanol/ammonia=50:45:5)

$C_{21}H_{17}N_3OS \times HI$ (359.46/487.37)

Mass spectrum: $(M+H)^+=360$

EXAMPLE 36

4-[3-(4-isopropylcarbonyl-phenyl)propargylamino]benzamidine

Prepared analogously to Example 4c from 4-[3-(4-isopropylcarbonyl-phenyl)propargylamino]benzonitrile, ethanol saturated with hydrogen chloride gas and ammonium carbonate.

Yield: 24% of theory, $R_f$ value: 0.13 (silica gel; methylene chloride/ethanol=4:1)

$C_{20}H_{21}N_3O \times HCl$ (319.41/355.87)

Mass spectrum:

$(M+H)^+=320$ $(M+H+HCl)^+=356/358$ (chlorine isotopes)

EXAMPLE 37

4-[3-(4-cyclopentylcarbonyl-phenyl)propargylamino]benzamidine

Prepared analogously to Example 4c from 4-[3-(4-cyclopentylcarbonyl-phenyl)propargylamino]benzonitrile, ethanol saturated with hydrogen chloride gas and ammonium carbonate.

Yield: 53% of theory, $R_f$ value: 0.20 (silica gel; methylene chloride/ethanol=4:1)

$C_{22}H_{23}N_3O \times HCl$ (345.44/381.90)

Mass spectrum: $(M+H)^+=346$

EXAMPLE 38

4-[3-(4-tert-butylcarbonyl-2,5-dimethyl-phenyl)propargylamino]benzamidine

Prepared from N-tert-butoxycarbonyl-4-[3-(4-tert-butylcarbonyl-2,5-dimethyl-phenyl)propargylamino]benzamidine and trifluoroacetic acid analogously to Example 2.

Yield: 18% of theory, $R_f$ value: 0.35 (silica gel; methylene chloride/ethanol=4:1+1 drop of acetic acid)

$C_{23}H_{27}N_3O \times CF_3COOH$ (361.49/475.51)

Mass spectrum: $(M+H)^+=362$

EXAMPLE 39

4-{3-[4-(1,1-dimethyl-2-ethoxycarbonyl-ethylcarbonyl)-2,5-dimethyl-phenyl]propargylamino}benzamidine a. 4-(4-bromo-2,5-dimethyl-phenyl)-3,3-dimethyl-4-oxo-butanoic Acid A solution of 2.85 g (10 mmol) of 4-(4-bromo-2,5-dimethyl-phenyl)4-oxo-butanoic acid is added dropwise over 5 minutes to a suspension of 1.44 g (about 30 mmol) of 50% sodium hydride in oil in 300 ml of tetrahydrofuran and heated to boiling for 2 hours. Then it is cooled to ambient temperature, 2.8 ml of methyl iodide are added dropwise and the mixture is again heated to boiling for 2.5 hours. It is poured into 150 ml of water and the organic solvent is distilled off. The aqueous phase is washed 2× with petroleum ether, acidified with hydrochloric acid and extracted with methylene chloride. The organic phase is dried with sodium sulphate and concentrated.

Yield: 2.45 g (78% of theory), $R_f$ value: 0.35 (silica gel; ethyl acetate/petroleum ether 30:70+1 drop of acetic acid)

$C_{14}H_{17}BrO_3$ (313.19)

Mass spectrum: $(M-H)^-=311/313$ (bromine isotopes)

b. ethyl 4-(4-bromo-2,5-dimethyl-phenyl)-3,3-dimethyl-4-oxo-butanoate

A solution of 3.2 g (10 mmol) of 4-(4-bromo-2,5-dimethyl-phenyl)-3,3-dimethyl4-oxo-butanoic acid in tetrahydrofuran is combined with 3.60 g (11 mmol) of carbonyldiimidazole and stirred for 1 hour at ambient temperature. The solvent is replaced by 20 ml of ethanol and the mixture is heated to boiling for 2 hours. Then the solvent is distilled off, the crude product is taken up in methylene chloride, washed with water, dried with sodium sulphate, concentrated and purified by flash chromatography (silica gel; ethyl acetate/petroleum ether=3:97).

Yield: 2.95 g (87% of theory), $R_f$ value: 0.55 (silica gel; ethyl acetate/petroleum ether= 1:9)

$C_{16}H_2BrO_3$ (341.25)

Mass spectrum:

$(M+H)^+=341/343$ (bromine isotopes)

$(M+Na)^+=363/365$ (bromine isotopes)

c. 4-{3-[4-(1,1-dimethyl-2-ethoxycarbonyl-ethylcarbonyl)-2,5-dimethyl-phenyl] propargylamino}benzamidine Prepared analogously to Example 1 g from ethyl 4-(4-bromo-2,5-dimethyl-phenyl)-3,3-dimethyl-4-oxo-butanoate, N-tert-butoxycarbonyl-4-propargylamino-benzamidine, tetrakis(triphenylphosphine)palladium(0), copper(I)iodide and triethylamine in acetonitrile and subsequent cleaving of the tert-butoxycarbonyl group by trifluoroacetic acid analogously to Example 2.

Yield: 9% of theory, $R_f$ value: 0.35 (silica gel; methylene chloride/ethanol= 4:1)

$C_{26}H_{31}N_3O_3 \times CF_3COOH$ (433.46/547.58)

Mass spectrum: $(M+H)^+=434$

EXAMPLE 40

4-{3-[4-(1,1-dimethyl-2-hydroxycarbonyl-ethylcarbonyl)-2,5-dimethyl-phenyl] propargylamino}benzamidine Prepared analogously to Example 3 from 4-{3-[4-(1,1-dimethyl-2-ethoxycarbonyl-ethylcarbonyl)-2,5-dimethyl-phenyl]propargylamino}benzamidine and lithium hydroxide and subsequent treatment with ammonium chloride.

Yield: 50% of theory, $R_f$ value: 0.3 (Reversed phase silica gel RP-8; methanol/ 5% NaCl solution=60:40)

$C_{24}H_{27}N_3O_3 \times HCl$ (405.50/441.96)

Mass spectrum: $(M+H)^+=406$

EXAMPLE 41

4-[3-(4-pyrrolidinocarbonyl-phenyl)-propargylamino]benzamidine

Prepared analogously to Example 2 from N-tert-butoxycarbonyl-4-[3-(4-pyrrolidinocarbonyl-phenyl)-propargylamino]benzamidine and trifluoroacetic acid.

Yield: 37% of theory, $R_f$ value: 0.29 (silica gel; methylene chloride/ethanol=4:1 and 1 drop of acetic acid)

$C_{21}H_{22}N_4O \times CF_3COOH$ (346.44/460.46)

Mass spectrum: $(M+H)^+=347$

EXAMPLE 42

4-[3-(3-methyl-4-pyrrolidinocarbonyl-phenyl)-propargylamino]-benzamidine

Prepared analogously to Example 2 from N-tert-butoxycarbonyl-4-[3-(3-methyl-4-pyrrolidinocarbonyl-phenyl)-propargylamino]benzamidine and trifluoroacetic acid.

Yield: 52% of theory, $R_f$ value: 0.27 (silica gel; methylene chloride/ethanol=4:1 and 1 drop of acetic acid)

$C_{22}H_{24}N_4O \times CF_3COOH$ (360.46/474.48)

Mass spectrum:

$(M+H)^+=361$ $(M+2H)^{++}=181$

EXAMPLE 43

4-[3-(2,5-dimethyl-4-pyrrolidinocarbonyl-phenyl)-propargylamino]benzamidine

Prepared analogously to Example 2 from N-tert-butoxycarbonyl-4-[3-(2,5-dimethyl-4-pyrrolidinocarbonyl-phenyl)-propargylamino]benzamidine and trifluoroacetic acid.

Yield: 20% of theory, $R_f$ value: 0.3 (silica gel; methylene chloride/ethanol=4:1)

$C_{23}H_{26}N_4O \times CF_3COOH$ (374.49/488.51)

Mass spectrum: $(M+H)^+=375$

EXAMPLE 44

4-[N-methyl-3-(3-methyl-4-pyrrolidinocarbonyl-phenyl)-propargylamino]benzamidine Prepared analogously to Example 4c from 4-[N-methyl-3-(3-methyl-4-pyrrolidinocarbonyl-phenyl)-propargylamino]benzonitrile, ethanol saturated with hydrogen chloride gas and ammonium carbonate.

Yield: 67% of theory, $R_f$ value: 0.19 (silica gel; methylene chloride/ethanol= 4:1)

$C_{23}H_{26}N_4O \times HCl$ (374.49/410.95)

Mass spectrum: $(M+H)^+=375$

EXAMPLE 45 rac-4-{3-[4-(2-methyl-pyrrolidinocarbonyl)-phenyl]-propargylamino}benzamidine

Prepared analogously to Example 2 from rac-N-tert-butoxycarbonyl-4-{3-[4-(2-methyl-pyrrolidinocarbonyl)-phenyl]-propargylamino}benzamidine and trifluoroacetic acid.

Yield: 32% of theory, $R_f$ value: 0.34 (silica gel; methylene chloride/ethanol=4:1 and 1 drop of acetic acid)

$C_{22}H_{24}N_4O \times CF_3COOH$ (360.48/474.48)

Mass spectrum:

$(M+H)^+ = 361$ $(M+2H)^{++} = 181$

EXAMPLE 46 rac-4-{3-[3-methyl-4-(2-methyl-pyrrolidinocarbonyl)-phenyl]-propargylamino}benzamidine Prepared analogously to Example 2 from rac-N-tert-butoxycarbonyl-4-{3-[3-methyl-4-(2-methyl-pyrrolidinocarbonyl)-phenyl]-propargylamino}benzamidine and trifluoroacetic acid.

Yield: 90% of theory, $R_f$ value: 0.31 (silica gel; methylene chloride/ethanol=4:1 and 1 drop of acetic acid)

$C_{23}H_{26}N_4O \times CF_3COOH$ (374.49/488.51)

Mass spectrum: $(M+H)^+ = 375$

EXAMPLE 47 rac-4-{3-[2-methyl-4-(2-methyl-pyrrolidinocarbonyl)-phenyl]-propargylamino}benzamidine Prepared analogously to Example 2 from rac-N-tert-butoxycarbonyl-4-{3-[2-methyl-4-(2-methyl-pyrrolidinocarbonyl)-phenyl]-propargylamino}benzamidine and trifluoroacetic acid.

Yield: 63% of theory, $R_f$ value: 0.2 (silica gel; methylene chloride/ethanol=4:1)

$C_{23}H_{26}N_4O \times CF_3COOH$ (374.49/488.51)

Mass spectrum: $(M+H)^+ = 375$

EXAMPLE 48

4-[3-(2-methyl-4-pyrrolidinocarbonyl-phenyl)-propargyl-amino]benzamidine

Prepared analogously to Example 2 from N-tert-butoxycarbonyl-4-[3-(2-methyl-4-pyrrolidinocarbonyl-phenyl)-propargylamino]benzamidine and trifluoroacetic acid.

Yield: 86% of theory, $R_f$ value: 0.25 (silica gel; methylene chloride/ethanol=4:1)

$C_{22}H_{24}N_4O \times CF_3COOH$ (360.46/474.48)

Mass spectrum: $(M+H)^+ = 361$

EXAMPLE 49 rac-2-methoxy-4-{3-[3-methyl-4-(2-methyl-pyrrolidinocarbonyl)-phenyl]-propargylamino}benzamidine Prepared analogously to Example 4c from rac-2-methoxy-4-{3-[3-methyl-4-(2-methyl-pyrrolidinocarbonyl)-phenyl]-propargylamino}benzonitrile, ethanol saturated with hydrogen chloride gas and ammonium carbonate.

Yield: 23% of theory, $R_f$ value: 0.33 (silica gel; methylene chloride/ethanol=4:1 and 1 drop of acetic acid)

$C_{24}H_{28}N_4O_2 \times HCl$ (404.52/440.98)

Mass spectrum:

$(M+H)^+ = 405$ $(2M+H)^+ = 809$

EXAMPLE 50

4-[1-methyl-3-(3-methyl-4-pyrrolidinocarbonyl-phenyl)-propargylamino]benzamidine Prepared analogously to Example 4c from 4-[1-methyl-3-(3-methyl-4-pyrrolidinocarbonyl-phenyl)-propargylamino]benzonitrile, ethanol saturated with hydrogen chloride gas and ammonium carbonate.

Yield: 79% of theory, $R_f$ value: 0.43 (silica gel; ethyl acetate/ethanol/ammonia=50:45:5)

$C_{23}H_{26}N_4O_2 \times HCl$ (374.49/410.96)

Mass spectrum: $(M+H)^+ = 375$

EXAMPLE 51 rac-4-{3-[2,5-dimethyl-4-(2-methyl-pyrrolidinocarbonyl)-phenyl]-propargylamino}benzamidine Prepared analogously to Example 2 from rac-N-tert-butoxycarbonyl-4-{3-[2,5-dimethyl-4-(2-methyl-pyrrolidinocarbonyl)-phenyl]-propargylaamino}benzamidine and trifluoroacetic acid.

Yield: 4% of theory, $R_f$ value: 0.1 (silica gel; methylene chloride/ethanol=4:1)

$C_{24}H_{28}N_4O \times CF_3COOH$ (388.51/502.54)

Mass spectrum: $(M+H)^+ = 389$

EXAMPLE 52

2-[3-(3-methyl-4-pyrrolidinocarbonyl-phenyl]-propargylamino]-5-amidino-pyridine

Prepared analogously to Example 4c from 2-[3-(3-methyl-4-pyrrolidinocarbonyl-phenyl)-propargylamino]-5-cyano-pyridine, ethanol saturated with hydrogen chloride gas and ammonium carbonate.

Yield: 43% of theory, $R_f$ value: 0.20 (silica gel; methylene chloride/ethanol=4:1)

$C_{21}H_{23}N_5O \times HCl$ (361.45/397.91)

Mass spectrum: $(M+H)^+ = 362$

EXAMPLE 53

4-[3-(3-methyl-4-tetrahydropyrazolocarbonyl-phenyl)-propargylamino]benzamidine

Prepared analogously to Example 2 from N-tert-butoxycarbonyl-4-{3-[3-methyl-4-(2-butoxycarbonyl-tetrahydropyrazolocarbonyl)-phenyl]-propargylamino}benzamidine and trifluoroacetic acid.

Yield: 28% of theory, $R_f$ value: 0.45 (Reversed phase silica gel RP-8; methanol/5% NaCl solution=60:40)

$C_{21}H_{23}N_5O \times 2\ CF_3COOH$ (361.46/589.50)

Mass spectrum: $(M+H)^+ = 362$

EXAMPLE 54

4-{3-[3-methyl-4-(4,5-dihydropyrazolocarbonyl)-phenyl]-propargylamino}benzamidine Prepared analogously to Example 2 using old N-tert-butoxycarbonyl-4-{3-[3-methyl-4-(tetrahydropyrazolocarbonyl)-phenyl]-propargylamino}benzamidine oxidised with oxygen from the air and trifluoroacetic acid.

Yield: 5% of theory, $R_f$ value: 0.49 (Reversed phase silica gel RP-8; methanol/5% NaCl solution=60:40)

$C_{21}H_{21}N_5O \times CF_3COOH$ (359.44/473.46)

Mass spectrum: $(M+H)^+=360$

EXAMPLE 55

4-{3-[2,5-dimethyl-4-(7-azabicyclo[2,2,1]hept-7-yl-carbonyl)-phenyl]-propargylamino}benzamidine Prepared analogously to Example 2 from N-tert-butoxycarbonyl-4-{3-[2,5-dimethyl-4-(7-azabicyclo[2,2,1]hept-7-yl-carbonyl)-phenyl]-propargylamino}benzamidine and trifluoroacetic acid.

Yield: 58% of theory, $R_f$ value: 0.49 (silica gel; methylene chloride/ethanol=19:1)

$C_{25}H_{28}N_4O \times CF_3COOH$ (400.53/514.55)

Mass spectrum: $(M+H)^+=401$

EXAMPLE 56 rac-4-{3-[4-(3-amino-pyrrolidinocarbonyl)-3-methyl-phenyl]-propargylamino}benzamidine Prepared analogously to Example 2 from rac-N-tert-butoxycarbonyl-4-{3-[4-(3-(tert-butoxycarbonyl)amino-pyrrolidinocarbonyl)-3-methyl-phenyl]-propargylamino}benzamidine and trifluoroacetic acid.

Yield: 100% of theory, $R_f$ value: 0.60 (Reversed phase silica gel RP-8; methanol/5% NaCl solution=60:40)

$C_{22}H_{25}N_5O \times 2CF_3COOH$ (375.48/603.52)

Mass spectrum:
$(M+H)^+=376$
$(M+2H)^{++}=188.5$

EXAMPLE 57

4-{3-[4-(indolin-1-yl-carbonyl)-phenyl]-propargylamino}benzamidine

Prepared analogously to Example 2 from N-tert-butoxycarbonyl-4-{3-[4-(indolin-1-yl-carbonyl)-phenyl]-propargylamino}benzamidine and trifluoroacetic acid.

Yield: 42% of theory, $R_f$ value: 0.23 (Reversed phase silica gel RP-8; methanol/5% NaCl solution=60:40)

$C_{25}H_{22}N_4O \times CF_3COOH$ (394.48/508.50)

Mass spectrum: $(M+H)^+=395$

EXAMPLE 58 rac-4-{3-[4-(2-hydroxymethyl-pyrrolidinocarbonyl)-phenyl]-propargylamino}benzamidine Prepared analogously to Example 2 from rac-N-tert-butoxycarbonyl-4-{3-[4-(2-hydroxymethyl-pyrrolidinocarbonyl)-phenyl]-propargylamino}benzamidine and trifluoroacetic acid.

Yield: 51% of theory, $R_f$ value: 0.26 (silica gel; methylene chloride/ethanol=4:1 and 1 drop of acetic acid)

$C_{22}H_{24}N_4O_2 \times CF_3COOH$ (376.46/490.48)

Mass spectrum:
$(M+H)^+=377$
$(M+2H)^{++}=189$
$(M+Na+H)^{++}=200$

EXAMPLE 59 rac-4-{3-[4-(2-ethoxycarbonylmethyl-pyrrolidinocarbonyl)-3-methyl-phenyl]-propargylamino}benzamidine Prepared analogously to Example 2 from rac-N-tert-butoxycarbonyl-4-{3-[4-(2-ethoxycarbonylmethyl-pyrrolidinocarbonyl)-3-methyl-phenyl]-propargylamino}benzamidine and trifluoroacetic acid.

Yield: 66% of theory, $R_f$ value: 0.27 (silica gel; methylene chloride/ethanol=4:1 and 1 drop of acetic acid)

$C_{26}H_{30}N_4O_3 \times CF_3COOH$ (446.55/560.57)

Mass spectrum:
$(M+H)^+=447$
$(M+2H)^{++}=224$
$(M+Na+H)^{++}=235$

EXAMPLE 60 rac-4-{3-[4-(2-(2-ethoxycarbonyl-ethyl)-pyrrolidinocarbonyl)-3-methyl-phenyl]-propargylamino}benzamidine Prepared analogously to Example 2 from rac-N-tert-butoxycarbonyl-4-{3-[4-(2-(2-ethoxycarbonyl-ethyl)-3-methyl-pyrrolidinocarbonyl)-phenyl]-propargylamino}benzamidine and trifluoroacetic acid.

Yield: 56% of theory, $R_f$ value: 0.28 (silica gel; methylene chloride/ethanol=4:1 and 1 drop of acetic acid)

$C_{27}H_{32}N_4O_3 \times CF_3COOH$ (460.58/574.61)

Mass spectrum:
$(M+H)^+=461$
$(M+Na+H)^{++}=242$

EXAMPLE 61 rac-4-{3-[4-(2-methoxycarbonyl-pyrrolidinocarbonyl)-phenyl]-propargylamino}benzamidine Prepared analogously to Example 2 from rac-N-tert-butoxycarbonyl-4-{3-[4-(2-methoxycarbonyl-pyrrolidinocarbonyl)-phenyl]-propargylamino}benzamidine and trifluoroacetic acid.

Yield: 69% of theory, $R_f$ value: 0.26 (silica gel; methylene chloride/ethanol=4:1 and 1 drop of acetic acid)

$C_{23}H_{24}N_4O_3 \times CF_3COOH$ (404.47/518.49)

Mass spectrum:
(M+H)$^+$=405
(M+Na+H)$^{++}$=214
(M+2H)$^{++}$=203

EXAMPLE 62 rac-4-{3-[4-(2-ethoxycarbonylmethyloxymethyl-pyrrolidino-carbonyl)-phenyl]-3-methyl-propargylamino}benzamidine Prepared analogously to Example 2 from rac-N-tert-butoxycarbonyl-4-{3-[4-(2-ethoxycarbonylmethyloxymethyl-pyrrolidinocarbonyl)-3-methyl-phenyl]-propargylamino}benzamidine and trifluoroacetic acid.

Yield: 76% of theory,
R$_f$ value: 0.26 (silica gel; methylene chloride/ethanol=4:1 and 1 drop of acetic acid)
C$_{27}$H$_{32}$N$_4$O$_4$×CF$_3$COOH (476.58/590.61)
Mass spectrum:
(M+H)$^+$=477
(M+Na+H)$^{++}$=250

EXAMPLE 63 rac4-{3-[4-(2-ethoxycarbonylmethylaminocarbonylmethyl-pyrrolidinocarbonyl)-3-methyl-phenyl]-propargylamino}benzamidine Prepared analogously to Example 2 from rac-N-tert-butoxycarbonyl-4-{3-[4-(2-ethoxycarbonylmethylaminocarbonyl-methyl-pyrrolidinocarbonyl)-3-methyl-phenyl]-propargylamino}-benzamidine and trifluoroacetic acid.

Yield: 60% of theory,
R$_f$ value: 0.21 (silica gel; methylene chloride/ethanol=4:1 and one drop of acetic acid)
C$_{28}$H$_{33}$N$_5$O$_4$×CF$_3$COOH (503.61/617.63)
Mass spectrum:
(M+H)$^+$=504
(M+Na+H)$^{++}$=263.7
(M+2H)$^{++}$=252.7

EXAMPLE 64

4-{3-[3-(2-ethoxycarbonyl-ethyl)-4-pyrrolidinocarbonyl-phenyl]propargylamino}benzamidine Prepared analogously to Example 2 from N-tert-butoxycarbonyl-4-{3-[3-(2-ethoxycarbonyl-ethyl)-4-pyrrolidinocarbonyl-phenyl]propargylamino}benzamidine and trifluoroacetic acid.

Yield: 30% of theory,
R$_f$ value: 0.16 (silica gel; methylene chloride/ethanol=4:1)
C$_{26}$H$_{30}$N$_4$O$_3$×CF$_3$COOH (446.55/560.57)
Mass spectrum:
(M+H)$^+$=447
(M+2H)$^{++}$=224
(M+Na+H)$^{++}$=235

EXAMPLE 65 rac-4-{3-[3-(N-ethoxycarbonylmethyl-N-methyl-aminomethyl)-4-(2-methyl-pyrrolidinocarbonyl)-phenyl]-propargylamino}benzamidine Prepared analogously to Example 2 from rac-N-tert-butoxycarbonyl-4-{3-[3-(N-ethoxycarbonylmethyl-N-methyl-aminomethyl)-4-(2-methyl-pyrrolidinocarbonyl)-phenyl]propargylamino benzamidine and trifluoroacetic acid.

Yield: 49% of theory,
R$_f$ value: 0.23 (Reversed phase silica gel RP-8; methanol/5% NaCl solution=60:40)
C$_{28}$H$_{35}$N$_5$O$_3$×CF$_3$COOH (489.62/603.64)
Mass spectrum:
(M+H)$^+$=490
(M+2H)$^{++}$=245.5
(M+Na+H)$^{++}$=256.5

EXAMPLE 66

4-[3-(3-ethoxycarbonylmethyloxymethyl-4-pyrrolidinocarbonyl-phenyl)propargylamino]benzamidine Prepared analogously to Example 2 from rac-N-tert-butoxycarbonyl-4-[3-(3-ethoxycarbonylmethyloxymethyl-4-pyrrolidinocarbonyl-phenyl)propargylamino]benzamidine and trifluoroacetic acid.

Yield: 96% of theory,
R$_f$ value: 0.23 (Reversed phase silica gel RP-8; methanol/5% NaCl solution=60:40)
C$_{26}$H$_{30}$N$_4$O$_4$×CF$_3$COOH (462.55/576.57)
Mass spectrum:
(M+H)$^+$=463
(M+2H)$^{++}$=232
(M+Na+H)$^{++}$=243

EXAMPLE 67

4-[3-(3-ethoxycarbonylmethyl-4-pyrrolidinocarbonyl-phenyl)propargylamino]benzamidine Prepared analogously to Example 2 from N-tert-butoxycarbonyl-4-[3-(3-ethoxycarbonylmethyl-4-pyrrolidinocarbonyl-phenyl)propargylamino]benzamidine and trifluoroacetic acid.

Yield: 85% of theory,
R$_f$ value: 0.45 (silica gel; methylene chloride/ethanol=4:1+1 drop of acetic acid)
C$_{25}$H$_{28}$N$_4$O$_3$×CF$_3$COOH (432.53/546.55)
Mass spectrum: (M+H)$^+$=433

EXAMPLE 68

4-[3-(3-ethoxycarbonylmethylaminocarbonylmethyl-4-pyrrolidinocarbonyl-phenyl)propargylamino]benzamidine Prepared analogously to Example 2 from rac-N-tert-butoxycarbonyl-4-[3-(3-ethoxycarbonylmethylaminocarbonyl-methyl-4-pyrrolidinocarbonyl-phenyl)propargylamino]benzamidine and trifluoroacetic acid.

Yield: 91% of theory,
R$_f$ value: 0.35 (silica gel; methylene chloride/ethanol=4:1+1 drop of acetic acid)
C$_{27}$H$_{31}$N$_5$O$_4$×CF$_3$COOH (489.58/603.60)
Mass spectrum: (M+H)$^+$=490

EXAMPLE 69

4-{3-[4-[phenyl-(ethoxycarbonylmethyloxyimino)-methylene]-phenyl]propargylamino}benzamidine a) 4-{3-[4-[phenyl-(hydroxycarbonylmethyloxyimino)-methylene]-phenyl]propargylamino}benzonitrile A mixture of 0.50 g (1.5 mmol) of 4-[3-(4-phenylcarbonyl-phenyl)-propargylamino]benzonitrile, 0.50 g (2.3 mmol) of carboxymethoxylamine hydrochloride, 0.32 ml (2.3 mmol) of triethylamine, 3 g of 3 Å molecular sieves and 3 g of 4 Å molecular sieves in 45 ml of methanol/toluene (2:1) is heated to boiling for one week. Then it is filtered, concentrated and purified by flash chromatography (silica gel; petroleum ether/ethyl acetate=2:1 to ethyl acetate/acetic acid=200:1).

Yield: 75% of theory, $R_f$ value: <0.1 (silica gel; ethyl acetate/petroleum ether=1:1)

b) 4-{3-[4-[phenyl-(ethoxycarbonylmethyloxvimino)-methylene]-phenyl]propargylamino}benzamidine Prepared analogously to Example 4c from 4-{3-[4-[phenyl-(hydroxycarbonylmethyloxyimino)-methylene]-phenyl]propargylamino}benzonitrile, ethanol saturated with hydrogen chloride gas and ammonium carbonate.

Yield: 27% of theory, $R_f$ value: 0.23 (silica gel; methylene chloride/ethanol=4:1+1 drop of acetic acid)

$C_{27}H_{26}N_4O_3 \times HCl$ (454.53/490.99)

Mass spectrum: $(M+H)^+=455$

EXAMPLE 70

4-{3-[4-[N-(2-ethoxycarbonyl-ethyl)-N-isopropyl-amino-carbonyl]-3-methyl-phenyl]propargylamino}benzamidine Prepared analogously to Example 2 from rac-N-tert-butoxycarbonyl-4-{3-[4-[N-(2-ethoxycarbonyl-ethyl)-N-isopropyl-aminocarbonyl]-3-methyl-phenyl]propargylamino}benzamidine and trifluoroacetic acid.

Yield: 44% of theory, $R_f$ value: 0.1 (silica gel; methylene chloride/ethanol=4:1)

$C_{26}H_{32}N_4O_3 \times CF_3COOH$ (448.56/562.59)

Mass spectrum: $(M+H)^+=449$

EXAMPLE 71

4-{3-[4-[N-(2-ethoxycarbonyl-ethyl)-N-methyl-aminocarbonyl]-3-methyl-phenyl]propargylamino}benzamidine Prepared analogously to Example 2 from rac-N-tert-butoxycarbonyl-4-{3-[4-[N-(2-ethoxycarbonyl-ethyl)-N-isopropyl-aminocarbonyl]-3-methyl-phenyl]propargylamino}benzamidine and trifluoroacetic acid.

Yield: 16% of theory, $R_f$ value: 0.1 (silica gel; methylene chloride/ethanol=4:1)

$C_{24}H_{28}N_4O_3 \times CF_3COOH$ (420.52/534.54)

Mass spectrum $(M+H)^+=421$

EXAMPLE 72

4-{3-[4-[N-(2-methoxycarbonyl-ethyl)-N-pyridin-2-yl-aminocarbonyl]-2,5-dimethyl-phenyl]propargylamino}benzamidine Prepared analogously to Example 2 from rac-N-tert-butoxycarbonyl-4-{3-[4-[N-(2-methoxycarbonyl-ethyl)-N-pyridin-2-yl-aminocarbonyl]-2,5-dimethyl-phenyl]propargylamino}benzamidine and trifluoroacetic acid.

Yield: 48% of theory, $R_f$ value: 0.25 (silica gel; methylene chloride/ethanol=4:1)

$C_{28}H_{29}N_5O_3 \times 2CF_3COOH$ (483.58/711.62)

Mass spectrum: $(M+H)^+=484$

EXAMPLE 73 rac-4-{3-[4-(2-hydroxycarbonylmethyl-pyrrolidinocarbonyl)-3-methyl-phenyl]-propargylamino}benzamidine Prepared analogously to Example 3 from rac-4-{3-[4-(2-ethoxycarbonylmethyl-pyrrolidinocarbonyl)-3-methyl-phenyl]-propargylamino}benzamidine, lithium hydroxide and subsequent treatment with ammonium chloride.

Yield: 53% of theory, $R_f$ value: 0.36 (Reversed phase silica gel RP-8; methanol/5% NaCl solution=60:40)

$C_{24}H_{26}N_4O_3 \times HCl$ (418.50/454.96)

Mass spectrum:

$(M+H)^+=419$ $(M+Na)^+=441$ $(M+Na+H)^{++}=232$

EXAMPLE 74 rac-4-{3-[4-(2-(2-hydroxycarbonyl-ethyl)-pyrrolidinocarbonyl)-3-methyl-phenyl]-propargylamino}benzamidine Prepared analogously to Example 3 from rac-4-{3-[4-(2-(2-ethoxycarbonyl-ethyl)-pyrrolidinocarbonyl)-3-methyl-phenyl]-propargylamino}benzamidine, lithium hydroxide and subsequent treatment with ammonium chloride.

Yield: 67% of theory, $R_f$ value: 0.39 (Reversed phase silica gel RP-8; methanol/5% NaCl solution=60:40)

$C_{25}H_{28}N_4O_3 \times HCl$ (432.52/468.98)

Mass spectrum:

$(M+H)^+=433$ $(M+Na)^+=455$ $(M+2Na)^{++}=239$

EXAMPLE 75 rac-4-{3-[4-(2-hydroxycarbonyl-pyrrolidinocarbonyl)-phenyl]-propargylamino}benzamidine Prepared analogously to Example 3 from rac-4-{3-[4-(2-methoxycarbonyl-pyrrolidinocarbonyl)-phenyl]-propargylamino}benzamidine, lithium hydroxide and subsequent treatment with ammonium chloride.

Yield: 42% of theory, $R_f$ value: 0.32 (Reversed phase silica gel RP-8; methanol/5% NaCl solution=60:40)

$C_{22}H_{22}N_4O_3 \times HCl$ (390.45/426.91)

Mass spectrum:

$(M+H)^+=391$ $(M+Na)^+=413$ $(M+2Na)^{++}=218$

EXAMPLE 76 rac-4-{3-[4-(2-hydroxycarbonylmethyloxymethyl-pyrrolidino-carbonyl)-3-methyl-phenyl]-propargylamino}benzamidine Prepared analogously to Example 3 from rac-4-{3-[4-(2-ethoxycarbonylmethyloxymethyl-pyrrolidinocarbonyl)-3- methyl-phenyl]-propargylamino}benzamidine, lithium hydroxide and subsequent treatment with ammonium chloride.

Yield: 30% of theory, $R_f$ value: 0.4 (Reversed phase silica gel RP-18; methanol/5% NaCl solution=60:40)

$C_{25}H_{28}N_4O_4 \times HCl$ (448.53/484.99)

Mass spectrum:

$(M+H)^+=449$ $(M-H)^-=447$

EXAMPLE 77 rac-4-{3-[4-(2-hydroxycarbonylmethylaminocarbonylmethyl-pyrrolidinocarbonyl)-3-methyl-phenyl]-propargylamino}benzamidine Prepared analogously to Example 2 from rac-4-{3-[4-(2-ethoxycarbonylmethylaminocarbonylmethyl-pyrrolidinocarbonyl)-3-methyl-phenyl]-propargylamino}benzamidine, lithium hydroxide and subsequent treatment with ammonium chloride.

Yield: 80% of theory, $R_f$ value: 0.38 (Reversed phase silica gel RP-8; methanol/5% NaCl solution=60:40)

$C_{26}H_{29}N_5O_4 \times HCl$ (475.55/512.01)

Mass spectrum:

$(M+H)^+=476$ $(M-H)^-=474$

EXAMPLE 78

4-{3-[3-(2-hydroxycarbonyl-ethyl)4-pyrrolidinocarbonyl-phenyl]propargylamino}benzamidine Prepared analogously to Example 3 from 4-{3-[3-(2-ethoxycarbonyl-ethyl)-4-pyrrolidinocarbonyl-phenyl]propargylamino}benzamidine, lithium hydroxide and subsequent treatment with ammonium chloride.

Yield: 84% of theory, $R_f$ value: >0.1 (silica gel; methylene chloride/ethanol=4:1)

$C_{24}H_{26}N_4O_3 \times HCl$ (418.50/454.96)

Mass spectrum:

$(M+H)^+=419$ $(M+2H)^{++}=210$ $(M+Na+H)^{++}=221$ $(M+2Na)^{++}=232$

EXAMPLE 79

4-{3-[3-(2-hydroxycarbonyl-vinyl)-4-pyrrolidinocarbonyl-phenyl]propargylamino}benzamidine Prepared analogously to Example 3 from 4-{3-[3-(2-ethoxycarbonyl-vinyl)-4-pyrrolidinocarbonyl-phenyl]propargylamino}benzamidine, lithium hydroxide and subsequent treatment with ammonium chloride.

Yield: 45% of theory, $R_f$ value: >0.1 (silica gel; methylene chloride/ethanol=4:1)

$C_{24}H_{24}N_4O_3 \times HCl$ (416.48/452.94)

Mass spectrum:

$(M+H)^+=417$ $(M+Na)^+=439$ $(M+Na+H)^{++}=220$ $(M+2Na)^{++}=231$

EXAMPLE 80 rac-4-{3-[3-(N-hydroxycarbonylmethyl-N-methyl-aminomethyl)-4-(2-methyl-pyrrolidinocarbonyl)-phenyl]propargylamino}benzamidine Prepared analogously to Example 3 from rac-4-{3-[3-(N-ethoxycarbonylmethyl-N-methyl-aminomethyl)-4-(2-methyl-pyrrolidinocarbonyl)-phenyl]propargylamino}benzamidine, lithium hydroxide and subsequent treatment with ammonium chloride.

Yield: 30% of theory, $R_f$ value: 0.42 (Reversed phase silica gel RP-8; methanol/5% NaCl solution=60:40)

$C_{26}H_{31}N_5O_3 \times HCl$ (461.57/498.03)

Mass spectrum:

$(M+H)^+=462$ $(M-H)^-=460$

EXAMPLE 81

4-[3-(3-hydroxycarbonylmethyloxymethyl-4-pyrrolidinocarbonyl-phenyl)propargylamino]benzamidine Prepared analogously to Example 3 from 4-[3-(3-ethoxycarbonylmethyloxymethyl-4-pyrrolidinocarbonyl-phenyl)propargylamino]benzamidine, lithium hydroxide and subsequent treatment with ammonium chloride.

Yield: 21% of theory, $R_f$ value: 0.23 (Reversed phase silica gel RP-8; methanol/5% NaCl solution=60:40)

$C_{24}H_{26}N_4O_4 \times HCl$ (434.50/470.96)

Mass spectrum:

$(M+H)^+=435$ $(M-H)^-=433$

EXAMPLE 82

4-[3-(3-hydroxycarbonylmethyl-4-pyrrolidinocarbonyl-phenyl)-propargylamino]benzamidine Prepared analogously to Example 3 from 4-[3-(3-ethoxycarbonylmethyl-4-pyrrolidinocarbonyl-phenyl)propargylamino]benzamidine, lithium hydroxide and subsequent treatment with ammonium chloride.

Yield: 62% of theory, $R_f$ value: 0.45 (Reversed phase silica gel RP-8; methanol/5% NaCl solution=60:40)

$C_{23}H_{24}N_4O_3 \times HCl$ (404.47/440.93)

Mass spectrum:

$(M+H)^+=405$ $(M-H)^-=403$

EXAMPLE 83

4-[3-(3-hydroxycarbonylmethylaminocarbonylmethyl-4-pyrrolidinocarbonyl-phenyl)propargylamino]benzamidine Prepared analogously to Example 3 from 4-[3-(3-ethoxycarbonylmethylaminocarbonylmethyl-4- pyrrolidinocarbonyl-phenyl)propargylamino}benzamidine, lithium hydroxide and subsequent treatment with ammonium chloride.

Yield: 42% of theory, $R_f$ value: 0.45 (Reversed phase silica gel RP-8; methanol/5% NaCl solution=60:40)

$C_{25}H_{27}N_5O_4 \times HCl$ (461.53/497.99)

Mass spectrum:

$(M+H)^+=462$ $(M+Na)^+=484$

EXAMPLE 84

4-{3-[3-(hydroxycarbonylmethyloxyimino) methylene-4-pyrrolidinocarbonyl-phenyl] propargylamino}benzamidine Prepared analogously to Example 2 from rac-N-tert-butoxycarbonyl-4-{3-[3-(hydroxycarbonylmethyloxyimino)-methylene-4-pyrrolidinocarbonyl-phenyl]propargylamino}benzamidine and trifluoroacetic acid.

Yield: 42% of theory, $R_f$ value: 0.4 (Reversed phase silica gel RP-8; methanol/5% NaCl solution=60:40)

$C_{24}H_{25}N_5O_4 \times CF_3COOH$ (447.50/561.52)

Mass spectrum:

$(M+H)^+=448$ $(M+Na)^+=470$ $(M+2H)^{++}=224.5$ $(M+Na+H)^{++}=235.7$ $(M+2Na)^{++}=246.6$

EXAMPLE 85 rac-4-{3-[2-methoxy-4-(2-methyl-pyrrolidinocarbonyl)-phenyl]-propargylamino}benzamidine Prepared analogously to Example 2 from rac-N-tert-butoxycarbonyl4-{3-[2-methoxy4-(2-methyl-pyrrolidinocarbonyl)-phenyl]propargylamino}benzamidine and trifluoroacetic acid.

Yield: 90% of theory, $R_f$ value: 0.38 (silica gel; methylene chloride/ethanol=4:1 and one drop of acetic acid)

$C_{23}H_{26}N_4O_2 \times CF_3COOH$ (390.49/504.51)

Mass spectrum:

$(M+H)^+=391$ $(M+2H)^{++}=196$

EXAMPLE 86

4-[3-(3-methoxy-4-pyrrolidinocarbonyl-phenyl) propargylamino]benzamidine

Prepared analogously to Example 2 from N-tert-butoxycarbonyl-4-[3-(3-methoxy4-pyrrolidinocarbonyl-phenyl)propargylamino]benzamidine and trifluoroacetic acid.

Yield: 58% of theory, $R_f$ value: 0.20 (silica gel; methylene chloride/ethanol=4:1 and one drop of acetic acid)

$C_{22}H_{24}N_4O_2 \times CF_3COOH$ (376.46/490.48)

Mass spectrum: $(M+H)^+=377$

EXAMPLE 87

4-[3-(3-hydroxy-4-pyrrolidinocarbonyl-phenyl) propargylamino]benzamidine

Prepared analogously to Example 2 from N-tert-butoxycarbonyl-4-[3-(3-hydroxy-4-pyrrolidinocarbonyl-phenyl)propargylamino]benzamidine and trifluoroacetic acid.

Yield: 54% of theory, $R_f$ value: 0.46 (Reversed phase silica gel RP-8; methanol/5% NaCl solution=60:40)

$C_{21}H_{22}N_4O_2 \times CF_3COOH$ (362.44/476.46)

Mass spectrum: $(M+H)^+=363$

EXAMPLE 88 rac-4-{3-[3-hydroxymethyl-4-(2-methyl-pyrrolidinocarbonyl)-phenyl] propargylamino}benzamidine Prepared analogously to Example 2 from rac-N-tert-butoxycarbonyl-4-{3-[3-hydroxymethyl-4-(2-methyl-pyrrolidinocarbonyl)-phenyl]propargylamino}benzamidine and trifluoroacetic acid.

Yield: 57% of theory, $R_f$ value: 0.54 (Reversed phase silica gel RP-8; methanol/5% NaCl solution=60:40)

$C_{23}H_{26}N_4O_2 \times CF_3COOH$ (390.49/504.51)

Mass spectrum: $(M+H)^+=391$

EXAMPLE 89

4-[3-(3-formyl-4-pyrrolidinocarbonyl-phenyl) propargylamino]benzamidine

Prepared analogously to Example 2 from N-tert-butoxycarbonyl-4-[3-(3-formyl-4-pyrrolidinocarbonyl-phenyl)propargylamino]benzamidine and trifluoroacetic acid.

Yield: 71% of theory, $R_f$ value: 0.4 (Reversed phase silica gel RP-8; methanol/5% NaCl solution=60:40)

$C_{22}H_{22}N_4O_2 \times CF_3COOH$ (374.45/488.47)

Mass spectrum: $(M+H)^+=375$

EXAMPLE 90

4-[3-(3-aminocarbonylaminoiminomethylene-4-pyrrolidinocarbonyl-phenyl)propargylamino] benzamidine Prepared analogously to Example 2 from N-tert-butoxycarbonyl-4-[3-(3-aminocarbonylaminoiminomethylen-4-pyrrolidinocarbonyl-phenyl)propargylamino]benzamidine and trifluoroacetic acid.

Yield: 83% of theory, $R_f$ value: 0.4 (Reversed phase silica gel RP-8; methanol/5% NaCl solution=60:40)

$C_{23}H_{25}N_7O_2 \times CF_3COOH$ (431.50/545.53)

Mass spectrum:

$(M+H)^+=432$ $(M+Na+H)^{++}=227.8$

EXAMPLE 91

4-[1-methyl-3-(4-pyrrolidinocarbonyl-phenyl) propargylamino]benzamidine

Prepared analogously to Example 4c from 4-[1-methyl-3-(4-pyrrolidinocarbonyl-phenyl)propargylamino] benzonitrile, ethanol saturated with hydrogen chloride gas and ammonium carbonate.

Yield: 78% of theory, $R_f$ value: 0.57 (silica gel; ethyl acetate/ethanol/ammonia= 50:45:5)

$C_{22}H_{24}N_4O \times HCl$ (360.47/396.93)

Mass spectrum:

$(M+H)^+=361$ $(M+Cl)^-=395/397$ $(M+Cl+HCl)^-=431/433/435N$

EXAMPLE 92

4-[3-(4-piperidinocarbonyl-phenyl)propargylamino] benzamidine

Prepared analogously to Example 4c from 4-[3-(4-piperidinocarbonyl-phenyl)propargylamino]benzonitrile, ethanol saturated with hydrogen chloride gas and ammonium carbonate.

Yield: 65% of theory, $R_f$ value: 0.25 (Reversed phase silica gel RP-8; methanol/ 5% NaCl solution=60:40)

$C_{22}H_{24}N_4O \times HCl$ (360.47/396.93)

Mass spectrum: $M^+=360$

EXAMPLE 93 rac-4-{3-[4-(4-methylpiperidinocarbonyl)-phenyl] propargylamino}benzamidine

Prepared analogously to Example 2 from rac-N-tert-butoxycarbonyl-4-{3-[4-(4-methylpiperidinocarbonyl)-phenyl]propargylamino}benzamidine and trifluoroacetic acid.

Yield: 70% of theory, $R_f$ value: 0.27 (Reversed phase silica gel RP-8; methanol/ 5% NaCl solution=60:40)

$C_{23}H_{26}N_4O \times CF_3COOH$ (374.49/488.51)

Mass spectrum: $(M+H)^+=375$

EXAMPLE 94

4-[3-(4-Azetidinocarbonyl-phenyl)propargylamino] benzamidine

Prepared analogously to Example 2 from N-tert-butoxycarbonyl-4-[3-(4-azetidinocarbonyl-phenyl) propargylamino]benzamidine and trifluoroacetic acid.

Yield: 72% of theory, $R_f$ value: 0.21 (silica gel; methylene chloride/ethanol 4:1 and one drop of acetic acid)

$C_{20}H_{20}N_4O \times CF_3COOH$ (332.41/446.43)

Mass spectrum: $(M+H)^+=333$

EXAMPLE 95

4-[3-(3-methyl-4-morpholinocarbonyl-phenyl) propargylamino]benzamidine

Prepared analogously to Example 2 from N-tert-butoxycarbonyl-4-[3-(3-methyl4-morpholinocarbonyl-phenyl)propargylamino]benzamidine and trifluoroacetic acid.

Yield: 90% of theory, $R_f$ value: 0.32 (silica gel; ethyl acetate/ethanol/ammonia= 50:45:5)

$C_{22}H_{24}N_4O_2 \times CF_3COOH$ (376.47/490.49)

Mass spectrum: $(M+H)^+=377$

EXAMPLE 96

4-[3-(2-methyl-4-morpholinocarbonyl-phenyl) propargylamino]benzamidine

Prepared analogously to Example 2 from N-tert-butoxycarbonyl-4-[3-(2-methyl-4-morpholinocarbonyl-phenyl)propargylamino]benzamidine and trifluoroacetic acid.

Yield: 80% of theory, $R_f$ value: 0.38 (silica gel; ethyl acetate/ethanol/ammonia= 50:45:5)

$C_{22}H_{24}N_4O_2 \times CF_3COOH$ (376.47/490.49)

Mass spectrum: $(M+H)^+=377$

EXAMPLE 97

4-{3-[4-(4-methylpiperazinocarbonyl)-phenyl] propargylamino}benzamidine

Prepared analogously to Example 2 from N-tert-butoxycarbonyl-4-{3-[4-(4-methylpiperazinocarbonyl)-phenyl]propargylamino}benzamidine and trifluoroacetic acid.

Yield: 87% of theory, $R_f$ value: 0.59 (Reversed phase silica gel RP-8; methanol/ 5% NaCl solution=60:40)

$C_{22}H_{25}N_5O \times 2CF_3COOH$ (375.48/603.52)

Mass spectrum: $(M+H)^+=376$

EXAMPLE 98

4-[3-(4-dimethylaminocarbonyl-phenyl) propargylamino]-benzamidine

Prepared analogously to Example 2 from N-tert-butoxycarbonyl-4-[3-(4-dimethylaminocarbonyl-phenyl) propargylamino]-benzamidine and trifluoroacetic acid.

Yield: 66% of theory, $R_f$ value: 0.21 (silica gel; methylene chloride/ethanol 4:1 and one drop of acetic acid)

$C_{19}H_{20}N_4O \times CF_3COOH$ (320.40/434.42)

Mass spectrum: $(M+H)^+=321$

EXAMPLE 99

4-[3-(2,5-dimethyl-4-dimethylaminocarbonyl-phenyl)propargylamino]benzamidine

Prepared analogously to Example 2 from N-tert-butoxycarbonyl-4-[3-(2,5-dimethyl-4-dimethylaminocarbonyl-phenyl)propargyl-amino] benzamidine and trifluoroacetic acid.

Yield: 54% of theory, $R_f$ value: 0.13 (silica gel; methylene chloride/ethanol=4:1)

$C_{21}H_{24}N_4O \times CF_3COOH$ (348.46/462.49)

Mass spectrum: $(M+H)^+=349$

EXAMPLE 100

4-[3-(4-diethylamineocarbonyl-3-methyl-phenyl)propargylamino]benzamidine

Prepared analogously to Example 2 from N-tert-butoxycarbonyl-4-[3-(4-diethylamineocarbonyl-3-methyl-phenyl)propargylamino]benzamidine and trifluoroacetic acid.

Yield: 80% of theory, $R_f$ value: 0.29 (silica gel; methylene chloride/ethanol=4:1 and one drop of acetic acid)

$C_{22}H_{26}N_4O \times CF_3COOH$ (362.46/476.50)

Mass spectrum: $(M+H)^+=363$

EXAMPLE 101

4-{3-[4-(N-isopropyl-N-methyl-aminocarbonyl)-2,5-dimethyl-phenyl]propargylamino}benzamidine Prepared analogously to Example 2 from N-tert-butoxycarbonyl-4-{3-[4-(N-isopropyl-N-methyl-aminocarbonyl)-2,5-dimethyl-phenyl]propargylamino}benzamidine and trifluoroacetic acid.

Yield: 92% of theory, $R_f$ value: 0.15 (silica gel; methylene chloride/ethanol=4:1)

$C_{23}H_{28}N_4O \times CF_3COOH$ (376.51/490.53)

Mass spectrum: $(M+H)^+=377$

EXAMPLE 102

4-{3-[4-(N-tert-butyl-N-methyl-aminocarbonyl)-2,5-dimethyl-phenyl]propargylamino}benzamidine Prepared analogously to Example 2 from N-tert-butoxycarbonyl-4-{3-[4-(N-tert-butyl-N-methyl-aminocarbonyl)-2,5-dimethyl-phenyl]propargylamino}benzamidine and trifluoroacetic acid.

Yield: 41% of theory, $R_f$ value: 0.3 (silica gel; methylene chloride/ethanol=4:1)

$C_{24}H_{30}N_4O \times CF_3COOH$ (390.54/504.56)

Mass spectrum: $(M+H)^+391$

EXAMPLE 103

4-[3-(4-trimethylhydrazinocarbonyl-3-methyl-phenyl)propargylamino]benzamidine

Prepared analogously to Example 2 from N-tert-butoxycarbonyl-4-[3-(4-trimethylhydrazinocarbonyl-3-methyl-phenyl)propargylamino]benzamidine and trifluoroacetic acid.

Yield: 7% of theory, $R_f$ value: 0.3 (Reversed phase silica gel RP-8; methanol/5% NaCl solution=60:40)

$C_{21}H_{25}N_5O \times 2CF_3COOH$ (363.47/591.51)

Mass spectrum: $(M+H)^+=364$

EXAMPLE 104

4-{3-[4-(N-(2-dimethylamino-ethyl)-N-methyl-aminocarbonyl)-phenyl]propargylamino}benzamidine Prepared analogously to Example 2 from N-tert-butoxycarbonyl-4-{3-[4-(N-(2-dimethylamino-ethyl)-N-methyl-aminocarbonyl)-phenyl]propargylamino}benzamidine and trifluoroacetic acid.

Yield: 23% of theory, $R_f$ value: 0.51 (Reversed phase silica gel RP-8; methanol/5% NaCl solution=60:40)

$C_{22}H_{27}N_5O \times 2CF_3COOH$ (377.50/605.54)

Mass spectrum:

$(M+H)^+=378$ $(M+2H)^{++}=189.7$

EXAMPLE 105

4-{3-[4-(N-(3-dimethylamino-propyl)-N-methyl-aminocarbonyl)-3-methyl-phenyl]propargylamino}benzamidine Prepared analogously to Example 2 from N-tert-butoxycarbonyl4-{3-[4-(N-(3-dimethylamino-propyl)-N-methyl-aminocarbonyl)-3-methyl-phenyl]propargylamino}benzamidine and trifluoroacetic acid.

Yield: 5% of theory, $R_f$ value: 0.5 (Reversed phase silica gel RP-8; methanol/5% NaCl solution=60:40)

$C_{24}H_{31}N_5O \times 2CF_3COOH$ (405.56/633.60)

Mass spectrum: $(M+2H)^{++}=203.8$

EXAMPLE 106

4-{3-[4-(N-cyclopentyl-N-methyl-aminocarbonyl)-3-methyl-phenyl]propargylamino}benzamidine Prepared analogously to Example 2 from N-tert-butoxycarbonyl-4-{3-[4-(N-cyclopentyl-N-methyl-aminocarbonyl)-3-methyl-phenyl]propargylamino}benzamidine and trifluoroacetic acid.

Yield: 84% of theory, $R_f$ value: 0.3 (silica gel; methylene chloride/ethanol=4:1)

$C_{24}H_{28}N_4O \times CF_3COOH$ (388.52/502.54)

Mass spectrum: $(M+H)^+=389$

EXAMPLE 107

4-{3-[4-(pyrrolidine-3-ylamino-carbonyl)-3-methylphenyl]propargylamino}benzamidine Prepared analogously to Example 2 from N-tert-butoxycarbonyl-4-{3-[4-(1-tert-butoxycarbonylpyrrolidin-3-yl-aminocarbonyl)-3-methyl-phenyl]propargylamino}benzamidine and trifluoroacetic acid, with the residue subsequently being taken up in ethanol and precipitated with ethereal hydrochloric acid.

Yield: 33% of theory, $R_f$ value: 0.41 (Reversed phase silica gel RP-8; methanol/5% NaCl solution=60:40)

$C_{22}H_{25}N_5O \times 2HCl$ (375.49/448.41)

Mass spectrum:

$(M+H)^+=376$ $(M+2H)^+=185.5$

EXAMPLE 108

4-{3-[5-(N-cyclopentyl-N-methyl-aminocarbonyl)-2-methyl-phenyl]propargylamino}benzamidine Prepared analogously to Example 2 from N-tert-butoxycarbonyl-4-{3-[5-(N-cyclopentyl-N-methyl-aminocarbonyl)-2-methyl-phenyl]propargylamino}benzamidine and trifluoroacetic acid.

Yield: 70% of theory, $R_f$ value: 0.21 (silica gel; methylene chloride/ethanol= 4:1)

$C_{24}H_{28}N_4O \times CF_3COOH$ (388.52/502.54)

Mass spectrum: (M+H)$^+$=389

EXAMPLE 109

4-{3-[5-(N-methyl-N-(2-phenyl-ethyl)-aminocarbonyl)-2-methyl-phenyl]propargylamino}benzamidine Prepared analogously to Example 2 from N-tert-butoxycarbonyl-4-{3-[5-(N-methyl-N-(2-phenyl-ethyl)-aminocarbonyl)-2-methyl-phenyl]propargylamino}benzamidine and trifluoroacetic acid.

Yield: 54% of theory, $R_f$ value: 0.22 (silica gel; methylene chloride/ethanol= 4:1)

$C_{27}H_{28}N_4O \times CF_3COOH$ (424.56/538.58)

Mass spectrum: (M+H)$^+$=425

EXAMPLE 110

4-{3-[5-(N-methyl-N-benzyl-aminocarbonyl)-2-methyl-phenyl]-propargylamino}benzamidine Prepared analogously to Example 2 from N-tert-butoxycarbonyl-4-{3-[5-(N-methyl-N-benzyl-aminocarbonyl)-2-methyl-phenyl]propargylamino}benzamidine and trifluoroacetic acid.

Yield: 55% of theory, $R_f$ value: 0.25 (silica gel; methylene chloride/ethanol= 4:1)

$C_{26}H_{26}N_4O \times CF_3COOH$ (410.53/524.55)

Mass spectrum: (M+H)$^+$=411

EXAMPLE 111

4-{3-[5-(2-phenyl-ethylaminocarbonyl)-2-methyl-phenyl]propargylamino}benzamidine Prepared analogously to Example 2 from N-tert-butoxycarbonyl-4-{3-[5-(2-phenyl-ethylaminocarbonyl)-2-methyl-phenyl]-propargylamino}benzamidine and trifluoroacetic acid.

Yield: 54% of theory, $R_f$ value: 0.13 (silica gel; methylene chloride/ethanol= 4:1)

$C_{26}H_{26}N_4O \times CF_3COOH$ (410.53/524.55)

Mass spectrum: (M+H)$^+$=411

EXAMPLE 112

4-{3-[4-(N-methyl-N-phenyl-aminocarbonyl)-phenyl]propargylamino}benzamidine

Prepared analogously to Example 4c from 4-{3-[4-(N-methyl-N-phenyl-aminocarbonyl)-phenyl]propargylamino}benzonitrile, ethanol saturated with hydrogen chloride gas and ammonium carbonate.

Yield: 97% of theory, $R_f$ value: 0.20 (silica gel; methylene chloride/ethanol= 4:1+1 drop of acetic acid)

$C_{24}H_{22}N_4O \times HCl$ (382.47/418.93)

Mass spectrum: (M+H)$^+$=383

EXAMPLE 113

4-{3-[2,5-dimethyl-4-(N-methyl-N-phenyl-aminocarbonyl)-phenyl]propargylamino}benzamidine Prepared analogously to Example 2 from N-tert-butoxycarbonyl-4-{3-[2,5-dimethyl-4-(N-methyl-N-phenyl-aminocarbonyl)-phenyl]propargylamino}benzamidine and trifluoroacetic acid.

Yield: 30% of theory, $R_f$ value: 0.18 (silica gel; methylene chloride/ethanol= 4:1)

$C_{26}H_{26}N_4O \times CF_3COOH$ (410.53/524.55)

Mass spectrum: (M+H)$^+$=411

EXAMPLE 114

4-{3-[2,5-dimethyl-4-(N-methyl-N-phenyl-aminocarbonyl)-phenyl]-N-methyl-propargylamino}benzamidine Prepared analogously to Example 4c from 4-{3-[2,5-dimethyl-4-(N-methyl-N-phenyl-aminocarbonyl)-phenyl]-N-methyl-propargylamino}benzonitrile, ethanol saturated with hydrogen chloride gas and ammonium carbonate.

Yield: 54% of theory, $R_f$ value: 0.2 (silica gel; methylene chloride/ethanol=4:1)

$C_{27}H_{28}N_4O \times HCl$ (424.55/461.01)

Mass spectrum: (M+H)$^+$=425

EXAMPLE 115

4-{3-[2-methyl-4-(N-methyl-N-phenyl-aminocarbonyl)-phenyl]-propargylamino}benzamidine Prepared analogously to Example 2 from N-tert-butoxycarbonyl-4-{3-[2-methyl-4-(N-methyl-N-phenyl-aminocarbonyl)-phenyl]propargylamino}benzamidine and trifluoroacetic acid.

Yield: 71% of theory, $R_f$ value: 0.22 (silica gel; methylene chloride/ethanol= 4:1)

$C_{25}H_{24}N_4O \times CF_3COOH$ (396.50/510.52)

Mass spectrum: (M+H)$^+$=397

EXAMPLE 116

4-{3-[2,5-dimethyl-4-(N-methyl-N-pyridin-2-yl-aminocarbonyl)-phenyl]propargylamino}benzamidine Prepared analogously to Example 2 from N-tert-butoxycarbonyl-4-{3-[2,5-dimethyl-4-(N-methyl-N-pyridin-2-yl-aminocarbonyl)-phenyl]propargylamino}benzamidine and trifluoroacetic acid.

Yield: 50% of theory, $R_f$ value: 0.18 (silica gel; methylene chloride/ethanol= 4:1)

$C_{25}H_{25}N_5O \times 2CF_3COOH$ (411.51/639.55)

Mass spectrum: (M+H)$^+$=412

EXAMPLE 117

4-{3-[2-methyl-5-(N-methyl-N-phenyl-aminocarbonyl)-phenyl]-propargylamino}benzamidine Prepared analogously to Example 2 from N-tert-butoxycarbonyl-4-{3-[2-methyl-5-(N-methyl-N-phenylaminocarbonyl)-phenyl]propargylamino}benzamidine and trifluoroacetic acid.

Yield: 75% of theory, $R_f$ value: 0.13 (silica gel; methylene chloride/ethanol= 4:1)

$C_{25}H_{24}N_4O \times CF_3COOH$ (396.50/510.52)

Mass spectrum: $(M+H)^+=397$

EXAMPLE 118

4-{3-[4-(N-methyl-N-phenyl-aminomethyl)-phenyl] propargylamino}benzamidine

Prepared analogously to Example 4c from 4-{3-[4-(N-methyl-N-phenyl-aminomethyl)-phenyl] propargylamino}benzonitrile, ethanol saturated with hydrogen chloride gas and ammonium carbonate.

Yield: 70% of theory, $R_f$ value: 0.22 (silica gel; methylene chloride/ethanol= 4:1+1 drop of acetic acid)

$C_{24}H_{24}N_4 \times HCl$ (368.49/404.95)

Mass spectrum: $(M+H)^+=369$

EXAMPLE 119

4-{3-[4-(N-acetyl-N-phenyl-aminomethyl)-phenyl] propargylamino}benzamidine

Prepared analogously to Example 4c from 4-{3-[4-(N-acetyl-N-phenyl-aminomethyl)-phenyl] propargylamino}benzonitrile, ethanol saturated with hydrogen chloride gas and ammonium carbonate.

Yield: 48% of theory, $R_f$ value: 0.25 (silica gel; methylene chloride/ethanol= 4:1+1 drop of acetic acid)

$C_{25}H_{24}N_4O \times HCl$ (396.50/432.96)

Mass spectrum: $(M+H)^+=397$

EXAMPLE 120

4-{3-[3-(N-methyl-N-phenyl-amino)-phenyl] propargylamino}benzamidine

Prepared analogously to Example 4c from 4-{3-[3-(N-methyl-N-phenyl-amino)-phenyl] propargylamino}benzonitrile, ethanol saturated with hydrogen chloride gas and ammonium carbonate.

Yield: 61% of theory, $R_f$ value: 0.37 (silica gel; methylene chloride/ethanol= 4:1+1 drop of acetic acid)

$C_{23}H_{22}N_4 \times HCl$ (354.46/390.92)

Mass spectrum: $M^+=354$

EXAMPLE 121

4-[3-(4-benzyl-phenyl)propargylamino]benzamidine

Prepared analogously to Example 2 from N-tert-butoxycarbonyl-4-[3-(4-benzyl-phenyl)propargylamino] benzamidine and trifluoroacetic acid.

Yield: 38% of theory, $R_f$ value: 0.26 (silica gel; methylene chloride/ethanol= 4:1+1 drop of acetic acid)

$C_{23}H_{21}N_3 \times CF_3COOH$ (339.44/453.46)

Mass spectrum: $(M+H)^+=340$

EXAMPLE 122

4-[3-(4-phenylsulphonyl-phenyl)propargylamino] benzamidine

Prepared analogously to Example 4c from 4-[3-(4-phenylsulphonyl-phenyl)propargylamino]benzonitrile, ethanol saturated with hydrogen chloride gas and ammonium carbonate.

Yield: 64% of theory, $R_f$ value: 0.14 (silica gel; methylene chloride/ethanol= 4:1)

$C_{22}H_{19}N_3SO_2 \times HCl$ (389.47/425.93)

Mass spectrum: $(M+H)^+=390$

EXAMPLE 123

4-{3-[4-(4-methylphenylsulphonyl)-phenyl] propargylamino}benzamidine

Prepared analogously to Example 4c from 4-{3-[4-(4-methylphenylsulphonyl)phenyl] propargylamino}benzonitrile, ethanol saturated with hydrogen chloride gas and ammonium carbonate.

Yield: 88% of theory, $R_f$ value: 0.13 (silica gel; methylene chloride/ethanol= 4:1)

$C_{23}H_{21}N_3SO_2 \times HCl$ (403.50/439.96)

Mass spectrum: $(M+H)^+=404$

EXAMPLE 124

4-[3-(4-methyl-phenyl)propargylamino]benzamidine and 4-[2-chloro-3-(4-methyl-phenyl)propenylamino] benzamidine as a 4:6 mixture Prepared analogously to Example 4c from 4-[3-(4-methyl-phenyl)pro-pargylamino]benzonitrile, ethanol saturated with hydrogen chloride gas and ammonium carbonate.

Yield: 47% of theory, $R_f$ value: 0.2 (silica gel; methylene chloride/ethanol=4:1)

$C_{17}H_{17}N_3 \times HCl$ (263.34/299.80)

Mass spectrum: $(M+H)^+=264$ $C_{17}H_{18}ClN_3 \times HCl$ (299.80/336.26)

Mass spectrum: $(M+H)^+=300/302$ (chlorine isotopes)

EXAMPLE 125

4-[3-(3-methyl-phenyl)propargylamino]benzamidine

Prepared analogously to Example 4c from 4-[3-(3-methyl-phenyl)pro-pargylamino]benzonitrile, ethanol saturated with hydrogen chloride gas and ammonium carbonate.

Yield: 38% of theory, $R_f$ value: 0.28 (silica gel; methylene chloride/ethanol=4:1 and one drop of acetic acid)

$C_{17}H_{17}N_3 \times HCl$ (263.34/299.80)

Mass spectrum: $M^+=263$

EXAMPLE 126

4-[3-(3-biphenyl)-propargylamino]benzamidine

Prepared analogously to Example 4c from 4-[3-(3-biphenyl)-propargylamino]benzonitrile, ethanol saturated with hydrogen chloride gas and ammonium carbonate.

Yield: 74% of theory, $R_f$ value: 0.29 (silica gel; methylene chloride/ethanol=4:1 and one drop of acetic acid)

$C_{22}H_{19}N_3 \times HCl$ (325.42/361.88)

Mass spectrum: $M^+=326$

EXAMPLE 127

4-[3-(4-ethoxycarbonyl-3-methyl-phenyl)-propargylamino]benzamidine

Prepared analogously to Example 4c from 4-[3-(4-imidazole-1-ylcarbonyl-3-methyl-phenyl)-propargylamino]

benzonitrile, ethanol saturated with hydrogen chloride gas and ammonium carbonate.

Yield: 46% of theory, $R_f$ value: 0.37 (silica gel; ethyl acetate/ethanol/ammonia=50:45:5)

$C_{20}H_{21}N_3O_2 \times HCl$ (335.41/371.87)

Mass spectrum:

$(M+H)^+=336$ $(2M+H)^+=671$

EXAMPLE 128

4-{3-[4-(3-(2-hydroxycarbonyl-ethyl)-5-phenyl-pyrazol-1-yl) -3-methyl-phenyl]-propargylamino}benzamidine Prepared analogously to Example 3 from 4-{3-[4-(3-(2-ethoxycarbonyl-ethyl)-5-phenyl-pyrazol-1-yl)-3-methyl-phenyl]-propargylamino}benzamidine, lithium hydroxide and subsequent treatment with ammonium chloride.

Yield: 58% of theory, $R_f$ value: 0.24 (Reversed phase silica gel RP-8; methanol/5% NaCl solution=6:4)

$C_{29}H_{27}N_5O_2 \times CF_3COOH$ (477.58/591.60)

Mass spectrum:

$(M+H)^+=478$ $(M-H)^-=476$

EXAMPLE 129

4-{3-[4-(3,5-diethyl-pyrazol-1-yl)-3-methyl-phenyl]-propargylamino}benzamidine

Prepared analogously to Example 2 from N-tert-butoxycarbonyl-4-{3-[4-(3,5-diethyl-pyrazol-1-yl)-3-methyl-phenyl]-propargylamino}benzamidine and trifluoroacetic acid.

Yield: 40% of theory, $R_f$ value: 0.3 (silica gel; methylene chloride/ethanol=4:1)

$C_{24}H_{27}N_5 \times CF_3COOH$ (385.52/499.54)

Mass spectrum:

$(M+H)^+=386$ $M^+=385$ $(M-H)^-=384$

EXAMPLE 130

4-{3-[2-methyl-5-(N-methyl-N-pyrid-2-yl-aminocarbonyl)-phenyl] propargylamino}benzamidine Prepared analogously to Example 2 from N-tert-butoxycarbonyl-4-{3-[2-methyl-5-(N-methyl-N-pyrid-2-yl-aminocarbonyl)-phenyl]propargylamino}benzamidine and trifluoroacetic acid.

Yield: 54% of theory, $R_f$ value: 0.17 (silica gel; methylene chloride/ethanol=4:1)

$C_{24}H_{23}N_5O \times CF_3COOH$ (397.49/511.51)

Mass spectrum:

$(M+H)^+=398$ $(M-H)^-=396$ $(M+CF_3COOH-H)^-=510$

EXAMPLE 131

4-{3-[4-[N-(2-hydroxycarbonyl-ethyl)-N-pyridin-2-yl-amino-carbonyl]-2,5-dimethyl-phenyl] propargylamino}benzamidine Prepared analogously to Example 3 from 4-{3-[4-[N-(2-methoxycarbonyl-ethyl)-N-pyridin-2-yl-aminocarbonyl]-2,5-dimethyl-phenyl]propargylamino}benzamidine, lithium hydroxide and subsequent treatment with ammonium chloride.

Yield: 13% of theory, $R_f$ value: 0.5 (Reversed phase silica gel RP-8; methanol/5% NaCl solution=6:4)

$C_{27}H_{27}N_5O_3 \times 2\ HCl$ (469.55/542.47)

Mass spectrum:

$(M+H)^+=470$ $(M-H)^-=468$

EXAMPLE 132

4-{3-[5-ethoxycarbonylmethyl-2-methyl-4-(N-methyl-N-phenyl-aminocarbonyl)-phenyl] propargylamino}benzamidine Prepared analogously to Example 2 from N-tert-butoxycarbonyl-4-{3-[5-ethoxycarbonylmethyl-2-methyl-4-(N-methyl-N-phenyl-aminocarbonyl)-phenyl] propargylamino}benzamidine and trifluoroacetic acid.

Yield: 34% of theory, $R_f$ value: 0.25 (Reversed phase silica gel RP-8; methanol/5% NaCl solution=6:4)

$C_{29}H_{30}N_4O_3 \times CF_3COOH$ (482.59/596.61)

Mass spectrum: $(M+H)^+=483$

EXAMPLE 133

4-[3-(1,3-dihydro-isobenzofuran-1-on-5-yl)-propargylamino]benzamidine

Prepared as a by-product of the treatment of rac-N-tert-butoxycarbonyl-4-{3-[3-hydroxyrethyl-4-(2-methyl-pyrrolidinocarbonyl)-phenyl]propargylamino}benzamidine with trifluoroacetic acid according to Example 88.

Yield: 7% of theory, $R_f$ value: 0.59 (Reversed phase silica gel RP-8; methanol/5% NaCl solution=6:4)

$C_{18}H_{15}N_3O_2 \times CF_3COOH$ (305.34/419.36)

Mass spectrum: $(M+H)^+=306$

EXAMPLE 134

4-[3-(3-methyl-4-pyrrolidinocarbonyl-phenyl)-propargylamino]pyridine a. 4-propargylaminopyridine 10 ml (30 mmol) of a 3 molar ethereal methyl magnesium bromide solution are added dropwise to a solution of 1.9 g (20 mmol) of 4-aminopyridine in 40 ml of tetrahydrofuran and the mixture is stirred for 2 hours. Then 3.7 g (28 mmol) of propargylmethanesulphonate in 40 ml of toluene are added dropwise and the mixture is slowly heated to 110° C., during which time the volatile constituents are distilled off. After 48 hours at 110° C. the mixture is combined with 100 ml of ethyl acetate, washed with 100 ml of a 14% saline solution, filtered and dried with sodium sulphate. After removal of the solvent by distillation, the crude product is purified by chromatography (aluminium oxide; methylene chloride/ethanol 97:3).

Yield: 0.60 g (22% of theory), $R_f$ value: 0.48 (aluminium oxide; methylene chloride/ethanol 19:1)

b. 4-[3-(3-methyl-4-pyrrolidinocarbonyl-phenyl)-propargylamino]pyridine

Prepared analogously to Example 1 g from N-(4-bromo-2-methyl-benzoyl)pyrrolidine, 4-propargylaminopyridine, tetrakis(triphenylphosphine)palladium(0), copper iodide and triethylamine in acetonitrile.

Yield: 31% of theory, $R_f$ value: 0.35 (silica gel; ethyl acetate/ethanol/ammonia 80:40:2)

$C_{20}H_{21}N_3O$ (319.41)

Mass spectrum: $M^+=319$

EXAMPLE 135

Trans-4-[3-(3-methyl-4-pyrrolidinocarbonyl-phenyl)-propargylamino]-cyclohexylamine a. 3-(3-methyl-4-pyrrolidinocarbonyl-phenyl)-propargyl bromide 7.71 g (64 mmol) allyl bromide are added dropwise to a solution of 3.1 g (13 mmol) of 3-(3-methyl-4-pyrrolidinocarbonyl-phenyl)-propargyl alcohol (prepared analogously to Example 9a) and 2.27 g (14 mmol) of 1,1'-carbonyldiimidazole in 90 ml of acetonitrile and stirred first for 30 minutes at ambient temperature, then for 4 hours at 80° C. The mixture is then diluted with 350 ml of ethyl acetate, washed with 100 ml of water and 100 ml of saturated NaCl solution, dried with sodium sulphate, concentrated and purified by flash chromatography (silica gel; methylene chloride to methylene chloride/ethanol 49: 1).

Yield: 1.75 g (45% of theory), $R_f$ value: 0.6 (silica gel; ethyl acetate)

$C_{15}H_{16}BrNO$ (306)

Mass spectrum: $M^+=305/307$ (bromine isotopes)

b. Trans-4-[3-(3-methyl-4-pyrrolidinocarbonyl-phenyl)-propargylamino]-cyclohexylamine 0.53 g (4.09 mmol) of N-ethyl-diisopropylamine is added to a solution of 0.50 g (1.63 mmol) of 3-(3-methyl4-pyrrolidinocarbonyl-phenyl)-propargyl bromide at 0° C. and 0.88 g (4.10 mmol) of trans-4-tert-butoxycarbonyl-aminocyclohexylamine in 50 ml of THF and then stirred for 2 hours at 0° C., 2 hours at 50° C. and 15 hours at ambient temperature. The mixture is then washed twice with 50 ml of saturated sodium hydrogen carbonate solution and with 50 ml of sodium chloride solution. The aqueous phases are then extracted with 50 ml of ethyl acetate and the combined organic phases are dried with sodium sulphate and concentrated in vacuo. The crude product is reacted directly analogously to Example 2 with trifluoroacetic acid in methylene chloride to form the title compound.

Yield: 0.38 g (41% of theory), $R_f$ value: 0.3 (aluminium oxide; ethyl acetate/ethanol/ammonia=50:45:5)

$C_{21}H_{29}N_3O \times 2\ CF_3COOH$ (339.49/567.53)

Mass spectrum: $M^+=339$

EXAMPLE 136

4-{3-[5-(2-phenyl-ethylaminocarbonyl)-2-methyl-phenyl]prop-1-ylamino}benzamidine A suspension of 100 mg (0.19 mmol) of 4-{3-[5-(2-phenyl-ethylaminocarbonyl)-2-methyl-phenyl]propargylamino}benzamidine and 40 mg of 10% palladium on charcoal in 20 ml of ethanol was hydrogenated for 15 minutes at 3 bar of hydrogen pressure. Then the catalyst was filtered off and the filtrate was evaporated down.

Yield: 100% of theory, $R_f$ value: 0.26 (Reversed phase silica gel RP-8; methanol/5% NaCl solution=6:4)

$C_{26}H_{30}N_4O \times CF_3COOH$ (414.56/528.58)

Mass spectrum: $(M+H)^+=415$

EXAMPLE 137

4-[3-(2,5-dimethyl-4-isopropylcarbonyl-phenyl)prop-1-ylamino]benzamidine

Prepared analogously to Example 136 from 4-[3-(2,5-dimethyl-4-isopropylcarbonyl-phenyl)propargylamino]benzamidine, with 10% palladium on charcoal and hydrogen in ethanol.

Yield: 100% of theory, $R_f$ value: 0.13 (Reversed phase silica gel RP-8; methanol/5% NaCl solution=6:4)

$C_{22}H_{29}N_3O \times CF_3COOH$ (351.50/465.52)

Mass spectrum: $(M+H)^+=352$

EXAMPLE 138

4-[3-(2,5-dimethyl-4-pyrrolidinocarbonyl-phenyl)-prop-1-ylamino]benzamidine

Prepared analogously to Example 136 from 4-[3-(2,5-dimethyl-4-pyrrolidinocarbonyl-phenyl)-propargylamino]benzamidine, with 10% palladium on charcoal and hydrogen in ethanol.

Yield: 69% of theory, $R_f$ value: 0.21 (Reversed phase silica gel RP-8; methanol/5% NaCl solution=6:4)

$C_{23}H_{30}N_4O \times CF_3COOH$ (378.53/492.55)

Mass spectrum: $(M+H)^+=379$

EXAMPLE 139 rac-4-{3-[3-methyl-4-(2-methyl-pyrrolidinocarbonyl)-phenyl]-prop-1-ylamino}benzamidine Prepared analogously to Example 136 from rac-4-{3-[3-methyl-4-(2-methyl-pyrrolidinocarbonyl)-phenyl]-propargylamino}-benzamidine, with 10% palladium on charcoal and hydrogen in ethanol.

Yield: 99% of theory, $R_f$ value: 0.2 (silica gel; methylene chloride/ethanol=4:1)

$C_{23}H_{30}N_4O \times CF_3COOH$ (378.52/492.55)

Mass spectrum: $(M+H)^+=379$

EXAMPLE 140

4-{3-[3-(2-hydroxycarbonyl-ethyl)-4-pyrrolidinocarbonyl-phenyl]prop-1-ylamino}benzamidine Prepared analogously to Example 136 from 4-{3-[3-(2-hydroxycarbonyl-ethyl)4-pyrrolidinocarbonyl-phenyl]propargylamino}benzamidine, with 10% palladium on charcoal and hydrogen in ethanol.

Yield: 100% of theory, $R_f$ value: 0.1 (silica gel; methylene chloride/ethanol=4:1)

$C_{24}H_{30}N_4O_3 \times CF_3COOH$ (422.54/536.56)

Mass spectrum: $(M+H)^+=423$

EXAMPLE 141

4-[3-(3-methyl-4-phenylcarbonyl-phenyl)-prop-1-ylamino]-benzamidine

Prepared analogously to Example 136 from 4-[3-(3-methyl-4-phenylcarbonyl-phenyl)-propargylamino]benzamidine, with 10% palladium on charcoal and hydrogen in ethanol.

R_f value: 0.18 (silica gel; methylene chloride/ethanol=4:1)

C_{24}H_{25}N_{3}O×HCl (371.43/407.95)

Mass spectrum:
(M+H)^+=372
(M+HCl−H)^−=406/408 (chlorine isotopes)

EXAMPLE 142

4-{3-[4-(N-(3-dimethylamino-propyl)-N-methyl-aminocarbonyl)-3-methyl-phenyl]prop-1-ylamino}benzamidine Prepared analogously to Example 136 from 4-{3-[4-(N-(3-dimethylamino-propyl)-N-methyl-aminocarbonyl)-3-methyl-phenyl]propargylamino}benzamidine, with 10% palladium on charcoal and hydrogen in ethanol.

Yield: 100% of theory,

R_f value: 0.52 (Reversed phase silica gel RP-8; methanol/5% NaCl solution=60:40)

C_{24}H_{35}N_{5}O×2 CF_{3}COOH (409.59/637.63)

Mass spectrum: (M+H)^+=410

EXAMPLE 143

4-{3-[2,5-dimethyl-4-(N-methyl-N-phenyl-aminocarbonyl)-phenyl]prop-1-ylamino}benzamidine Prepared analogously to Example 136 from 4-{3-[2,5-dimethyl-4-(N-methyl-N-phenyl-aminocarbonyl)-phenyl]propargylamino}benzamidine, with 10% palladium on charcoal and hydrogen in ethanol.

Yield: 100% of theory,

R_f value: 0.34 (Reversed phase silica gel RP-8; methanol/5% NaCl solution=60:40)

C_{26}H_{30}N_{4}O×CF_{3}COOH (414.56/528.58)

Mass spectrum: (M+H)^+=415

EXAMPLE 144

4-{3-[2,5-dimethyl-4-(N-methyl-N-phenyl-aminocarbonyl)-phenyl]-N-methyl-prop-1-ylamino}benzamidine Prepared analogously to Example 136 from 4-{3-[2,5-dimethyl-4-(N-methyl-N-phenyl-aminocarbonyl)-phenyl]-N-methyl-propargylamino}benzamidine, with 10% palladium on charcoal and hydrogen in ethanol.

Yield: 59% of theory,

R_f value: 0.2 (silica gel; methylene chloride/ethanol=4:1)

C_{27}H_{32}N_{4}O×HCl (428.53/465.03)

Mass spectrum: (M+H)^+=429

EXAMPLE 145

4-{3-[5-(N-methyl-N-(2-phenyl-ethyl)-aminocarbonyl)-2-methyl-phenyl]prop-1-ylamino}benzamidine Prepared analogously to Example 136 from 4-{3-[5-(N-methyl-N-(2-phenyl-ethyl)-aminocarbonyl)-2-methyl-phenyl]propargylamino}benzamidine, with 10% palladium on charcoal and hydrogen in ethanol.

Yield: 97% of theory,

R_f value: 0.20 (silica gel; methylene chloride/ethanol=4:1)

C_{27}H_{32}N_{4}O×CF_{3}COOH (428.59/542.61)

Mass spectrum: (M+H)^+=429

EXAMPLE 146

4-{3-[5-(2-phenyl-ethylaminocarbonyl)-2-methyl-phenyl]prop-1-ylamino}benzamidine Prepared analogously to Example 136 from 4-{3-[5-(2-phenyl-ethylaminocarbonyl)-2-methyl-phenyl]propargylamino}-benzamidine, with 10% palladium on charcoal and hydrogen in ethanol.

Yield: 100% of theory,

R_f value: 0.26 (Reversed phase silica gel RP-8; methanol/5% NaCl solution=6:4)

C_{26}H_{30}N_{4}O×CF_{3}COOH (414.56/528.58)

Mass spectrum: (M+H)^+=415

EXAMPLE 147

4-{3-[2-methyl-5-(N-methyl-N-phenyl-aminocarbonyl)-phenyl]prop-1-ylamino}benzamidine Prepared analogously to Example 136 from 4-{3-[2-methyl-5-(N-methyl-N-phenyl-aminocarbonyl)-phenyl]propargylamino}-benzamidine, with 10% palladium on charcoal and hydrogen in ethanol.

Yield: 79% of theory,

R_f value: 0.27 (Reversed phase silica gel RP-8; methanol/5% NaCl solution=6:4)

C_{25}H_{28}N_{4}O×CF_{3}COOH (400.52/514.54)

Mass spectrum: (M+H)^+=401

EXAMPLE 148

4-{3-[2,5-dimethyl-4-(N-methyl-N-pyridin-2-yl-aminocarbonyl)-phenyl]prop-1-ylamino}benzamidine Prepared analogously to Example 136 from 4-{3-[2,5-dimethyl-4-(N-methyl-N-pyridin-2-yl-aminocarbonyl)-phenyl]propargylamino}benzamidine, with 10% palladium on charcoal and hydrogen in ethanol.

Yield: 60% of theory,

R_f value: 0.12 (Reversed phase silica gel RP-8; methanol/5% NaCl solution=6:4)

C_{25}H_{29}N_{5}O×2 CF_{3}COOH (415.53/643.59)

Mass spectrum: (M+H)^+=416

EXAMPLE 149

4-[2-iodo-1-(5-phenylcarbonyl-pyrid-2-yl)prop-1-en-3-yl-amino]benzamidine

Prepared from N-tert-butoxycarbonyl-4-[3-(5-phenylcarbonyl-pyrid-2-yl)-propargylamino]benzamidine by successive treatment with trimethylsilyl iodide analogously to Example 35 and trifluoroacetic acid analogously to Example 2.

Yield: 66% of theory,

R_f value: 0.28 (silica gel; ethyl acetate/ethanol/ammonia=50:45:5)

C_{22}H_{19}IN_{4}O×CF_{3}COOH (482.35/596.37)

Mass spectrum: (M+H)^+=483

EXAMPLE 150

4-[2-chloro-1-(5-phenylcarbonyl-pyrid-2-yl)prop-1-en-3-yl-amino]benzamidine

Prepared analogously to Example 4c from 4-[3-(5-phenylcarbonyl-pyrid-2-yl)-propargylamino]benzonitrile, ethanol saturated with hydrogen chloride gas and ammonium carbonate.

Yield: 76% of theory, $R_f$ value: 0.3 (silica gel; ethyl acetate/ethanol/ammonia=50:45:5)

$C_{22}H_{19}ClN_4O \times HCl$ (390.88/427.34)

Mass spectrum: $(M+H)^+ = 391/393$ (chlorine isotopes)

EXAMPLE 151

E-4-[1-chloro-1-(4-phenyloxy-phenyl)prop-1-en-3-yl-amino]benzamidine and Z-4-[1-chloro-1-(4-phenyloxy-phenyl)prop-1-en-3-yl-amino]benzamidine Prepared analogously to Example 4c from 4-[3-(4-phenyloxy-phenyl)-propargylamino]benzonitrile, ethanol saturated with hydrogen chloride gas and ammonium carbonate.

Yield: 26% of a mixture of E/Z isomers which is separated by preparative HPLC (Lichrospher RP; 250×8 mm; eluant: component A: methanol/acetonitrile=5:1, component B: 1% ammonium formate buffer pH 4.6, component A:B 65:35)

1st isomer ($R_t$=19.05 minutes, cis-HCl addition product): E-4-[1-chloro-1-(4-phenyloxy-phenyl)prop-1-en-3-yl-amino]benzamidine)

2nd isomer ($R_t$=23.53 minutes, trans-HCl addition product): Z-4-[1-chloro-1-(4-phenyloxy-phenyl)prop-1-en-3-yl-amino]benzamidine) $C_{22}H_{20}ClN_3O \times HCl$ (377.87/414.33)

Mass spectrum of the mixture: $(M+H)^+ = 378/380$ (chlorine isotopes)

The following compounds are obtained analogously to the preceding Examples:

(1) 4-{3-[4-(isoxazolidin-2-ylcarbonyl)-2,5-dimethyl-phenyl]propargylamino}benzamidine
(2) 4-{3-[4-[N-(2-ethoxycarbonyl-ethyl)-N-pyrrolidino-aminocarbonyl]-2,5-dimethyl-phenyl]propargylamino}benzamidine
(3) 4-{3-[4-[N-(2-hydroxycarbonyl-ethyl)-N-pyrrolidino-aminocarbonyl]-2,5-dimethyl-phenyl]propargylamino}benzamidine
(4) 4-{3-[2,5-dimethyl-4-(N-methyl-N-phenyl-amino-carbonyl)-phenyl]propargyloxy}benzamidine
(5) 4-[3-(3-methyl-4-pyrrolidinocarbonyl-phenyl)propargylamino]benzamidine
(6) 4-{3-[2,5-dimethyl-4-(N-benzoyl-N-(2-hydroxycarbonyl-ethyl)-amino)-phenyl]propargyloxy}benzamidine
(7) 4-{3-[2,5-dimethyl-4-(N-benzoyl-N-(2-ethoxycarbonyl-ethyl)-amino)-phenyl]propargyloxy}benzamidine
(8) 4-{3-[2,5-dimethyl-4-(N-isopropylcarbonyl-N-(2-hydroxycarbonyl-ethyl)-amino)-phenyl]propargyloxy}benzamidine
(9) 4-{3-[2,5-dimethyl-4-(N-isopropylcarbonyl-N-(2-ethoxycarbonyl-ethyl)-amino)-phenyl]propargyloxy}benzamidine
(10) 4-{3-[2,5-dimethyl-4-(N-phenylsulphonyl-N-(2-hydroxycarbonyl-ethyl)-amino)-phenyl]propargyloxy}benzamidine
(11) 4-{3-[2,5-dimethyl-4-(N-phenylsulphonyl-N-(2-ethoxycarbonyl-ethyl)-amino)-phenyl]propargyloxy}benzamidine

EXAMPLE 152

4-{3-[5-hydroxycarbonylmethyl-2-methyl-4-(N-methyl-N-phenyl-aminocarbonyl)-phenyl]propargylamino}benzamidine Prepared analogously to Example 3 from 4-{3-[5-ethoxycarbonyl-methyl-2-methyl-4-(N-methyl-N-phenyl-aminocarbonyl)-phenyl]propargylamino}benzamidine, lithium hydroxide and subsequent treatment with trifluoroacetic acid.

Yield: 5% of theory, $R_f$ value: 0.42 (Reversed phase silica gel RP-8; methanol/5% NaCl solution=6:4)

$C_{27}H_{26}N_4O_3 \times CF_3COOH$ (454.53/568.45)

Mass spectrum:

$(M+H)^+ = 455$ $(M-H)^- = 453$

EXAMPLE 153

4-{3-[4-[N-(2-ethoxycarbonyl-ethyl)-N-(1-ethylpyrazol-5-yl)-aminocarbonyl]-2,5-dimethyl-phenyl]propargylamino}benzamidine Prepared analogously to Example 2 from N-tert-butoxycarbonyl-4-{3-[4-[N-(2-ethoxycarbonyl-ethyl)-N-(1-ethylpyrazol-5-yl)-aminocarbonyl]-2,5-dimethyl-phenyl]propargylamino}benzamidine and trifluoroacetic acid.

Yield: 24% of theory, $R_f$ value: 0.22 (silica gel; methylene chloride/ethanol=4:1)

$C_{29}H_{34}N_6O_3 \times CF_3COOH$ (514.63/628.65)

Mass spectrum: $(M+H)^+ = 515$

EXAMPLE 154

4-{3-[4-[N-(2-hydroxycarbonyl-ethyl)-N-(1-ethylpyrazol-5-yl)-aminocarbonyl]-2,5-dimethyl-phenyl]propargylamino}benzamidine Prepared analogously to Example 3 from 4-{3-[4-[N-(2-ethoxycarbonyl-ethyl)-N-(1-ethylpyrazol-5-yl)-aminocarbonyl]-2,5-dimethyl-phenyl]propargylamino}benzamidine, lithium hydroxide and subsequent treatment with trifluoroacetic acid.

Yield: 6% of theory, $C_{27}H_{30}N_6O_3 \times CF_3COOH$ (486.58/600.60)

Mass spectrum: $(M+H)^+ = 487$

EXAMPLE 155

4-{3-[4-(isoxazolidin-2-ylcarbonyl)-3-methyl-phenyl]-propargylamino}benzamidine

Prepared analogously to Example 2 from N-tert-butoxycarbonyl-4-{3-[4-(isoxazolidin-2-ylcarbonyl)-3-methyl-phenyl]propargylamino}benzamidine and trifluoroacetic acid.

Yield: 42% of theory, $R_f$ value: 0.09 (silica gel; methylene chloride/ethanol=4:1)

$C_{21}H_{22}N_4O_2 \times CF_3COOH$ (362.44/476.46)

Mass spectrum: $(M+H)^+ = 363$

EXAMPLE 156

4-{3-[4-(diethylaminocarbonyl)-2,5-dimethyl-phenyl]-propargylamino}benzamidine

Prepared analogously to Example 2 from N-tert-butoxycarbonyl-4-{3-[4-(diethylaminocarbonyl)-2,5-dimethyl-phenyl]propargylamino}benzamidine and trifluoroacetic acid.

Yield: 36% of theory, $R_f$ value: 0.1 (silica gel; methylene chloride/ethanol=4:1)

$C_{23}H_{28}N_4O \times CF_3COOH$ (376.51/490.53)

Mass spectrum: $(M+H)^+=377$

EXAMPLE 157

4-{3-[2,5-dimethyl-4-(N-(2-methoxycarbonyl-ethyl)-N-ethylcarbonyl-amino)-phenyl]-propargylamino}benzamidine a. 2,5-dimethyl-4-(2-methoxycarbonyl-ethyl-amino)-1-iodo-benzene 15.0 g (0.061 mol) of 2,5-dimethyl-4-iodo-aniline, 55 ml of (0.611 mol) of methyl acrylate, 6 ml of benzyltrimethyl ammonium hydroxide and 0.3 g (3 mmol) of hydroquinone are refluxed for 11 days. Then the excess acrylate is distilled off and the residue is chromatographed on silica gel, eluting with methylene chloride.

Yield: 11.7 g (58% of theory), $R_f$ value: 0.65 (silica gel; ethyl acetate/petroleum ether=4:6)

b. 2,.5-dimethyl-4-(N-(2-methoxycarbonyl-ethyl)-N-ethyl-carbonyl-amino)-1-iodo-benzene 0.5 ml of (6 mmol) of propionic acid chloride is placed in 30 ml of tetrahydrofuran, 2.0 g (6 mmol) of 2,5-dimethyl-4-(2-methoxycarbonyl-ethyl-amino)-1-iodo-benzene in 30 ml of tetrahydrofuran are added dropwise while cooling with ice and the mixture is stirred for another 30 minutes while cooling with ice. It is stirred overnight at ambient temperature, then diluted with 14% NaCl solution and extracted with ethyl acetate. The combined organic extracts are dried over sodium sulphate and evaporated down. The residue is chromatographed on silica gel, eluting with petroleum ether/ethyl acetate (3:1).

Yield: 2.08 g (89% of theory), $R_f$ value: 0.38 (silica gel; dichloromethane/ethanol=98:2)

c. N-tert.butoxycarbonyl-4-{3-[2,5-dimethyl-4-(N-(2-methoxycarbonyl-ethyl)-N-ethylcarbonyl-amino)-phenyl]-propargylamino}benzamidine Prepared analogously to Example 1g from 2,5-dimethyl-4-(N-(2-methoxycarbonyl-ethyl)-N-ethylcarbonyl-amino)-iodo-benzene, N-tert-butoxycarbonyl-4-propargylamino-benzamidine, tetrakis(triphenyl-phosphine)palladium(0), copper(I)iodide and triethylamine in acetonitrile.

Yield: 0.4 g (20% of theory), $C_{30}H_{38}N_4O_5$ (534.66)

Mass spectrum:

$(M+H)^+=535$ $(M+Na)^+=557$ d. 4-{3-[2,5-dimethyl-4-(N-(2-methoxycarbonyl-ethyl)-N-ethylcarbonyl-amino)-phenyl]-propargylamino}benzamidine Prepared analogously to Example 2 from N-tert-butoxycarbonyl-4-{3-[2,5-dimethyl-4-(N-(2-methoxycarbonyl-ethyl)-N-ethylcarbonyl-amino)-phenyl]-propargylamino}benzamidine and trifluoroacetic acid.

Yield: 77% of theory, $C_{25}H_{30}N_4O_3 \times _{CF_3}COOH$ (434.57/548.57)

Mass spectrum:

$(M+H)^+=435$ $(M-H)^-=433$

EXAMPLE 158

4-{3-[2,5-dimethyl-4-(N-(3-ethoxycarbonyl-propionyl)-N-isopropyl-amino)-phenyl]-propargylamino}benzamidine a. 2,5-dimethyl-4-iodo-aniline 25.0 g (71.8 mmol) of benzyltrimethylammonium dichloriodate and 12.8 g (92.5 mmol) of potassium carbonate are added to a solution of 8.8 ml of (70.8 mmol) of 2,5-dimethylaniline in 250 ml of methanol and 600 ml of dichloromethane and stirred for 1 hour at ambient temperature. Then the inorganic salts are suction filtered and the solvent is distilled off. The residue is combined with a solution of 13.5 g (70.8 mmol) of sodium pyrosulphite in 640 ml of water and extracted with ether. The combined organic extracts are dried over sodium sulphate and evaporated down. The crude product is triturated with petroleum ether, suction filtered and dried.

Yield: 13.3 g (76% of theory), $R_f$ value: 0.65 (silica gel; ethyl acetate/petroleum ether=3:7)

b. 2,5-dimethyl-4-iodo-N-isopropyl-aniline 4.1 g (0.017 mol) of 2,5-dimethyl-4-iodo-aniline, 1.4 ml of (0.019 mol) of acetone, 1.4 ml of (0,024 mol) of glacial acetic acid and 0.1 g (0.001 mol) of p-toluenesulphonic acid are dissolved in 30 ml of tetrahydrofuran and stirred for 30 minutes at ambient temperature. Then 4.7 g (0.022 mol) of sodium triacetoxyborohydride are added and the mixture is stirred for another 20 hours at ambient temperature. After the addition of 150 ml of water, sodium carbonate is added until no further development of $CO_2$ can be detected. The mixture is then extracted with ethyl acetate, the combined organic extracts are dried over sodium sulphate and evaporated down. The residue is chromatographed on silica gel, eluting with ethyl acetate/petroleum ether (2:98).

Yield: 4.4 g (91.3% of theory), $R_f$ value: 0.50 (silica gel; ethyl acetate/petroleum ether=3:7)

c. 2,5-dimethyl-N-(3-ethoxycarbonyl-propionyl)-N-isopropyl-4-iodo-aniline 2.0 g (6.9 mmol) of 2,5-dimethyl-4-iodo-N-isopropyl-aniline and 2.4 ml of (13.8 mmol) of N-ethyl-diisopropylamine are dissolved in 30 ml of tetrahydrofuran and, after the addition of 1.5 ml (10.5 mmol) of ethyl succinate chloride, refluxed for 2 hours. After cooling to ambient temperature the mixture is diluted with ethyl acetate and washed successively with 1 molar hydrochloric acid and 1 molar sodium hydroxide solution. The organic phase is dried over sodium sulphate and evaporated down.

Yield: 2.9 g (100% of theory), $R_f$ value: 0.85 (silica gel; ethyl acetate/petroleum ether=3:7)

d. N-tert-butoxycarbonyl-4-{3-[2,5-dimethyl-4-(N-(3ethoxycarbonyl-propionyl)-N-isopropyl-amino)-phenyl]-propargylamino}benzamidine Prepared analogously to Example 1g from 2,5-dimethyl-N-(3-ethoxycarbonyl-propionyl)-N-isopropyl-4-iodoaniline, N-tert-butoxycarbonyl-4-propargylamino-benzamidine, tetrakis(triphenyl-phosphine)palladium(0), copper(I)iodide and triethylamine in acetonitrile.

Yield: 39% of theory, $R_f$ value: 0.3 (silica gel; dichloromethane/ethanol=19:1)

$C_{32}H_{42}N_4O_5$ (562.72)

Mass spectrum:

$(M+H)^+=563$ $(M+Na)^+=585$ e. 4-{3-[2,5-dimethyl-4-(N-(3-ethoxycarbonyl-propionyl)-N-isopropyl-amino)-phenyl]-propargylamino}benzamidine Prepared analogously to Example 2 from N-tert-butoxycarbonyl-4-{3-[2,5-dimethyl-4-(N-(3-ethoxycarbonyl-propionyl)-N-isopropyl-amino)-phenyl]-propargylamino}benzamidine and trifluoroacetic acid.

Yield: 47% of theory, $C_{27}H_{34}N_4O_3 \times CF_3COOH$ (462.62/576.62)

Mass spectrum:

$(M+H)^+=463$ $(M-H)^-=461$

EXAMPLE 159

4-{3-[5-(N-(2-ethoxycarbonylethyl)-N-(2-pyridyl)-aminocarbonyl)-2-ethyl-phenyl]propargylamino}benzamidine Prepared analogously to Example 2 from N-tert-butoxycarbonyl-4-{3-[5-(N-(2-ethoxycarbonylethyl)-N-(2-pyridyl)-aminocarbonyl)-2-ethyl-phenyl]propargylamino}benzamidine and trifluoroacetic acid.

Yield: 47% of theory, $R_f$ value: 0.19 (silica gel; dichloromethane/ethanol=4:1)

$C_{29}H_{31}N_5O_3 \times CF_3COOH$ (497.60/611.62)

Mass spectrum: $(M+H)^+=498$

EXAMPLE 160

4-{3-[5-(N-(2-hydroxycarbonylethyl)-N-(2-pyridyl)-aminocarbonyl)-2-ethyl-phenyl]propargylamino}benzamidine Prepared analogously to Example 3 from 4-{3-[5-(N-(2-ethoxycarbonylethyl)-N-(2-pyridyl)-aminocarbonyl]-2-ethyl-phenyl]propargylamino}benzamidine, sodium hydroxide and subsequent treatment with trifluoroacetic acid.

Yield: 55% of theory, $R_f$ value: 0.31 (silica gel; dichloromethane/ethanol=4:1)

$C_{27}H_{27}N_5O_3 \times CF_3COOH$ (469.54/583.57)

Mass spectrum:

$(M+H)^+=470$ $(M-H)^-=468$

EXAMPLE 161

4-{3-[2,5-dimethyl-4-(N-(2-methoxycarbonyl-ethyl)-N-benzoyl-amino)-phenyl]-propargylamino}benzamidine Prepared analogously to Example 2 from N-tert-butoxycarbonyl-4-{3-[2,5-dimethyl-4-(N-(2-methoxycarbonyl-ethyl)-N-benzoyl-amino)-phenyl]-propargylamino}benzamidine and trifluoroacetic acid.

Yield: 29% of theory, $C_{29}H_{30}N_4O_3 \times CF_3COOH$ (482.59/596.61)

Mass spectrum: $(M+H)^+=483$

EXAMPLE 162

4-{3-[2,5-dimethyl-4-(N-(2-pyridyl)-N-methyl-aminocarbonyl)-phenyl]-N-methyl-propargylamino}benzamidine Prepared analogously to Example 1e from 4-{3-[2,5-dimethyl-4-(N-(2-pyridyl)-N-methyl-aminocarbonyl)-phenyl]-N-methyl-propargylamino}benzonitrile and hydrochloric acid/ammonium carbonate in ethanol.

Yield: 6% of theory, $C_{26}H_{27}N_5O \times HCl$ (425.54/462.00)

Mass spectrum: $(M+H)^+=426$

EXAMPLE 163

4-{3-[4-(3,5-diethyl-pyrazol-1-yl)-2,5-dimethyl-phenyl]-propargylamino}benzamidine Prepared analogously to Example 2 from N-tert-butoxycarbonyl-4-{3-[4-(3,5-diethyl-pyrazol-1-yl)-2,5-dimethyl-phenyl]-propargylamino}benzamidine and trifluoroacetic acid.

Yield: 96% of theory, $C_{25}H_{29}N_5 \times CF_3COOH$ (399.55/513.57)

Mass spectrum: $(M+H)^+=400$

EXAMPLE 164

4-{3-[2,5-dimethyl-4-(N-ethylcarbonyl-N-(2-hydroxycarbonyl-ethyl)-amino)-phenyl]propargylamino}benzamidine Prepared analogously to Example 3 from 4-{3-[2,5-dimethyl-4-(N-ethylcarbonyl-N-(2-methoxycarbonyl-ethyl)-amino)-phenyl]-propargylamino}benzamidine and sodium hydroxide.

Yield: 59% of theory, $C_{24}H_{28}N_4O_3$ (420.52)

Mass spectrum:

$(M+H)^+=421$ $(M+Na)^+=443$

EXAMPLE 165

4-{3-[2,5-dimethyl-4-(N-phenylsulphonyl-N-(2-methoxycarbonyl-ethyl)-amino)-phenyl]-propargylamino}-benzamidine Prepared analogously to Example 2 from N-tert-butoxycarbonyl-4-{3-[2,5-dimethyl-4-(N-phenylsulphonyl-N-(2-methoxycarbonyl-ethyl)-amino)-phenyl]-propargylamino}-benzamidine and trifluoroacetic acid.

Yield: 63% of theory, $C_{28}H_{30}N_4O_4S \times CF_3COOH$ (518.64/632.66)

Mass spectrum: $(M+H)^+=519$

EXAMPLE 166

4-{3-[2,5-dimethyl-4-(N-phenylsulphonyl-N-(2-hydroxycarbonyl-ethyl)-amino)-phenyl]-propargylamino}-benzamidine Prepared analogously to Example 3 from 4-{3-[2,5-dimethyl-4-(N-phenylsulphonyl-N-(2-methoxycarbonylethyl)-amino)-phenyl]-propargylamino}-benzamidine, lithium hydroxide and subsequent treatment with glacial acetic acid.

Yield: 37% of theory, $C_{27}H_{28}N_4O_4S$ (504.61)

Mass spectrum:

$(M+H)^+=505$ $(M+Na)^-=527$

EXAMPLE 167

4-{3-[2,5-dimethyl-4-(N-phenylsulphonyl-N-(2-methoxycarbonyl-ethyl)-amino)-phenyl]-prop-1-ylamino}-benzamidine Prepared analogously to Example 136 from 4-{3-[2,5-dimethyl-4-(N-phenylsulphonyl-N-(2-methoxycarbonyl-ethyl)-amino)-phenyl]-propargylamino}-benzamidine, 10% palladium on activated charcoal and hydrogen in ethanol.

Yield: 65% of theory, $C_{28}H_{34}N_4O_4S \times CF_3COOH$ (522.68/636.70)

Mass spectrum: $(M+H)^+=523$

EXAMPLE 168

4-{3-[2,5-dimethyl-4-(N-(2-methoxycarbonyl-ethyl)-N-propylcarbonyl-amino)-phenyl]-propargylamino}-benzamidine Prepared analogously to Example 2 from N-tert-butoxycarbonyl-4-{3-[2,5-dimethyl-4-(N-(2-methoxycarbonyl-ethyl)-N-propylcarbonyl-amino)-phenyl]-propargylamino}-benzamidine and trifluoroacetic acid.

Yield: 82% of theory, $C_{26}H_{32}N_4O_3 \times CF_3COOH$ (448.57/562.59)

Mass spectrum: $(M+H)^+=449$

EXAMPLE 169

4-{3-[2,5-dimethyl-4-(N-(2-methoxycarbonyl-ethyl)-N-cyclopropylcarbonyl-amino)-phenyl]-propargylamino}-benzamidine Prepared analogously to Example 2 from N-tert-butoxycarbonyl-4-{3-[2,5-dimethyl-4-(N-(2-methoxycarbonyl-ethyl)-N-cyclopropylcarbonyl-amino)-phenyl]-propargylamino}-benzamidine and trifluoroacetic acid.

Yield: 37% of theory, $C_{26}H_{30}N_4O_3 \times CF_3COOH$ (446.56/560.58)

Mass spectrum:

$(M+H)^+=447$ $(M-H)^-=445$

EXAMPLE 170

4-{3-[2,5-dimethyl-4-(N-(2-methoxycarbonyl-ethyl)-N-methylcarbonyl-amino)-phenyl]-propargylamino}-benzamidine Prepared analogously to Example 2 from N-tert-butoxycarbonyl-4-{3-[2,5-dimethyl-4-(N-(2-methoxycarbonyl-ethyl)-N-methylcarbonyl-amino)-phenyl]-propargylamino}-benzamidine and trifluoroacetic acid.

Yield: 90% of theory, $C_{24}H_{28}N_4O_3 \times CF_3COOH$ (420.52/534.54)

Mass spectrum: $(M+H)^+=421$

EXAMPLE 171

4-{3-[2,5-dimethyl-4-(N-(2-hydroxycarbonyl-ethyl)-N-methylcarbonyl-amino)-phenyl]-propargylamino}-benzamidine Prepared analogously to Example 3 from 4-{3-[2,5-dimethyl-4-(N-(2-methoxycarbonyl-ethyl)-N-methylcarbonyl-amino)-phenyl]-propargylamino}-benzamidine, lithium hydroxide and subsequent treatment with glacial acetic acid.

Yield: 57% of theory, $C_{23}H_{26}N_4O_3$ (406.49)

Mass spectrum: $(M-H)^-=405$

EXAMPLE 172

4-{3-[2,5-dimethyl-4-(N-(2-hydroxycarbonyl-ethyl)-N-propylcarbonyl-amino)-phenyl]-propargylamino}-benzamidine Prepared analogously to Example 3 from 4-{3-[2,5-dimethyl-4-(N-(2-methoxycarbonyl-ethyl)-N-propylcarbonyl-amino)-phenyl]-propargylamino}-benzamidine, lithium hydroxide and subsequent treatment with glacial acetic acid.

Yield: 65% of theory, $C_{25}H_{30}N_4O_3$ (434.54)

Mass spectrum:

$(M-H)^-=433$ $(M+H)^+=435$

EXAMPLE 173

4-{3-[2,5-dimethyl-4-(N-2-hydroxycarbonyl-ethyl-N-cyclopropylcarbonyl-amino)-phenyl]-propargylamino}-benzamidine Prepared analogously to Example 3 from 4-{3-[2,5-dimethyl-4-(N-(2-methoxycarbonyl-ethyl)-N-cyclopropylcarbonyl-amino)-phenyl]-propargylamino}-benzamidine, lithium hydroxide and subsequent treatment with glacial acetic acid.

Yield: 75% of theory, $C_{25}H_{28}N_4O_3$ (432.53)

Mass spectrum:

$(M+Na)^+=455$ $(M+H)^+=433$

EXAMPLE 174

4-{3-[2,5-dimethyl-4-(N-(3-hydroxycarbonyl-propionyl)-N-isopropyl-amino)-phenyl]-propargylamino}-benzamidine Prepared analogously to Example 3 from 4-{3-[2,5-dimethyl-4-(N-(3-ethoxycarbonyl-propionyl)-N-isopropyl-amino)-phenyl]-propargylamino}-benzamidine, lithium hydroxide and subsequent treatment with glacial acetic acid.

Yield: 73% of theory, $C_{25}H_{30}N_4O_3$ (434.54)

Mass spectrum:
(M+H)$^+$=435
(M−H)$^-$=433

EXAMPLE 175

4-{3-[2,5-dimethyl-4-(N-ethylcarbonyl-N-(2-methoxycarbonyl-ethyl)-amino)-phenyl]-prop-1-ylamino}-benzamidine Prepared analogously to Example 136 from 4-{3-[2,5-dimethyl-4-(N-ethylcarbonyl-N-(2-methoxycarbonyl-ethyl)-amino)-phenyl]-propargylamino}benzamidine, 10% palladium on activated charcoal and hydrogen in ethanol.

Yield: 99% of theory, $C_{25}H_{34}N_4O_3 \times CF_3COOH$ (438.58/552.60)

Mass spectrum: (M+H)$^+$=439

EXAMPLE 176

4-{3-[2,5-dimethyl-4-(N-(3-hydroxycarbonyl-propionyl)-N-isopropyl-amino)-phenyl]-prop-1-ylamino}-benzamidine Prepared analogously to Example 136 from 4-{3-[2,5-dimethyl-4-(N-(3-hydroxycarbonyl-propionyl)-N-isopropyl-amino)-phenyl]-propargylamino}-benzamidine, 10% palladium on activated charcoal and hydrogen in ethanol.

Yield: 99% of theory, $C_{25}H_{34}N_4O_3$ (438.58/552.60)

Mass spectrum:
(M+H)$^+$=439
(M−H)$^-$=437

EXAMPLE 177

4-{3-[2,5-dimethyl-4-(N-(3-ethoxycarbonyl-propionyl)-N-benzyl-amino)-phenyl]-propargylamino}-benzamidine Prepared analogously to Example 2 from N-tert-butoxycarbonyl-4-{3-[2,5-dimethyl-4-(N-(3-ethoxycarbonyl-propionyl)-N-benzyl-amino)-phenyl]-propargylamino}-benzamidine and trifluoroacetic acid.

Yield: 64% of theory, $C_{31}H_{34}N_4O_3 \times CF_3COOH$ (510.65/624.67)

Mass spectrum: (M+H)$^+$=511

EXAMPLE 178

4-{3-[2,5-dimethyl-4-(N-(3-hydroxycarbonyl-propionyl)-N-benzyl-amino)-phenyl]-propargylamino}-benzamidine Prepared analogously to Example 3 from 4-{3-[2,5-dimethyl-4-(N-(3-ethoxycarbonyl-propionyl)-N-benzyl-amino)-phenyl]-propargylamino}-benzamidine, lithium hydroxide and subsequent treatment with trifluoroacetic acid.

Yield: 73% of theory, $C_{29}H_{30}N_4O_3 \times CF_3COOH$ (482.59/596.61)

Mass spectrum:
(M+H)$^+$=483
(M−H)$^-$=481

EXAMPLE 179

4-{3-[2,5-dimethyl-4-(N-ethylcarbonyl-N-methoxycarbonylmethyl-amino)-phenyl]-propargylamino}-benzamidine Prepared analogously to Example 2 from N-tert-butoxycarbonyl-4-{3-[2,5-dimethyl-4-(N-ethylcarbonyl-N-methoxycarbonylmethyl-amino)-phenyl]-propargylamino}-benzamidine and trifluoroacetic acid.

Yield: 67% of theory, $C_{24}H_{28}N_4O_3 \times CF_3COOH$ (420.52/534.54)

Mass spectrum: (M+CF$_3$COOH—H)$^-$=533

EXAMPLE 180

4-{3-[4-(4,4-dimethyl-5-oxo-4,5-dihydro-1H-pyrazol-3-yl)-2,5-dimethyl-phenyl]-propargylamino}-benzamidine a. 4-bromo-2.5-dimethylbenzoic acid chloride 10.3 g (45 mmol) of 4-bromo-2,5-dimethylbenzoic acid are dissolved in 250 ml of dichloromethane and after the addition of 9.9 ml of (135 mmol) of thionyl chloride refluxed for two hours. Then the mixture is evaporated to dryness.

Yield: 3.2 g (100% of theory).

b. 3-(4-bromo-2,5-dimethyl-phenyl)-2,2-dimethyl-3-oxo-methyl propionate 5.4g (0.022 mol) of 4-bromo-2,5-dimethylbenzoic acid chloride, 4.5 ml of (0.022 mol) of 1-methoxy-2-methyl-1-(trimethylsilyloxy)-1-propene and 8.2 ml (0.066 mol) of boron trifluoride etherate are refluxed in 50 ml of diethyl ether under a nitrogen atmosphere for 20 hours. Then the mixture is washed 2× with 50 ml of 1N sodium hydroxide solution and 1× with 50 ml of water. The organic phase is dried with sodium sulphate and the solvent is distilled off.

Yield: 3.6 g (53% of theory),

R$_f$ value: 0.6 (silica gel; petroleum ether/ethyl acetate= 4:1)

c. 3-(4-bromo-2,5-dimethyl-phenyl)-4,4-dimethyl-4,5-dihydro-1H-pyrazol-5-one 3.5 g (11.7 mmol) of methyl 3-(4-bromo-2,5-dimethyl-phenyl)-2,2-dimethyl-3-oxo-propionate and 28 ml (28 mmol) of 1 molar hydrazine solution in tetrahydrofuran are refluxed in 50 ml of ethanol for 24 hours. The solvent is distilled off and the residue is recrystallised from ethanol.

Yield: 2.1 g (64% of theory),

R$_f$ value: 0.9 (silica gel; petroleum ether/ethyl acetate= 7:3)

d. N-tert-butoxycarbonyl-4-{3-[4-(4,4-dimethyl-5-oxo-4,5-dihydro-1H-pyrazol-3-yl)-2,5dimethyl-phenyl]-propargylamino}-benzamidine Prepared analogously to Example 1g from 3-(4-bromo-2,5-dimethyl-phenyl)-4,4-dimethyl-4,5-dihydro-1H-pyrazol-5-one, N-tert-butoxycarbonyl-4-propargylamino-benzamidine, tetrakis-(triphenylphosphine)-palladium(0), copper-I-iodide and triethylamine in acetonitrile.

Yield: 19% of theory,

R$_f$ value: 0.2 (silica gel; dichloromethane/ethanol=19:1)

e. 4-{3-[4-(4,4-dimethyl-5-oxo-4,5-dihydro-1H-pyrazol-3-yl)-2,5-dimethyl-phenyl]-propargylamino}-benzamidine Prepared analogously to Example 2 from N-tert-butoxy-4-{3-[4-(4,4-dimethyl-5-oxo-4,5-dihydro-1H-pyrazol-3-yl)-

2,5-dimethyl-phenyl]-propargylamino}-benzamidine and trifluoroacetic acid.

Yield: 93% of theory, $C_{23}H_{25}N_5O \times CF_3COOH$ (387.49/501.51)

Mass spectrum: $(M+H)^+ = 388$

EXAMPLE 181

4-{3-[2,5-dimethyl-4-(N-ethylcarbonyl-N-hydroxycarbonylmethyl-amino)-phenyl]-propargylamino}-benzamidine Prepared analogously to Example 3 from 4-{3-[2,5-dimethyl-4-(N-ethylcarbonyl-N-methoxycarbonylmethyl-amino)-phenyl]-propargylamino}-benzamidine, lithium hydroxide and subsequent treatment with glacial acetic acid.

Yield: 74% of theory, $C_{23}H_{26}N_4O_3$ (406.49)

Mass spectrum:

$(M+H)^+ = 407$ $(M+Na)^+ = 429$ $(M-H)^- = 405$

EXAMPLE 182

4-{3-[2,5-dimethyl-4-(N-ethylcarbonyl-N-ethoxycarbonylmethylaminocarbonylmethyl-amino)-phenyl]-propargylamino}-benzamidine Prepared analogously to Example 2 from N-tert-butoxycarbonyl-4-{3-[2,5-dimethyl-4-(N-ethylcarbonyl-N-ethoxycarbonylmethylaminocarbonylmethyl-amino)-phenyl]-propargylamino}-benzamidine and trifluoroacetic acid.

Yield: 61% of theory, $C_{27}H_{33}N_5O_4 \times CF_3COOH$ (491.60/605.62)

Mass spectrum: $(M+H)^+ = 492$

EXAMPLE 183

4-{3-[2,5-dimethyl-4-(N-ethylcarbonyl-N-hydroxycarbonylmethylaminocarbonylmethyl-amino)-phenyl]-propargylamino}-benzamidine Prepared analogously to Example 3 from 4-{3-[2,5-dimethyl-4-(N-ethylcarbonyl-N-ethoxycarbonylmethylaminocarbonylmethyl-amino)-phenyl]-propargylamino}-benzamidine, lithium hydroxide and subsequent treatment with glacial acetic acid.

Yield: 48% of theory, $C_{25}H_{29}N_5O_4$ (463.54)

Mass spectrum:

$(M+H)^+ = 464$ $(M-H)^- = 462$

EXAMPLE 184

4-{3-[2,5-dimethyl-4-(N-isopropyl-N-ethoxycarbonylmethylaminocarbonyl-amino)-phenyl]-propargylamino}-benzamidine Prepared analogously to Example 2 from N-tert-butoxycarbonyl-4-{3-[2,5-dimethyl-4-(N-isopropyl-N-ethoxycarbonylmethylaminocarbonyl-amino)-phenyl]-propargylamino}-benzamidine and trifluoroacetic acid.

Yield: 67% of theory, $C_{26}H_{33}N_5O_3 \times CF_3COOH$ (463.59/577.61)

Mass spectrum: $(M+H)^+ = 464$

EXAMPLE 185

4-{3-[2,5-dimethyl-4-(N-isopropyl-N-hydroxycarbonylmethylaminocarbonyl-amino)-phenyl]-propargylamino}-benzamidine Prepared analogously to Example 3 from 4-{3-[2,5-dimethyl-4-(N-isopropyl-N-methoxycarbonylmethylaminocarbonyl-amino)-phenyl]-propargylamino}-benzamidine, lithium hydroxide and subsequent treatment with glacial acetic acid.

Yield: 68% of theory, $C_{24}H_{29}N_5O_3$ (435.53)

Mass spectrum:

$(M+H)^+ = 436$ $(M-H)^- = 434$

EXAMPLE 186

4-{3-[2,5-dimethyl-4-(N-isopropyl-N-(3-trifluoracetylamino-3-methoxycarbonyl-propionyl)-amino)-phenyl]-propargylamino}-benzamidine Prepared analogously to Example 2 from N-tert-butoxycarbonyl-4-{3-[2,5-dimethyl-4-(N-isopropyl-N-(3-trifluoracetylamino-3-methoxycarbonyl-propionyl)-amino)-phenyl]-propargylamino}-benzamidine and trifluoroacetic acid.

Yield: 65% of theory, $C_{28}H_{32}F_3N_5O_4 \times CF_3COOH$ (559.59/673.61)

Mass spectrum:

$(M+H)^+ = 560$ $(M-H)^- = 558$

EXAMPLE 187

4-{3-[2,5-dimethyl-4-(N-isopropyl-N-methoxycarbonylmethoxymethylcarbonyl-amino)-phenyl]-propargylamino}-benzamidine Prepared analogously to Example 2 from N-tert-butoxycarbonyl-4-{3-[2,5-dimethyl-4-(N-isopropyl-N-methoxycarbonylmethoxymethylcarbonyl-amino)-phenyl]-propargylamino}-benzamidine and trifluoroacetic acid.

Yield: 65% of theory, $C_{26}H_{32}N_4O_4 \times CF_3COOH$ (464.47/578.59)

Mass spectrum: $M^+ = 464$

EXAMPLE 188

4-{3-[2,5-dimethyl-4-(N-isopropyl-N-hydroxycarbonylmethoxymethylcarbonyl-amino)-phenyl]-propargylamino}-benzamidine Prepared analogously to Example 3 from 4-{3-[2,5-dimethyl-4-(N-isopropyl-N-methoxycarbonylmethoxymethylcarbonyl-amino)-phenyl]-propargylamino}-benzamidine, lithium hydroxide and subsequent treatment with glacial acetic acid.

Yield: 12% of theory, $C_{25}H_{30}N_4O_4$ (450.54)

Mass spectrum:
(M+H)$^+$=451
(M–H)$^-$=449

EXAMPLE 189

4-{3-[2,5-dimethyl-4-(N-isopropyl-N-methoxycarbonylmethylcarbonyl-amino)-phenyl]-propargylamino}-benzamidine Prepared analogously to Example 2 from N-tert-butoxycarbonyl-4-{3-[2,5-dimethyl-4-(N-isopropyl-N-methoxycarbonylmethylcarbonyl-amino)-phenyl]-propargylamino}-benzamidine and trifluoroacetic acid.

Yield: 74% of theory,
$C_{25}H_{30}N_4O_3 \times CF_3COOH$ (434.54/548.56)
Mass spectrum:
(M+H)$^+$=435
(M–H)$^-$=433

EXAMPLE 190

4-{3-[2,5-dimethyl-4-(N-isopropyl-N-hydroxycarbonylmethyl-carbonyl-amino)-phenyl]-propargylamino}-benzamidine Prepared analogously to Example 3 from 4-{3-[2,5-dimethyl-4-(N-isopropyl-N-methoxycarbonylmethylcarbonyl-amino)-phenyl]-propargylamino}-benzamidine, lithium hydroxide and subsequent treatment with glacial acetic acid.

Yield: 80% of theory,
$C_{24}H_{28}N_4O_3$ (420.51)
Mass spectrum:
(M+H)$^+$=421
(M–H)$^-$=419
(M+Na)$^+$=443

EXAMPLE 191

4-{3-[2,5-dimethyl-4-(N-isopropyl-N-methoxycarbonylmethyl-aminocarbonylmethylcarbonyl-amino)-phenyl]-propargylamino}-benzamidine 0.3 g (0.71 mol) of 4-{3-[2,5-dimethyl-4-(N-isopropyl-N-hydroxycarbonylmethylcarbonyl-amino)-phenyl]-propargylamino}-benzamidine and 0.1 g (0.71 mol) of glycine methyl ester are dissolved in 10 ml of dimethylformamide and after the addition of 0.2 g (0.78 mol) of N,N'-dicyclohexylcarbodiimide are stirred for 20 hours at ambient temperature. Then the precipitate formed is suction filtered and the mother liquor is evaporated to dryness. The residue is chromatographed on silica gel, eluting with dichloromethane/5 to 14% ethanol.

Yield: 88% of theory,
$C_{27}H_{33}N_5O_4 \times HCl$ (491.60/528.06)
Mass spectrum:
(M+H)$^+$=492
(M–H)$^-$=490

EXAMPLE 192

4-{3-[2,5-dimethyl-4-(N-propyl-N-(3-ethoxycarbonyl-propionyl)-amino)-phenyl]-propargylamino}-benzamidine Prepared analogously to Example 2 from N-tert-butoxycarbonyl-4-{3-[2,5-dimethyl-4-(N-propyl-N-(3-ethoxycarbonyl-propionyl)-amino)-phenyl]-propargylamino}-benzamidine and trifluoroacetic acid.

Yield: 58% of theory,
$C_{27}H_{34}N_4O_3 \times CF_3COOH$ (462.59/576.62)
$R_f$ value: 0.2 (silica gel; dichloromethane/methanol=4:1)
Mass spectrum: (M+H)$^+$=463

EXAMPLE 193

4-{3-[2,5-dimethyl-4-(N-cyclobutyl-N-(3-ethoxycarbonyl-propionyl)-amino)-phenyl]-propargylamino}-benzamidine Prepared analogously to Example 2 from N-tert-butoxycarbonyl-4-{3-[2,5-dimethyl-4-(N-cyclobutyl-N-(3-ethoxycarbonyl-propionyl)-amino)-phenyl]-propargylamino}-benzamidine and trifluoroacetic acid.

Yield: 49% of theory,
$C_{28}H_{34}N_4O_3 \times CF_3COOH$ (474.61/588.63)
Mass spectrum: (M+H)$^+$=475

EXAMPLE 194

4-{3-[2,5-dimethyl-4-(N-propyl-N-(3-hydroxycarbonyl-propionyl)-amino)-phenyl]-propargylamino}-benzamidine Prepared analogously to Example 3 from 4-{3-[2,5-dimethyl-4-(N-propyl-N-(3-ethoxycarbonyl-propionyl)-amino)-phenyl]-propargylamino}-benzamidine, lithium hydroxide and subsequent treatment with ammonium chloride.

Yield: 63% of theory,
$C_{25}H_{30}N_4O_3 \times HCl$ (434.54/471.00)
Mass spectrum:
(M+H)$^+$=435
(M–H)$^-$=433

EXAMPLE 195

4-{3-[2,5-dimethyl-4-(N-ethyl-N-(3-ethoxycarbonyl-propionyl)-amino)-phenyl]-propargylamino}-benzamidine Prepared analogously to Example 2 from N-tert-butoxycarbonyl-4-{3-[2,5-dimethyl-4-(N-ethyl-N-(3-ethoxycarbonyl-propionyl)-amino)-phenyl]-propargylamino}-benzamidine and trifluoroacetic acid.

Yield: 49% of theory,
$C_{26}H_{32}N_4O_3 \times CF_3COOH$ (448.57/562.59)
Mass spectrum: (M+H)$^+$=449

EXAMPLE 196

4-{3-[2,5-dimethyl-4-(N-ethyl-N-(3-hydroxycarbonyl-propionyl)-amino)-phenyl]-propargylamino}-benzamidine 0.2 g (0.267 mol) of 4-{3-[2,5-dimethyl-4-(N-ethyl-N-(3-ethoxycarbonyl-propionyl)-amino)-phenyl]-propargylamino}-benzamidine are stirred in 30 ml of 6 molar hydrochloric acid for 19 hours at ambient temperature. Then the mixture is evaporated down in vacuo, the residue is triturated with acetone and suction filtered.

Yield: 98% of theory,
$C_{24}H_{28}N_4O_3 \times HCl$ (420.52/456.98)

EXAMPLE 197

4-{3-[2,5-dimethyl-4-(N-isopropyl-N-(N'-ethoxycarbonylmethyl-N'-methyl-aminomethylcarbonyl)-amino)-phenyl]-propargylamino}-benzamidine Prepared analogously to Example 2 from N-tert-butoxycarbonyl-4-{3-[2,5-dimethyl-4-(N-isopropyl-N-(ethoxycarbonylmethyl-(N-methylamino)methylcarbonyl)-amino)-phenyl]-propargylamino}-benzamidine and trifluoroacetic acid.

Yield: 66% of theory, $C_{28}H_{37}N_5O_3 \times 2\ CF_3COOH$ (491.64/719.68)

Mass spectrum:

$(M+H)^+ = 492$ $(M-H)^- = 490$

EXAMPLE 198

4-{3-[2,5-dimethyl-4-(N-isopropyl-N-(3-ethoxycarbonyl-propionyl)-amino)-phenyl]-propargyloxy}-benzamidine Prepared analogously to Example 1e from 4-{3-[2,5-dimethyl-4-(N-isopropyl-N-(3-ethoxycarbonyl-propionyl)-amino)-phenyl]-propargyloxy}-benzonitrile and hydrochloric acid/ammonium carbonate in ethanol.

Yield: 9% of theory, $C_{27}H_{33}N_3O_4 \times HCl$ (463.59/500.047)

$R_f$ value: 0.62 (Reversed phase silica gel RP-8; methanol/6% saline solution=4:1)

Mass spectrum: $(M+H)^+ = 464$

EXAMPLE 199

4-{3-[2,5-dimethyl-4-(N-isopropyl-N-(3-hydroxycarbonyl-propionyl)-amino)-phenyl]-propargyloxy}-benzamidine Prepared analogously to Example 1e from 4-{3-[2,5-dimethyl-4-(N-isopropyl-N-(3-ethoxycarbonyl-propionyl)-amino)-phenyl]-propargyloxy}-benzamidine, lithium hydroxide and subsequent treatment with glacial acetic acid.

Yield: 65% of theory, $C_{25}H_{29}N_3O_4$ (435.53)

$R_f$ value: 0.62 (Reversed phase silica gel RP-8; methanol/6% saline solution=4:1)

Mass spectrum:

$(M+H)^+ = 436$ $(M-H)^- = 434$

EXAMPLE 200

4-{3-[2,5-dimethyl-4-(N-isopropyl-N-hydroxycarbonylmethyl-aminocarbonylmethylcarbonyl-amino)-phenyl]-propargylamino}-benzamidine Prepared analogously to Example 3 from 4-{3-[2,5-dimethyl-4-(N-isopropyl-N-methoxycarbonylmethylaminocarbonyl-methylcarbonylamino)-phenyl]-propargylamino}-benzamidine, lithium hydroxide and subsequent treatment with glacial acetic acid.

Yield: 3% of theory, $C_{26}H_{31}N_5O_4$ (477.568)

$R_f$ value: 0.74 (Reversed phase silica gel RP-8; methanol/6% saline solution=4:1)

Mass spectrum:

$(M+H)^+ = 478$ $(M+Na)^+ = 500$ $(M-H)^- = 476$

EXAMPLE 201

4-{3-[2,5-dimethyl-4-(N-isopropyl-N-(3-amino-3-ethoxycarbonyl-propionyl)-amino)-phenyl]-propargylamino}-benzamidine Prepared analogously to Example 2 from N-tert-butoxycarbonyl-4-{3-[2,5-dimethyl-4-(N-isopropyl-N-(3-tert-butoxycarbonylamino-3-ethoxycarbonyl-propionyl)-amino)-phenyl]-propargylamino}-benzamidine and trifluoroacetic acid and subsequent treatment with ethanolic hydrochloric acid.

Yield: 86% of theory, $C_{27}H_{35}N_5O_3 \times 2HCl$ (477.62/550.54)

$R_f$ value: 0.77 (Reversed phase silica gel RP-8; methanol/6% saline solution=4:1)

Mass spectrum: $(M+H)^+ = 478$

EXAMPLE 202

4-{3-[2,5-dimethyl-4-(N-isopropyl-N-(3-amino-3-hydroxy-carbonyl-propionyl)-amino)-phenyl]-propargylamino}-benzamidine Prepared analogously to Example 3 from 4-{3-[2,5-dimethyl-4-(N-isopropyl-N-(3-amino-3-ethoxycarbonyl-propionyl)-amino)-phenyl]-propargylamino}-benzamidine and potassium hydroxide and subsequent treatment with ethanolic hydrochloric acid.

Yield: 12% of theory, $C_{25}H_{31}N_5O_3 \times 2HCl$ (449.56/522.49)

$R_f$ value: 0.69 (Reversed phase silica gel RP-8; methanol/6% saline solution=4:1)

Mass spectrum:

$(M+H)^+ = 450$ $(M-H)^- = 448$

EXAMPLE 203

4-{3-[5-fluoro-2-methyl-4-(N-isopropyl-N-ethoxycarbonylmethylaminocarbonyl-amino)-phenyl]-propargylamino}-benzamidine Prepared analogously to Example 2 from N-tert-butoxycarbonyl-4-{3-[5-fluoro-2-methyl-4-(N-isopropyl-N-ethoxycarbonylmethylaminocarbonyl-amino)-phenyl]-propargylamino}-benzamidine and trifluoroacetic acid and subsequent treatment with ethanolic hydrochloric acid.

Yield: 43% of theory, $C_{25}H_{30}FN_5O_3 \times HCl$ (467.55/504.01)

$R_f$ value: 0.2 (silica gel; dichloromethane/methanol 3:1)

(Mass spectrum top of page 81:)
$(M+H)^+ = 421$
$(M-H)^- = 419$

Mass spectrum:
(M+H)⁺=468
(M−H)⁻=466

EXAMPLE 204

4-{3-[5-fluoro-2-methyl-4-(N-isopropyl-N-hydroxycarbonylmethylaminocarbonyl-amino)-phenyl]-propargylamino}-benzamidine Prepared analogously to Example 3 from 4-{3-[5-fluoro-2-methyl-4-(N-isopropyl-N-ethoxycarbonylmethylaminocarbonyl-amino)-phenyl]-propargylamino}-benzamidine, sodium hydroxide and subsequent treatment with glacial acetic acid.

Yield: 92% of theory, $C_{23}H_{26}FN_5O_3$ (439.49)

Mass spectrum:
(M+H)⁺=440
(M+Na)⁺=462
(M−H)⁻=438

EXAMPLE 205

4-{3-[2-methyl-4-(N-isopropyl-N-ethoxycarbonylmethylamino-carbonyl-amino)-phenyl]-propargylamino}-benzamidine Prepared analogously to Example 2 from N-tert-butoxycarbonyl-4-{3-[2-methyl-4-(N-isopropyl-N-ethoxycarbonylmethylaminocarbonyl-amino)-phenyl]-propargylamino}-benzamidine and trifluoroacetic acid.

Yield: 56% of theory, $C_{25}H_{31}N_5O_3 \times CF_3COOH$ (449.55/563.58)

Mass spectrum:
(M+H)⁺=450
(M+CF₃COOH−H)³¹ =562

EXAMPLE 206

4-{3-[2,5-dimethyl-4-(N-cyclobutyl-N-methoxycarbonylmethyl-carbonyl-amino)-phenyl]-propargylamino}-benzamidine Prepared analogously to Example 2 from N-tert-butoxycarbonyl-4-{3-[2,5-dimethyl-4-(N-cyclobutyl-N-methoxycarbonylmethylcarbonyl-amino)-phenyl]-propargylamino}-benzamidine and trifluoroacetic acid.

Yield: 65% of theory, $C_{26}H_{30}N_4O_3 \times CF_3COOH$ (446.55/560.56)

Mass spectrum: (M+H)⁺=447

EXAMPLE 207

4-{3-[2,5-dimethyl-4-(N-isopropyl-N-aminomethylcarbonyl-amino)-phenyl]-propargylamino}-benzamidine Prepared analogously to Example 2 from N-tert-butoxycarbonyl-4-{3-[2,5-dimethyl-4-(N-isopropyl-N-tert-butoxycarbonylaminomethylcarbonyl-amino)-phenyl]-propargylamino}-benzamidine and trifluoroacetic acid.

Yield: 61% of theory, $C_{23}H_{29}N_5O \times 2\ CF_3COOH$ (391.53/619.57)

$R_f$ value: 0.70 (Reversed phase silica gel RP-8; methanol/6% saline solution=4:1)

Mass spectrum: (M+H)⁺=392

EXAMPLE 208

4-{3-[2-methyl-4-(N-isopropyl-N-hydroxycarbonylmethylamino-carbonyl-amino)-phenyl]-propargylamino}-benzamidine Prepared analogously to Example 3 from 4-{3-[2-methyl-4-(N-isopropyl-N-ethoxycarbonylmethylaminocarbonyl-amino)-phenyl]-propargylamino}-benzamidine, sodium hydroxide and subsequent treatment with glacial acetic acid.

Yield: 42% of theory, $C_{23}H_{27}N_5O_3$ (421.50)

Mass spectrum:
(M+H)⁺=422
(M+Na)⁺=444
(M−H)⁻=420

EXAMPLE 209

4-{3-[2-chloro-5-methyl-4-(N-isopropyl-N-ethoxycarbonylmethylaminocarbonyl-amino)-phenyl]-propargylamino}-benzamidine Prepared analogously to Example 2 from N-tert-butoxycarbonyl-4-{3-[2-chloro-5-methyl-4-(N-isopropyl-N-ethoxycarbonylmethylaminocarbonyl-amino)-phenyl]-propargylamino}-benzamidine and trifluoroacetic acid.

Yield: 38% of theory, $C_{25}H_{30}ClN_5O_3 \times CF_3COOH$ (484.00/598.02)

$R_f$ value: 0.4 (silica gel; dichloromethane/methanol=4:1)

Mass spectrum:(M+H)⁺=484/486 (chlorine isotopes)

EXAMPLE 210

4-{3-[2-chloro-5-methyl-4-(N-isopropyl-N-hydroxycarbonylmethylaminocarbonyl-amino)-phenyl]-propargylamino}-benzamidine Prepared analogously to Example 3 from 4-{3-[2-chloro-5-methyl-4-(N-isopropyl-N-ethoxycarbonylmethylaminocarbonyl-amino)-phenyl]-propargylamino}-benzamidine, sodium hydroxide and subsequent treatment with glacial acetic acid.

Yield: 7% of theory, $C_{23}H_{26}ClN_5O_3$ (455.94)

Mass spectrum:
(M+H)⁺=456/458 (chlorine isotopes)
(M+Na)⁺=478/480 (chlorine isotopes)
(M−H)⁻=454/456 (chlorine isotopes)

EXAMPLE 211

4-{3-[2,5-dimethyl-4-(N-isopropyl-N-(3-aminopropionyl)-amino)-phenyl]-propargylamino}-benzamidine Prepared analogously to Example 2 from N-tert-butoxycarbonyl-4-{3-[2,5-dimethyl-4-(N-isopropyl-N-(3-tert-butoxycarbonylamino-propionyl)-amino)-phenyl]-propargylamino}-benzamidine and trifluoroacetic acid.

Yield: 71% of theory,
R$_f$ value: 0.39 (silica gel; dichloromethane/ethanol=4:1)
R$_f$ value: 0.36 (Reversed phase silica gel RP-8; methanol/6% saline solution=4:1)
C$_{24}$H$_{31}$N$_5$O×2CF$_3$COOH (405.55/633.59)

EXAMPLE 212

4-{3-[3-methyl-4-(N-isopropyl-N-ethoxycarbonylmethylamino-carbonyl-amino)-phenyl]-propargylamino}-benzamidine Prepared analogously to Example 2 from N-tert-butoxycarbonyl-4-{3-[3-methyl-4-(N-isopropyl-N-ethoxycarbonylmethylamino-carbonyl-amino)-phenyl]-propargylamino}-benzamidine and trifluoroacetic acid.

Yield: 46% of theory,
R$_f$ value: 0.21 (silica gel; dichloromethane/ethanol=4:1)
C$_{25}$H$_{31}$N$_5$O$_3$×CF$_3$COOH (449.56/563.58)
Mass spectrum:
(M+H)$^+$=450
(M−H)$^-$=448

EXAMPLE 213

4-{3-[3-methyl-4-(N-isopropyl-N-hydroxycarbonylmethylamino-carbonyl-amino)-phenyl]-propargylamino}-benzamidine Prepared from 4-{3-[3-methyl-4-(N-isopropyl-N-ethoxycarbonylmethylaminocarbonyl-amino)-phenyl]-propargylamino}-benzamidine by reacting for 18 hours with 20 ml of 6N HCl and subsequently distilling off the volatile constituents.

Yield: 82% of theory,
R$_f$ value: 0.46 (Reversed phase silica gel RP-8; methanol/5% saline solution=6:4)
C$_{23}$H$_{27}$N$_5$O$_3$×HCl (421.50/457.96)
Mass spectrum:
(M+H)$^+$=422
(M+Na)$^+$=444
(M−H)$^-$=420
(M+HCl−H)$^-$=456/458 (chlorine isotopes)

EXAMPLE 214

4-{3-[2-methyl-4-(N-isopropyl-N-(2-trifluoracetylamino-3-methoxycarbonyl-propionyl)-amino)-phenyl]-propargylamino}-benzamidine Prepared analogously to Example 2 from N-tert-butoxycarbonyl-4-{3-[2-methyl-4-(N-isopropyl-N-(2-trifluoracetylamino-3-methoxycarbonyl-propionyl)-amino)-phenyl]-propargylamino}-benzamidine and trifluoroacetic acid.

Yield: 100% of theory,
R$_f$ value: 0.17 (silica gel; dichloromethane/ethanol=4:1)
C$_{27}$H$_{30}$F$_3$N$_5$O$_4$×CF$_3$COOH (545.57/659.59)
Mass spectrum:
(M+H)$^+$=546
(M−H)$^-$=544
(M+CF3COOH—H)$^-$=658

EXAMPLE 215

4-{3-[2-methyl-4-(N-isopropyl-N-(2-trifluoracetylamino-3-hydroxycarbonyl-propionyl)-amino)-phenyl]-propargylamino}-benzamidine Prepared analogously to Example 213 from 4-{3-[2-methyl-4-(N-isopropyl-N-(2-trifluoracetylamino-3-methoxycarbonyl-propionyl)-amino)-phenyl]-propargylamino}-benzamidine and 6N HCl.

Yield: 100% of theory,
R$_f$ value: 0.42 (Reversed phase silica gel RP-8; methanol/5% saline solution=6:4)
C$_{26}$H$_{28}$F$_3$N$_5$O$_4$×HCl (531.540/568.00)
Mass spectrum:
(M+H)$^+$=532
(M−H)$^-$=530

EXAMPLE 216

4-{3-[2-methyl-4-(N-isopropyl-N-(2-amino-3-hydroxycarbonyl-propionyl)-amino)-phenyl]-propargylamino}-benzamidine Prepared from 0.160 g (0.282 mmol) of 4-{3-[2-methyl-4-(N-isopropyl-N-(2-trifluoracetylamino-3-hydroxycarbonyl-propionyl)-amino)-phenyl]-propargylaminol}-benzamidine and 120 mg of sodium carbonate in 20 ml of methanol by stirring for 5 days at ambient temperature. After subsequent heating to 60° C. for 1 day the volatile constituents are distilled off.

Yield: 98% of theory,
R$_f$ value: 0.46 (Reversed phase silica gel RP-8; methanol/5% saline solution=6:4)
C$_{24}$H$_{29}$N$_5$O$_3$×HCl (435.53/471.99)

EXAMPLE 217

4-{3-[2,5-dimethyl-4-(N-isopropyl-N-(N'-hydroxycarbonylmethyl-N'-methyl-aminomethylcarbonyl)-amino)-phenyl]-propargylamino}-benzamidine Prepared analogously to Example 3 from 4-{3-[2,5-dimethyl-4-(N-isopropyl-N-(N'-ethoxycarbonylmethyl-N'-methyl-aminomethylcarbonyl)-amino)-phenyl]-propargylamino}-benzamidine, sodium hydroxide, subsequent precipitation with glacial acetic acid and repeated chromatographic purification using a HPLC column.

Yield: 2% of theory,
C$_{26}$H$_{33}$N$_5$O$_3$×HCl (463.58/500.04)
Mass spectrum: (M+H)$^+$=464

EXAMPLE 218

4-{3-[2-methyl-4-(N-isopropyl-N-(3-trifluoracetylamino-3-methoxycarbonyl-propionyl)-amino)-phenyl]-propargylamino}-benzamidine Prepared analogously to Example 2 from N-tert-butoxycarbonyl-4-{3-[2-methyl-4-(N-isopropyl-N-(3-trifluoracetylamino-3-methoxycarbonyl-propionyl)-amino)-phenyl]-propargylamino}-benzamidine and trifluoroacetic acid.

Yield: 89% of theory,
R$_f$ value: 0.21 (silica gel; dichloromethane/ethanol=4:1)
C$_{27}$H$_{30}$F$_3$N$_5$O$_4$ × CF$_3$COOH (545.57/659.59)
Mass spectrum:
(M+H)$^+$=546
(M−H)$^-$=544

EXAMPLE 219

4-[3-(3-bromo-5-(2-methyl-pyrrolidinocarbonyl)-furan-2-yl)-propargylamino]benzamidine Prepared analogously to Example 1g from 2,3-dibromo-5-(2-methyl-pyrrolidinocarbonyl)-furan, N-tertbutoxycarbonyl-4-propargylamino-benzamidine, tetrakis(triphenylphosphine)palladium(0), copper(I)iodide and triethylamine in acetonitrile and subsequent cleaving of the tert-butyloxycarbonyl group by trifluoroacetic acid analogously to Example 2.

Yield: 17% of theory, $R_f$ value: 0.28 (silica gel; dichloromethane/ethanol=4:1)

$C_{20}H_{21}BrN_4O_2 \times CF_3COOH$ (429.32/543.34)

Mass spectrum: $(M+H)^+=429/431$ (bromine isotopes)

EXAMPLE 220

4-{3-[2-methyl-4-(N-isopropyl-N-(3-amino-3-methoxycarbonyl-propionyl)-amino)-phenyl]-propargylamino}-benzamidine Prepared analogously to Example 216 from 4-{3-[2-methyl-4-(N-isopropyl-N-(3-trifluoracetylamino-3-methoxycarbonyl-propionyl)-amino)-phenyl]-propargylamino}-benzamidine and sodium carbonate in methanol.

Yield: 93% of theory, $R_f$ value: 0.45 (Reversed phase silica gel RP-8; methanol/5% saline solution=6:4)

$C_{25}H_{31}N_5O_3 \times CF_3COOH$ (449.56/563.58)

EXAMPLE 221

4-{3-[3-methyl-4-(N-isopropyl-N-methoxycarbonylmethylcarbonyl-amino)-phenyl]-propargylamino}-benzamidine Prepared analogously to Example 2 from N-tert-butoxycarbonyl-4-{3-[3-methyl-4-(N-isopropyl-N-methoxycarbonylmethylcarbonyl-amino)-phenyl]-propargylamino}-benzamidine and trifluoroacetic acid.

Yield: 55% of theory, $R_f$ value: 0.21 (silica gel; dichloromethane/ethanol=4:1)

$C_{24}H_{28}N_4O_3 \times CF_3COOH$ (420.52/534.54)

Mass spectrum:

$(M+H)^+=421$ $(M+CF_3COOH-H)^-=533$

EXAMPLE 222

4-{3-[3-methyl-4-(N-cyclopentyl-N-methoxycarbonylmethylcarbonyl-amino)-phenyl]-propargylamino}-benzamidine Prepared analogously to Example 2 from N-tert-butoxycarbonyl-4-{3-[3-methyl-4-(N-cyclopentyl-N-methoxycarbonylmethylcarbonyl-amino)-phenyl]-propargylamino}-benzamidine and trifluoroacetic acid.

Yield: 85% of theory, $R_f$ value: xxxx (silica gel; dichloromethane/ethanol=4:1)

$C_{26}H_{30}N_4O_3 \times CF_3COOH$ (446.55/560.57)

Mass spectrum:

$(M+H)^+=447$ $(M+CF_3COOH-H)^-=559$

EXAMPLE 223

4-{3-[3-methyl-4-(N-isopropyl-N-hydroxycarbonylmethylcarbonyl-amino)-phenyl]-propargylamino}-benzamidine Prepared analogously to Example 213 from 4-{3-[3-methyl-4-(N-isopropyl-N-methoxycarbonylmethylcarbonyl-amino)-phenyl]-propargylamino}-benzamidine and 6N HCl.

Yield: 100% of theory, $R_f$ value: 0.40 (silica gel; dichloromethane/ethanol=4:1)

$C_{23}H_{26}N_4O_3 \times HCl$ (406.48/442.94)

Mass spectrum:

$(M+H)^+=407$ $(M-H)^-=405$

EXAMPLE 224

4-{3-[3-methyl-4-(N-cyclopentyl-N-hydroxycarbonylmethyl-carbonyl-amino)-phenyl]-propargylamino}-benzamidine Prepared analogously to Example 213 from 4-{3-[3-methyl-4-(N-cyclopentyl-N-methoxycarbonylmethylcarbonyl-amino)-phenyl]-propargylamino}-benzamidine and 6N HCl.

Yield: 92% of theory, $R_f$ value: 0.23 (silica gel; dichloromethane/ethanol=4:1)

$C_{25}H_{28}N_4O_3 \times HCl$ (432.52/468.99)

Mass spectrum:

$(M+H)^+=433$ $(M-H)^-=431$

The following compounds may be prepared analogously to the preceding Examples:

4-{3-[2-bromo-5-methyl-4-(N-isopropyl-N-(2-ethoxycarbonylethylcarbonyl)-amino)-phenyl]-propargylamino}-benzamidine 4-{3-[2,5-dimethyl-4-(N-isopropyl-N-(2-ethoxycarbonyl-2-amino-acetylamino)-phenyl]-propargylamino}-benzamidine 4-{3-[2,5-dimethyl-4-(N-isopropyl-N-(2-hydroxycarbonyl-2-amino-acetylamino)-phenyl]-propargylamino}-benzamidine 4-{3-[2,5-bis(trifluoromethyl)-4-(N-isopropyl-N-ethoxycarbonyl-methylaminocarbonyl-amino)-phenyl]-propargylamino}-benzamidine 4-{3-[2,5-bis(trifluoromethyl)-4-(N-isopropyl-N-hydroxycarbonyl-methylaminocarbonyl-amino)-phenyl]-propargylamino}-benzamidine 4-{3-[2-trifluoromethyl-5-methyl-4-(N-isopropyl-N-ethoxycarbonyl-methylaminocarbonyl-amino)-phenyl]-propargylamino}-benzamidine 4-{3-[2-trifluoromethyl-5-methyl-4-(N-isopropyl-N-hydroxycarbo-nylmethylaminocarbonyl-amino)-phenyl]-propargylamino}-benzamidine 4-{3-[2-trifluoromethyl-4-(N-isopropyl-N-ethoxycarbonylmethylaminocarbonyl-amino)-phenyl]-propargylamino}-benzamidine 4-{3-[2-trifluoromethyl-4-(N-isopropyl-N-hydroxycarbonylmethylaminocarbonyl-amino)-phenyl]-propargylamino}-benzamidine 4-{3-[2,5-dimethyl-4-(N-isopropyl-N-(2-ethoxycarbonylethylaminocarbonyl)-amino)-phenyl]-propargylamino}-benzamidine 4-{3-[2,5-dimethyl-4-(N-isopropyl-N-(2-hydroxycarbonylethylaminocarbonyl)-amino)-phenyl]-propargylamino}-benzamidine 4-{3-[2,5-dimethyl-4-(N-isopropyl-N-(ethoxycarbonylmethylaminomethylcarbonyl)-amino)-phenyl]-propargylamino}-benzamidine 4-{3-[2,5-dimethyl-4-(N-isopropyl-N-(hydroxycarbonylmethylaminomethylcarbonyl)-amino)-phenyl]-propargylamino}-benzamidine 4-{3-[2,5-dimethyl-4-(N-isopropyl-N-(4-amino-4-ethoxycarbonyl-butanoyl)-amino)-phenyl]-propargylamino}-benzamidine 4-{3-[2,5-dimethyl-4-(N-isopropyl-N-(4-amino-4-hydroxycarbonyl-butanoyl)-amino)-phenyl]-propargylamino}-benzamidine 4-{3-[2,5-dimethyl-4-(N-isopropyl-N-(2-amino-4-ethoxycarbonyl-butanoyl)-amino)-phenyl]-propargylamino}-benzamidine 4-{3-[2,5-dimethyl-4-(N-isopropyl-N-(2-amino-4-hydroxycarbonyl-butanoyl)-amino)-phenyl]-propargylamino}-benzamidine 4-{3-[2,5-dimethyl-4-(N-isopropyl-N-(2-ethoxycarbonylethylaminocarbonyl)-amino)-phenyl]-propargylamino}-benzamidine 4-{3-[2,5-dimethyl-4-(N-isopropyl-N-(2-hydroxycarbonylethylaminocarbonyl)-amino)-phenyl]-propargylamino}-benzamidine 4-{3-[2-methyl-4-(N-isopropyl-N-(3-amino-3-hydroxycarbonyl-propionyl)-amino)-phenyl]-propargylamino}-benzamidine 4-{3-[2-methyl-4-(N-isopropyl-N-(2-amino-3-methoxycarbonyl-propionyl)-amino)-phenyl]-propargylamino}-benzamidine 4-{3-[2,5-dimethyl-4-(N-isopropyl-N-aminocarbonyl-amino)-phenyl]-propargylamino}-benzamidine 4-{3-[2,5-dimethyl-4-(N-isopropyl-N-(piperazin-1-yl-carbonyl)-amino)-phenyl]-propargylamino}-benzamidine 4-{3-[2,5-dimethyl-4-(N-isopropyl-N-(piperazin-1-yl-methylcarbonyl)-amino)-phenyl]-propargylamino}-benzamidine 4-{3-[2,5-dimethyl-4-(N-isopropyl-N-(2-pyrrolidinon-5-yl-carbonyl)-amino)-phenyl]-propargylamino}-benzamidine 4-{3-[3-bromo-5-pyrrolidinocarbonyl-furan-2-yl]-propargylamino}-benzamidine

EXAMPLE 225

Dry Ampoule Containing 75 mg of Active Substance Per 10 ml

Composition

| | |
|---|---|
| Active substance | 75.0 mg |
| Mannitol | 50.0 mg |
| water for injections | ad 10.0 ml |

Preparation

Active substance and mannitol are dissolved in water. After packaging the solution is freeze-dried. To produce the solution ready for use in injections, the product is dissolved in water.

EXAMPLE 226

Dry Ampoule Containing 35 mg of Active Substance Per 2 ml

Composition

| | |
|---|---|
| Active substance | 35.0 mg |
| Mannitol | 100.0 mg |
| water for injections | ad 2.0 ml |

Preparation

Active substance and mannitol are dissolved in water. After packaging, the solution is freeze-dried. To produce the solution ready for use in injections, the product is dissolved in water.

EXAMPLE 227

Tablet Containing 50 mg of Active Substance

Composition

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 228

Tablet Containing 350 mg of Active Substance

Composition

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 229

Capsules Containing 50 mg of Active Substance

Composition

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation (1) is granulated with (3). This granulate is added to the mixture of (2) and (4) with vigorous mixing.

This powder mixture is packed into size 3 hard gelatine capsules in a capsule filling machine.

EXAMPLE 230
Capsules Containing 350 mg of Active Substance
Composition

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation (1) is granulated with (3). This granulate is added to the mixture of (2) and (4) with vigorous mixing.

This powder mixture is packed into size 0 hard gelatine capsules in a capsule filling machine.

EXAMPLE 231
Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation

The polyethyleneglycol is melted together with polyethylenesorbitan monostearate. At 40° C. the ground active substance is homogeneously dispersed in the melt. This is then cooled to 38° C. and poured into slightly chilled suppository moulds.

What is claimed:

1. A compound of the formula

$$Ar-A-(HCR_1)-X-Y \quad (I),$$

wherein:

A denotes an ethynylene group, $R_1$ denotes a hydrogen atom or a $C_{1-3}$-alkyl group, Ar denotes a phenyl group substituted by the groups $R_2$ to $R_4$, whilst $R_2$ denotes
a phenyl or phenoxy group,
a $C_{1-3}$-alkyl group which may be substituted by a phenyl, phenylamino, N-($C_{1-3}$-alkyl)-phenylamino or N-($C_{1-3}$alkanoyl)-phenylamino group,
a carboxy or $C_{1-3}$-alkoxycarbonyl group,
a benzoyl or phenylsulphonyl group wherein in each case the phenyl moiety may additionally be substituted by a fluorine, chlorine or bromine atom, by a methyl, methoxy, carboxy or $C_{1-}$-alkoxycarbonyl group, whilst in the above-mentioned benzoyl groups the oxygen atom may additionally be replaced by a carboxy-$C_{1-3}$-alkoxyimino or $C_{1-3}$-alk-oxycarbonyl-$C_{1-3}$-alkoxyimino group,
a $C_{1-5}$-alkylamino group which may be substituted in the alkyl moiety by a phenyl, carboxy, $C_{1-3}$-alkoxycarbonyl, carboxy-$C_{1-3}$-alkylaminocarbonyl, $C_{1-3}$-alkoxycarbonyl-$C_{1-3}$-alkylaminocarbonyl, N-($C_{1-3}$-alkyl)carboxy-$C_{1-3}$-alkylaminocarbonyl or N-($C_{1-3}$-alkyl)-$C_{1-3}$-alkoxycarbonyl-$C_{1-3}$-alkylaminocarbonyl group, or a $C_{3-7}$-cycloalkylamino group, whilst the above-mentioned groups may each additionally be substituted at the amino nitrogen atom by a $C_{3-7}$-cycloalkanoyl, benzoyl or phenylsulphonyl group, by a carboxy-$C_{1-3}$-alkylcarbonyl or $C_{1-3}$-alkoxycarbonyl-$C_{1-3}$-alkylcarbonyl group wherein the alkyl moiety of the alkylcarbonyl group is substituted in each case by an amino or trifluoroacetylamino group, by a $C_{2-4}$-alkanoyl group, which may be substituted in the alkanoyl moiety by an amino, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$-alkylaminocarbonyl, $C_{1-3}$-alkoxycarbonyl-$C_{1-3}$-alkylaminocarbonyl, N-($C_{1-3}$-alkyl)-carboxy-$C_{1-3}$-alkylaminocarbonyl or N-($C_{1-3}$-alkyl)-$C_{1-3}$-alkoxycarbonyl-$C_{1-3}$-alkylaminocarbonyl group,
by a carboxy-$C_{1-2}$-alkylaminocarbonyl, $C_{1-3}$-alkoxycarbonyl-$C_{1-2}$-alkylaminocarbonyl, carboxy-$C_{1-3}$-alkylaminocarbonyl-$C_{1-2}$-alkylaminocarbonyl or $C_{1-3}$-alkoxycarbonyl-$C_{1-3}$-alkylaminocarbonyl-$C_{1-2}$-alkylaminocarbonyl group, a formyl, pyridylcarbonyl, thienylcarbonyl, imidazolylcarbonyl, 1-methyl-imidazolylcarbonyl, thiazolylcarbonyl or indolyl-carbonyl group, a benzimidazol-1-yl, benzimidazol-1-yl-methyl or 5-oxo-4,5-dihydro-pyrazol-3-yl group optionally substituted by 1 or 2 methyl groups, a pyrazol-1-yl group substituted by a phenyl group, by a phenyl group and a $C_{1-4}$-alkyl group or by one or two $C_{1-4}$-alkyl groups wherein an alkyl substituent may at the same time be substituted by a carboxy or $C_{1-3}$-alkoxycarbonyl group, or a carbonyl group which is substituted
by a $C_{1-5}$-alkyl group optionally substituted by a carboxy or $C_{1-3}$-alkoxycarbonyl group,
by a $C_{3-7}$-cycloalkyl group,
by an amino or $C_{1-5}$-alkylamino group, which are in each case substituted at the amino nitrogen atom by a $C_{1-3}$-alkyl group which may be substituted by a $C_{3-7}$-cycloalkyl, phenyl, pyrrolidinyl or pyridinyl group or in the 2 or 3 position by a di-($C_{1-3}$-alkyl)-amino group, or by a di-($C_{1-3}$-alkyl)-amino group,
by a carboxy-$C_{1-3}$-alkylamino or $C_{1-3}$-alkoxycarbonyl-$C_{1-3}$-alkylamino group which is in each case substituted at the amino nitrogen atom by a pyrazolyl group optionally substituted by a $C_{1-3}$-alkyl group,
by a 3- to 7-membered cycloalkyleneimino group which may be substituted by one or two $C_{1-3}$-alkyl groups, whilst the above-mentioned pyrrolidino groups optionally substituted by a methyl group may additionally be substituted by a hydroxymethyl, carboxy, $C_{1-3}$-alkoxycarbonyl, carboxy-$C_{1-3}$-alkyl, $C_{1-3}$-alkoxycarbonyl-$C_{1-3}$-alkyl, carboxy-$C_{1-3}$-alkyloxy-$C_{1-3}$-alkyl, $C_{1-3}$-alkoxycarbonyl-$C_{1-3}$-alkyloxy-$C_{1-3}$-alkyl, carboxy-$C_{1-3}$-alkylamino-$C_{1-3}$-alkyl, N-(C-$_{1-3}$-alkyl)-carboxy-$C_{1-3}$-alkylamino-$C_{1-3}$-alkyl, $C_{1-3}$-alkoxycarbonyl-$C_{1-3}$-alkylamino-$C_{1-3}$-alkyl, N-($C_{1-3}$-alkyl)-carboxy-$C_{1-3}$-alkylamino-$C_{1-3}$- alkyl or N-($C_{1-3}$-alkyl)-$C_{1-3}$-alkoxycarbonyl-$C_{1-3}$-alkylamino-$C_{1-3}$-alkyl group,
by a morpholino, piperazino, 4-methyl-piperazino, piperazino-$C_{1-3}$-alkyl, dihydropyrazolo, tetrahydropyrazolo, tetrahydroisoxazolo or 7-azabicycloheptyl group or
by a N-($C_{1-3}$-alkyl)phenyl or N-($C_{1-3}$-alkyl)-pyridylamino group optionally substituted in the alkyl moiety by a carboxy or $C_{1-3}$-alkoxycarbonyl group, $R_3$ denotes
 a hydrogen, fluorine, chlorine or bromine atom,
 a hydroxy, $C_{1-3}$-alkoxy, trifluoromethyl, amino or $C_{2-3}$-alkanoylamino group,
 a $C_{1-3}$-alkyl group which may be substituted by a hydroxy, carboxy, $C_{1-3}$-alkoxycarbonyl, carboxy-$C_{1-3}$-alkoxy, $C_{1-3}$-alkoxycarbonyl-$C_{1-3}$-alkoxy, carboxy-$C_{1-3}$alkylaminocarbonyl, $C_{1-3}$-alkoxycarbonyl-$C_{1-3}$-alkylaminocarbonyl, N-($C_{1-3}$-alkyl)-carboxy-$C_{1-3}$-alkylaminocarbonyl or N-($C_{1-3}$-alkyl)-$C_{1-3}$-alkoxycarbonyl-$C_{1-3}$-alkylaminocarbonyl group,
 a $C_{1-3}$-alkyl group which is substituted by a carboxy-$C_{1-3}$-alkylamino, $C_{1-3}$-alkoxycarbonyl-$C_{1-3}$-alkylamino, N-($C_{1-3}$-alkyl)-carboxy-$C_{1-3}$-alkylamino or $C_{1-3}$-alkoxycarbonyl-$C_{1-3}$-alkylaminocarbonyl group,
 a $C_{2-3}$-alkenyl group substituted by a carboxy or $C_{1-3}$-alkoxycarbonyl group or
 a carbimino group optionally substituted at the carbon atom by a $C_{1-3}$-alkyl group, which is substituted at the imino nitrogen atom by a carboxy-$C_{1-3}$-alkoxy, $C_{1-3}$-alkoxycarbonyl-$C_{1-3}$-alkoxy or aminocarbonylamino group,
 or $R_2$ and $R_3$ together denote a —CO—O—$CH_2$-group and $R_4$ denotes a hydrogen, fluorine, chlorine or bromine atom, a $C_{1-3}$-alkyl or trifluoromethyl group, X denotes an —NH-group optionally substituted by a $C_{1-3}$-alkyl group and Y denotes a cyclohexyl group substituted by an amino group, a phenylene group substituted by an amidino group, which may be substituted by a benzoyl or $C_{1-8}$-alkoxycarbonyl group, whilst the above-mentioned phenylene group may be substituted by a methyl or methoxy group, or a tautomer or salt thereof.

2. A compound of the formula

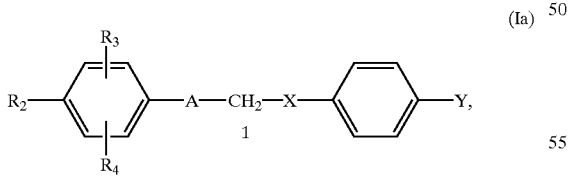

(Ia)

wherein

A denotes an ethynylene group,

X denotes an —NH— group optionally substituted by a methyl group, $R_2$ denotes
 a $C_{1-4}$-alkylcarbonylamino or $C_{3-5}$-cycloalkylcarbonylamino group, which is substituted in each case at the amino nitrogen atom by a carboxy-$C_{1-2}$-alkyl, $C_{1-3}$-alkoxycarbonyl-$C_{1-2}$-alkyl, carboxy-$C_{1-2}$-alkylaminocarbonyl-$C_{1-2}$-alkyl or $C_{1-3}$-alkoxycarbonyl-$C_{1-2}$-alkylaminocarbonyl-$C_{1-2}$-alkyl group,
 a $C_{1-4}$-alkylamino or $C_{3-5}$-cycloalkylamino group, which is substituted in each case at the amino nitrogen atom by a carboxy-$C_{1-3}$-alkylcarbonyl, $C_{1-3}$-alkoxycarbonyl-$C_{1-3}$-alkylcarbonyl, carboxy-$C_{1-2}$-alkylaminocarbonyl-$C_{1-2}$-alkylcarbonyl, $C_{1-3}$-alkoxycarbonyl-$C_{1-2}$-alkylaminocarbonyl-$C_{1-2}$-alkylcarbonyl, carboxy-$C_{1-2}$-alkylaminocarbonyl, $C_{1-3}$-alkoxycarbonyl-$C_{1-2}$-alkylaminocarbonyl, carboxy-$C_{1-2}$-alkylaminocarbonyl-$C_{1-2}$-alkylaminocarbonyl or $C_{1-3}$-alkoxycarbonyl-$C_{1-2}$-alkylaminocarbonyl-$C_{1-2}$-alkylaminocarbonyl group optionally substituted in the alkyl moiety by an amino group, or by a carboxymethyloxymethylcarbonyl, $C_{1-3}$-alkoxycarbonyl-methyloxymethylcarbonyl, carboxymethylaminomethylcarbonyl, $C_{1-3}$-alkoxycarbonyl-methylaminomethylcarbonyl, N-methyl-carboxymethylaminomethylcarbonyl, N-methyl-$C_{1-3}$-alkoxycarbonyl-carboxymethylaminomethylcarbonyl, aminomethylcarbonyl, 2-amino-ethylcarbonyl, carboxy-$C_{1-2}$-alkylaminocarbonylmethyloxymethylcarbonyl, $C_{1-3}$-alkoxycarbonyl-$C_{1-2}$-alkylaminocarbonylmethyloxymethylcarbonyl, carboxy-$C_{1-2}$-alkylaminocarbonylmethylaminomethylcarbonyl, $C_{1-3}$-alkoxycarbonyl-$C_{1-2}$-alkylaminocarbonylmethylaminomethylcarbonyl, N-methyl-carboxy-$C_{1-2}$-alkylaminocarbonylmethylaminomethylcarbonyl or N-methyl-$C_{1-3}$-alkoxycarbonyl-$C_{1-2}$-alkylaminocarbonylmethylaminomethylcarbonyl group, or
 a carbonyl group which is substituted
  by a cyclopentyl group,
  by a $C_{3-5}$-alkyl group which may additionally be substituted by a carboxy or $C_{1-3}$-alkoxycarbonyl group,
  by a $C_{1-4}$-alkylamino, phenylamino or pyridylamino group substituted at the amino nitrogen atom by a $C_{1-4}$-alkyl, carboxy-$C_{1-3}$-alkyl or $C_{1-3}$-alkoxycarbonyl-$C_{1-3}$-alkyl group,
  by a pyrrolidino group substituted by a methyl, hydroxymethyl, amino, carboxy, $C_{1-3}$-alkoxycarbonyl, carboxy-$C_{1-2}$-alkyl, $C_{1-3}$-alkoxycarbonyl-$C_{1-2}$-alkyl, carboxymethyloxymethyl, $C_{1-3}$-alkoxycarbonylmethyloxymethyl, carboxymethylaminomethyl, $C_{1-3}$-alkoxycarbonyl-methylaminomethyl, carboxymethylaminocarbonylmethyloxymethyl or $C_{1-3}$-alkoxycarbonylmethylaminocarbonylmethyloxymethyl group, $R_3$ denotes
 a hydrogen, fluorine, chlorine or bromine atom or a trifluoromethyl group,
 a $C_{1-2}$-alkyl group optionally substituted by a hydroxy, carboxy, $C_{1-3}$-alkoxycarbonyl, carboxymethyloxy, $C_{1-3}$-alkoxycarbonyl-methyloxy, carboxymethylamino, N-methyl-carboxymethylamino, $C_{1-3}$-alkoxycarbonylmethylamino, N-methyl-$C_{1-3}$-alkoxycarbonyl-methylamino, carboxymethylaminocarbonyl or $C_{1-3}$-alkoxycarbonylmethylaminocarbonyl group, a vinyl group substituted by a carboxy or $C_{1-3}$-alkoxycarbonyl group, $R_4$ denotes a hydrogen, fluorine, chlorine or bromine atom, a methyl, ethyl or trifluoromethyl group and Y denotes an amidino group optionally substituted by a $C_{1-8}$-alkoxycarbonyl or benzoyl group, or a tautomer or salt thereof.

3. A compound of the formula Ia according to claim 2, wherein

A denotes an ethynylene group,

X denotes an —NH— group, $R_2$ denotes a $C_{1-4}$-alkylaminocarbonyl group, which is substituted in each case at the amino nitrogen atom by a carboxy-$C_{1-2}$-alkyl or $C_{1-3}$-alkoxycarbonyl-$C_{1-2}$-alkyl group, a $C_{1-4}$alkylamino group which is substituted at the amino nitrogen atom by a carboxy-$C_{1-3}$-alkylcarbonyl, $C_{1-3}$-alkoxycarbonyl-$C_{1-3}$-alkylcarbonyl, carboxy-$C_{1-2}$-alkylaminocarbonyl or $C_{1-3}$-alkoxycarbonyl-$C_{1-2}$-alkylaminocarbonyl group, or a carbonyl group which is substituted by a $C_{3-5}$-alkyl group which may additionally be substituted by a carboxy or $C_{1-3}$-alkoxycarbonyl group, by a $C_{1-4}$-alkylamino or pyridylamino group substituted at the amino nitrogen atom by a carboxy-$C_{1-3}$-alkyl or $C_{1-3}$-alkoxycarbonyl-$C_{1-3}$-alkyl group, by a pyrrolidino group optionally substituted by a methyl group, $R_3$ denotes a $C_{1-2}$-alkyl group optionally substituted by a carboxy or $C_{1-3}$-alkoxycarbonyl group, $R_4$ denotes a hydrogen atom or a methyl group and Y denotes an amidino group optionally substituted by a $C_{1-8}$-alkoxycarbonyl or benzoyl group, or a tautomer or salt thereof.

4. A compound selected from the group consisting of:

(a) rac-4-{3-[5-ethoxycarbonylmethyl-2-methyl-4-(2-methyl-pyrrolidinocarbonyl)-phenyl]-propargylamino}benzamidine, (b) rac-4-{3-[2,5-dimethyl-4-(2-methyl-pyrrolidinocarbonyl)-phenyl]-propargylamino}benzamidine, (c) 4-[3-(2,5-dimethyl-4-isopropylcarbonyl-phenyl)propargyl-amino]benzamidine, (d) 4-{3-[2,5-dimethyl-4-(N-methyl-N-pyridin-2-yl-aminocarbonyl)-phenyl]propargylamino)}benzamidine, (e) 4-{3-[2,5-dimethyl-4-(N-methyl-N-pyridin-2-yl-aminocarbonyl)-phenyl]prop-1-ylamino}benzamidine, (f) 4-[3-(3-methyl-4-pyrrolidinocarbonyl-phenyl)-propargyl-amino]-benzamidine, (g) 4-{3-[2,5-dimethyl-4-(N-(2-methoxycarbonyl-ethyl)-N-ethyl-carbonylamino)-phenyl]-propargylamino}benzamidine, (h) 4-{3-[2,5-dimethyl-4-(N-isopropyl-N-hydroxycarbonylmethyl-aminocarbonyl-amino)-phenyl]-propargylamino}-benzamidine and (i) 4-{3-[2,5-dimethyl-4-(N-isopropyl-N-hydroxycarbonylmethyl-carbonyl-amino)-phenyl]-propargylamino}-benzamidine or a salt thereof.

5. A physiologically acceptable salt of a compound according to claim 1, 2 or 3, wherein Y does not contain a cyano group, or of a compound according to claim 4.

6. A pharmaceutical composition comprising a compound according to claim 1, 2 or 3, wherein Y does not contain a cyano group, or a compound according to claim 4, or a physiologically acceptable salt thereof, together with a pharmaceutically acceptable carriers or diluent.

7. A method of treating a patient to prolong the thrombin time in such patient, which method comprises administering to such patient a thrombin time prolonging amount of a compound according to claim 1, 2 or 3, wherein Y does not contain a cyano group, or a compound according to claim 4, or a physiologically acceptable salt thereof.

* * * * *